US009518254B2

(12) United States Patent
Wolkowicz

(10) Patent No.: US 9,518,254 B2
(45) Date of Patent: *Dec. 13, 2016

(54) COMPOSITIONS AND METHODS FOR IDENTIFYING ENZYME AND TRANSPORT PROTEIN INHIBITORS

(75) Inventor: Roland Wolkowicz, San Diego, CA (US)

(73) Assignee: San Diego State University Research Foundation, San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/266,777

(22) PCT Filed: May 3, 2010

(86) PCT No.: PCT/US2010/033437
§ 371 (c)(1),
(2), (4) Date: Mar. 12, 2012

(87) PCT Pub. No.: WO2010/129485
PCT Pub. Date: Nov. 11, 2010

(65) Prior Publication Data
US 2012/0172253 A1   Jul. 5, 2012

Related U.S. Application Data

(60) Provisional application No. 61/175,358, filed on May 4, 2009, provisional application No. 61/183,008, filed
(Continued)

(51) Int. Cl.
*C40B 30/06* (2006.01)
*C12N 9/50* (2006.01)
(Continued)

(52) U.S. Cl.
CPC ............. *C12N 9/506* (2013.01); *C12Q 1/37* (2013.01); *G01N 33/5076* (2013.01);
(Continued)

(58) Field of Classification Search
CPC ................ C12N 9/506; G01N 2333/9513
(Continued)

(56) References Cited

U.S. PATENT DOCUMENTS 6,333,167 B1   12/2001   Quinet et al.
6,699,702 B1    3/2004   Patel et al.
(Continued)

FOREIGN PATENT DOCUMENTS

WO      2010129485 A3   11/2010

OTHER PUBLICATIONS

Agarwal et al., Journal of Virology, May 1998, pp. 3720-3728.*
(Continued)

*Primary Examiner* — Larry Riggs
*Assistant Examiner* — Karla Dines
(74) *Attorney, Agent, or Firm* — Greer, Burns & Crain, Ltd.; Gregory P. Einhorn

(57) ABSTRACT

The invention is directed to compositions to screen for small molecule drugs that inhibit proteases, such as viral proteases, e.g., HIV proteases; and methods for making and using these compositions. The invention provides compositions and methods for identifying compositions, e.g., drug molecules, that can inhibit proteases, e.g., HIV proteases. In alternative embodiments, the invention provides cell-based assays to screen for compositions, e.g., small molecules or drugs, that inhibit or modify the activity of enzymes such as calcium-dependent protein convertases involved in HIV envelop protein processing, including cleavage of the HIV gp160 envelope precursor, resulting in gp120 and gp41 envelope products.

15 Claims, 45 Drawing Sheets

Related U.S. Application Data on Jun. 1, 2009, provisional application No. 61/247,446, filed on Sep. 30, 2009, provisional application No. 61/291,088, filed on Dec. 30, 2009, provisional application No. 61/312,760, filed on Mar. 11, 2010, provisional application No. 61/312,839, filed on Mar. 11, 2010.

(51) Int. Cl.
*C12Q 1/37* (2006.01)
*G01N 33/50* (2006.01)

(52) U.S. Cl.
CPC ...... *C07K 2319/01* (2013.01); *C07K 2319/02* (2013.01); *C07K 2319/03* (2013.01); *C12N 2503/02* (2013.01); *C12N 2510/00* (2013.01); *G01N 2333/9513* (2013.01); *G01N 2500/02* (2013.01); *G01N 2500/10* (2013.01)

(58) Field of Classification Search
USPC .......................................................... 506/10
See application file for complete search history.

(56) References Cited

U.S. PATENT DOCUMENTS

| | | |
|---|---|---|
| 2003/0100707 A1* | 5/2003 | Hwang et al. ............... 530/350 |
| 2003/0147810 A1 | 8/2003 | Ross et al. |
| 2004/0042961 A1* | 3/2004 | Menard et al. ............... 424/9.6 |
| 2009/0005264 A1* | 1/2009 | Rakestraw et al. ............ 506/14 |
| 2009/0029369 A1* | 1/2009 | Cottier et al. .................... 435/6 |
| 2009/0320831 A1* | 12/2009 | Lanahan et al. ................ 127/37 |

OTHER PUBLICATIONS

Hu et al., Journal of Virological Methods, 128, 2005, pp. 93-103.*
Vincinti et al., Clinical Infectious Diseases, 2007, 44, pp. 1657-1661.*
Nickitas-Etienne, International Preliminary Report on Patentability and Written Opinion, PCT/US2010/033437, The International Bureau of WIPO, Nov. 9, 2011.
Noh, International Search Report, PCT/US2010/033437, Korean Intellectual Property Office, Apr. 12, 2011.
Hovanessian et al., "The Caveolin-1 Binding Domain of HIV-1 Glycoprotein gp41 is an Efficient B Cell Epitope Vaccine Candidate against Virus Infection", Immunity, vol. 21, Nov. 2004, pp. 617-627.
Jaakola et al., "G-Protein-Coupled Receptor Domain Overexpression in Halobacterium salinarum: Long-Range Transmembrane Interactions in Heptahelical Membrane Proteins", Proteins: Structure, Function, and Bioinformatics 60:412-423 (2005).

* cited by examiner

Figure 19
A. No Dox, no GFP
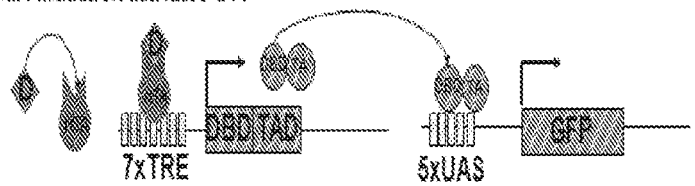
B. Gal4 induction activates GFP
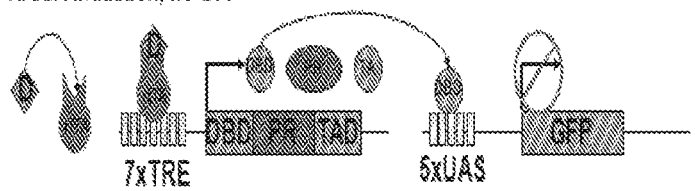
C. PR/Gal4 induction, no GFP
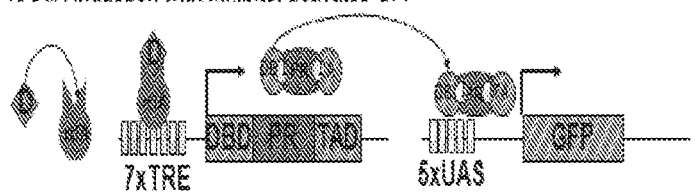
D. PR/Gal4 induction with inhibitor activates GFP Figure 20A
Figure 20B
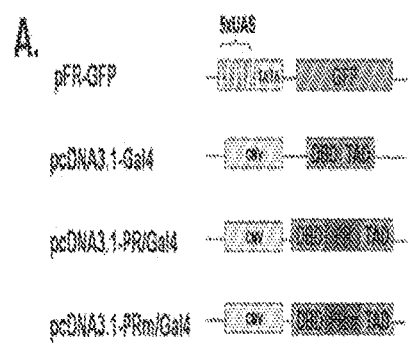
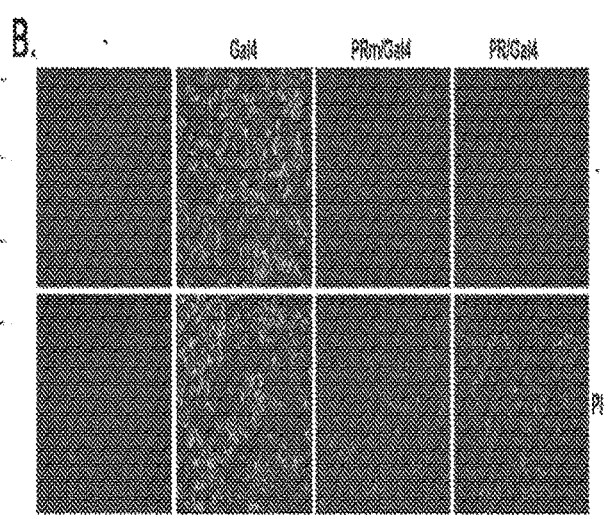
Figure 20C
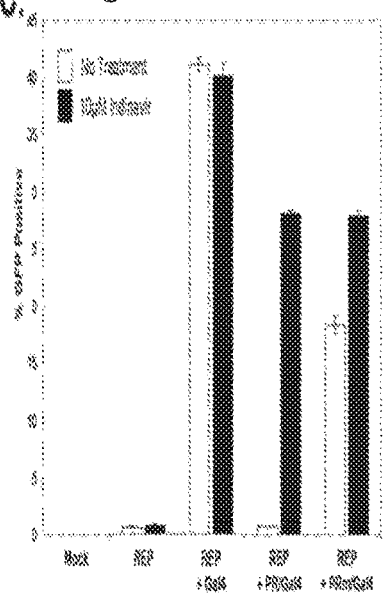

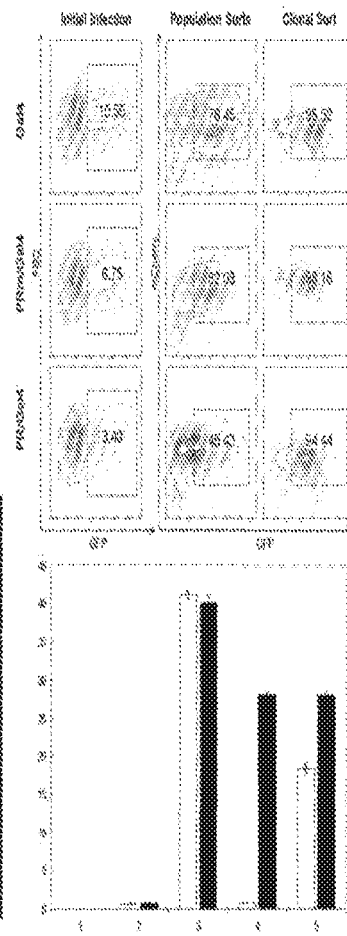
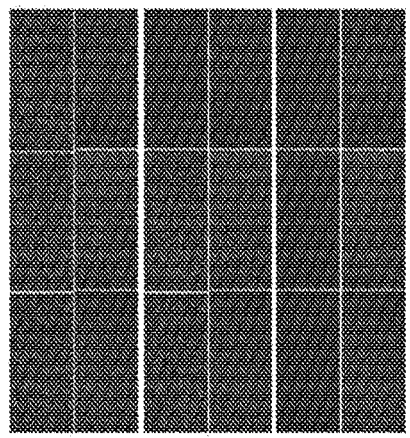
Figure 21A
Figure 21B
Figure 21C
Figure 21D

Figure 22A
Figure 22B
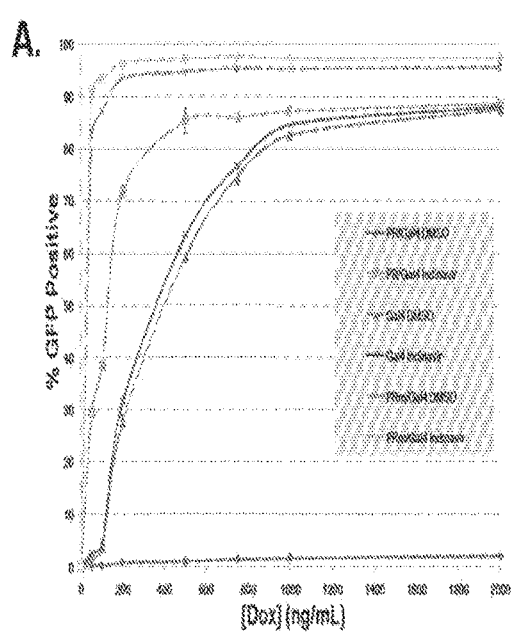
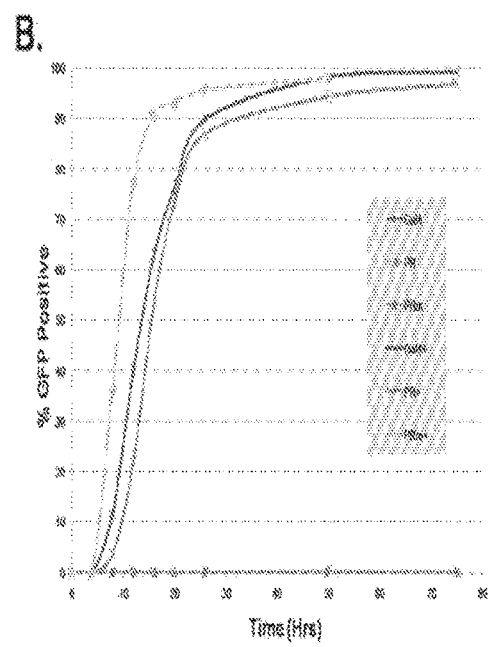

Figure 38
Scaffold construct
Library construct
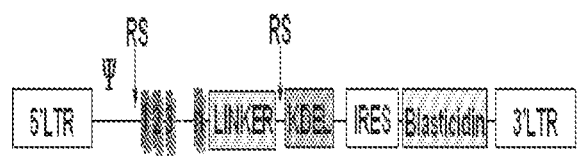

SEQUENCE LISTING

<160> NUMBER OF SEQ ID NOS: 19

<210> SEQ ID NO 1
<211> LENGTH: 4
<212> TYPE: PRT
<213> ORGANISM: artificial sequence
<220> FEATURE:
<223> OTHER INFORMATION: synthetic peptide

<400> SEQUENCE: 1

Lys Asp Glu Leu
1

<210> SEQ ID NO 2
<211> LENGTH: 9
<212> TYPE: PRT
<213> ORGANISM: artificial sequence
<220> FEATURE:
<223> OTHER INFORMATION: synthetic peptide

<400> SEQUENCE: 2

Ala Thr Ile Met Met Gln Arg Gly Asn
1               5

<210> SEQ ID NO 3
<211> LENGTH: 78
<212> TYPE: PRT
<213> ORGANISM: artificial sequence
<220> FEATURE:
<223> OTHER INFORMATION: synthetic peptide

<400> SEQUENCE: 3

Ala Glu Ala Met Ser Gln Val Thr Asn Ser Ala Thr Ile Met Met Gln
1               5                   10                  15

Arg Gly Asn Phe Arg Asn Gln Arg Lys Ile Val Lys Cys Phe Asn Cys
            20                  25                  30

Gly Lys Glu Gly His Thr Ala Arg Asn Cys Arg Ala Pro Arg Lys Lys
        35                  40                  45

Gly Cys Trp Lys Cys Gly Lys Glu Gly His Gln Met Lys Asp Cys Thr
    50                  55                  60

Glu Arg Gln Ala Asn Ala Thr Ile Met Met Gln Arg Gly Asn
65                  70                  75

<210> SEQ ID NO 4
<211> LENGTH: 99
<212> TYPE: PRT
<213> ORGANISM: Human T-cell lymphotropic virus type 1

<400> SEQUENCE: 4

Pro Gln Val Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30

Leu Glu Glu Met Ser Leu Pro Gly Arg Trp Lys Pro Lys Met Ile Gly
        35                  40                  45

Gly Ile Gly Gly Phe Ile Lys Val Arg Gln Tyr Asp Gln Ile Leu Ile
    50                  55                  60

Glu Ile Cys Gly His Lys Ala Ile Gly Thr Val Leu Val Gly Pro Thr
65                  70                  75                  80

```
Pro Val Asn Ile Ile Gly Arg Asn Leu Leu Thr Gln Ile Gly Cys Thr
                85                  90                  95

Leu Asn Phe

<210> SEQ ID NO 5
<211> LENGTH: 99
<212> TYPE: PRT
<213> ORGANISM: Human T-cell lymphotropic virus type 1

<400> SEQUENCE: 5

Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30

Leu Glu Glu Met Asn Leu Pro Gly Arg Trp Lys Pro Lys Met Ile Gly
        35                  40                  45

Gly Ile Gly Gly Phe Ile Lys Val Arg Gln Tyr Asp Gln Ile Leu Ile
    50                  55                  60

Glu Ile Cys Gly His Lys Ala Ile Gly Thr Val Leu Val Gly Pro Thr
65                  70                  75                  80

Pro Val Asn Ile Ile Gly Arg Asn Leu Leu Thr Gln Ile Gly Cys Thr
                85                  90                  95

Leu Asn Phe

<210> SEQ ID NO 6
<211> LENGTH: 48
<212> TYPE: DNA
<213> ORGANISM: artificial sequence
<220> FEATURE:
<223> OTHER INFORMATION: artificial nucleotide

<400> SEQUENCE: 6
acgcacgcaa gcttgcggcc gcccaccatg aagctactgt cttctatc          48

<210> SEQ ID NO 7
<211> LENGTH: 45
<212> TYPE: DNA
<213> ORGANISM: artificial sequence
<220> FEATURE:
<223> OTHER INFORMATION: synthetic nucleotide

<400> SEQUENCE: 7
atagctgcgt gcgtgcgtgt cgacttactc ttttttttggg tttgg              45

<210> SEQ ID NO 8
<211> LENGTH: 39
<212> TYPE: DNA
<213> ORGANISM: artificial sequence
<220> FEATURE:
<223> OTHER INFORMATION: synthetic nucleotide

<400> SEQUENCE: 8
agctagctag cttcgcgaca cgaggcccct ttcgtcttca                    39

<210> SEQ ID NO 9
<211> LENGTH: 39
<212> TYPE: DNA
<213> ORGANISM: artificial sequence
<220> FEATURE:
<223> OTHER INFORMATION: synthetic nucleotide
```

<400> SEQUENCE: 9 cattttttttc actgcctcga gtgtacaagc tagctagct                                    39

<210> SEQ ID NO 10
<211> LENGTH: 38
<212> TYPE: DNA
<213> ORGANISM: artificial sequence
<220> FEATURE:
<223> OTHER INFORMATION: synthetic nucleotide

<400> SEQUENCE: 10
atgcatgcgg atccaccatg aagctactgt cttctatc                                     38

<210> SEQ ID NO 11
<211> LENGTH: 35
<212> TYPE: DNA
<213> ORGANISM: artificial sequence
<220> FEATURE:
<223> OTHER INFORMATION: synthetic nucleotide

<400> SEQUENCE: 11
gcatgcatgc tagcttactc ttttttttggg tttgg                                       35

<210> SEQ ID NO 12
<211> LENGTH: 38
<212> TYPE: DNA
<213> ORGANISM: artificial sequence
<220> FEATURE:
<223> OTHER INFORMATION: synthetic nucleotide

<400> SEQUENCE: 12
atcgatggat ccccaccatg gtgagcaagg gcgaggag                                     38

<210> SEQ ID NO 13
<211> LENGTH: 35
<212> TYPE: DNA
<213> ORGANISM: artificial sequence
<220> FEATURE:
<223> OTHER INFORMATION: synthetic nucleotide

<400> SEQUENCE: 13
atggacgagc tgtacaagta actcgaggat cgatc                                        35

<210> SEQ ID NO 14
<211> LENGTH: 5
<212> TYPE: PRT
<213> ORGANISM: artificial sequence
<220> FEATURE:
<223> OTHER INFORMATION: synthetic peptide

<400> SEQUENCE: 14

Arg Glu Lys Arg Ala
1               5

<210> SEQ ID NO 15
<211> LENGTH: 11
<212> TYPE: PRT
<213> ORGANISM: artificial sequence
<220> FEATURE:
<223> OTHER INFORMATION: synthetic peptide

<400> SEQUENCE: 15

Ala Lys Arg Arg Val Val Gln Arg Glu Lys Arg
1               5                   10

```
<210> SEQ ID NO 16
<211> LENGTH: 8
<212> TYPE: PRT
<213> ORGANISM: artificial sequence
<220> FEATURE:
<223> OTHER INFORMATION: synthetic peptide

<400> SEQUENCE: 16

Ala Val Gly Ile Gly Ala Leu Phe
1               5

<210> SEQ ID NO 17
<211> LENGTH: 19
<212> TYPE: PRT
<213> ORGANISM: artificial sequence
<220> FEATURE:
<223> OTHER INFORMATION: synthetic peptide

<400> SEQUENCE: 17

Ala Lys Arg Arg Val Val Gln Arg Glu Lys Arg Ala Val Gly Ile Gly
1               5                   10                  15

Ala Leu Phe

<210> SEQ ID NO 18
<211> LENGTH: 17
<212> TYPE: PRT
<213> ORGANISM: artificial sequence
<220> FEATURE:
<223> OTHER INFORMATION: synthetic peptide

<400> SEQUENCE: 18

Lys Arg Arg Val Val Gln Arg Glu Lys Arg Ala Val Gly Ile Gly Ala
1               5                   10                  15

Leu

<210> SEQ ID NO 19
<211> LENGTH: 14
<212> TYPE: DNA
<213> ORGANISM: artificial sequence
<220> FEATURE:
<223> OTHER INFORMATION: synthetic nucleotide
<220> FEATURE:
<221> NAME/KEY: misc_feature
<223> OTHER INFORMATION: X is any nucleotide
<220> FEATURE:
<221> NAME/KEY: misc_feature
<222> LOCATION: (9)..(10)
<223> OTHER INFORMATION: N is any nucleotide

<400> SEQUENCE: 19
ccaccatgnn ktga                                                     14
```

COMPOSITIONS AND METHODS FOR IDENTIFYING ENZYME AND TRANSPORT PROTEIN INHIBITORS

CROSS-REFERENCE TO RELATED APPLICATIONS

This United States utility patent application is the §371 national phase of PCT international patent application no PCT/US2010/033437, having an international filing date of May 4, 2010, which claims benefit of priority to U.S. Provisional Patent Application Ser. No. 61/175,358, filed May 4, 2009; U.S. Ser. No. 61/183,008, filed Jun. 1, 2009; U.S. Ser. No. 61/247,446, filed Sep. 30, 2001; U.S. Ser. No. 61/291,088, filed Dec. 30, 2009; U.S. Ser. No. 61/312,760, filed Mar. 11, 2010; and U.S. Ser. No. 61/312,839, filed Mar. 11, 2010. The aforementioned applications are expressly incorporated herein by reference in their entirety and for all purposes.

TECHNICAL FIELD

This invention relates to molecular and cellular biology, biochemistry, molecular genetics, and drug design and discovery. In one aspect, the invention is directed to compositions to screen for small molecule drugs that inhibit viral proteases.

BACKGROUND

Current treatments for human immunodeficiency virus (HIV) include inhibitors of HIV proteases; but these inhibitors can have severe side effects. Also, there has been a rapid emergence of HIV strains that are drug resistant, e.g., insensitive to currently used HIV inhibitors, including HIV protease inhibitors.

HIV-1 protease (PR), an aspartyl protease, is required for the efficient processing of the Gag and Gag-Pol precursor polyproteins; a critical step in the viral life cycle. For this reason, targeting PR has long been the focus of anti-retroviral therapy. However, aside from its proteolytic activity, its effects on the host cell are still unclear. Cytotoxic effects, together with instability, render expression of PR in mammalian cells difficult. Elucidating the role of PR in the viral life cycle, as well as discerning its effects on the host machinery, is vital for the design of novel therapeutic approaches.

SUMMARY

The invention provides cell-based methods for monitoring the activity of a protease, viral protease or an HIV-1 protease (PR) comprising:
(1) (a) providing a nucleic acid encoding a scaffold protein operatively linked to a transcriptional regulatory unit, wherein the scaffold protein comprises:
  (i) an amino acid motif or subsequence susceptible to cleavage by the protease, viral protease or HIV-1 protease (PR) under physiologic (cell culture) conditions;
  (ii) a transmembrane domain;
  (iii) a signal sequence or any amino acid motif that places the scaffold protein on the extracellular surface of the cell; and
  (iv) a detectable moiety,
wherein the amino acid motif or subsequence susceptible to cleavage by the protease, viral protease or HIV-1 protease (PR) is positioned within the scaffold protein such that when the detectable moiety is cleavage away from (off from) the scaffold protein by the protease, viral protease or HIV-1 protease (PR) the remaining subsequence of scaffold protein on the extracellular surface of the cell lacks the detectable moiety;
(b) providing a nucleic acid encoding the protease, viral protease or HIV-1 protease (PR) operatively linked to a transcriptional regulatory unit, or a cell that expresses a heterologous or endogenous protease, viral protease or HIV-1 protease (PR);
(c) inserting (transfecting) the nucleic acid of the invention into the cell if the cell does not already express a heterologous or endogenous protease, viral protease or HIV-1 protease (PR);
(d) co-expressing the nucleic acid of the invention in the cell, or expressing the nucleic acid of (a) in the cell if the cell already expresses a heterologous or endogenous protease, viral protease or HIV-1 protease (PR); and
(e) determining whether the scaffold protein comprising the detectable moiety is expressed on the extracellular surface of the cell,
wherein an intact scaffold protein comprising the detectable moiety is expressed on the extracellular surface of the cell when the protease, viral protease or HIV-1 protease (PR) is not enzymatically active, and an intact scaffold protein is not or is substantially less expressed on the extracellular surface of the cell when the protease, viral protease or HIV-1 protease (PR) is enzymatically active (the detectable moiety is cleaved off by the protease, viral protease or HIV-1 protease (PR));
(2) the method of (1), wherein the scaffold protein further comprises an endoplasmic reticulum (ER) retention motif or a KDEL (SEQ ID NO:1) motif,
wherein the ER retention motif or KDEL (SEQ ID NO:1) motif is positioned in the scaffold protein such that when the protease is active the scaffold will be separated into two pieces, leaving the ER retention motif-comprising or KDEL (SEQ ID NO:1) motif-comprising portion of the polypeptide in the ER and freeing the detectable moiety-comprising portion to the cell's extracellular membrane, and if the protease is blocked or inactive, the entire scaffold polypeptide will be retained in the ER, and as a consequence will not be detected on the cell's extracellular surface; or
(3) the method of (1), wherein the scaffold protein further comprises a p2/p7 recognition site imbedded in the cytoplasmic loop of the scaffold; wherein optionally the p2/p7 recognition sequence comprises or consists of ATIMMQRGN (SEQ ID NO:2), or optionally an exemplary amino-acid sequence of p2/p7 comprises AEAMSQVTNS/ ATIMMQRGN/FRNQRKIVKCFNCGKEGHTARN- CRAPRKKGCWK CGKEGHQMKDCTERQAN ATIM- MQRGN (SEQ ID NO:3).

In alternative embodiments the methods of the invention further comprise screening for an inhibitor of an HIV-1 protease (PR) by:
(a) providing a compound to be screened as an inhibitor of a protease, viral protease or HIV-1 protease (PR), or providing a nucleic acid to be screened as encoding an inhibitor of a protease, viral protease or HIV-1 protease (PR);
(b) contacting a plurality of the cells with the compound or nucleic acid of (a) either before, during and/or after the co-expressing the nucleic acid in the cell; and
(c) determining whether the scaffold protein comprising the detectable moiety is expressed on the extracellular surface of the cell, wherein an intact scaffold protein comprising the detectable moiety is expressed on the extracellular surface of the cell when the protease, viral protease or HIV-1 protease (PR) is inhibited by: the compound, a composition encoded by the nucleic acid, or a compound present in the cell only because the nucleic acid was expressed, and an intact scaffold protein is not or is substantially less expressed on the extracellular surface of the cell when the protease, viral protease or HIV-1 protease (PR) is enzymatically active (the detectable moiety is cleaved off by the protease, viral protease or HIV-1 protease (PR)) and the enzymatic activity of the protease, viral protease or HIV-1 protease (PR) is not significantly inhibited by: the compound, a composition encoded by the nucleic acid, or a compound present in the cell only because the nucleic acid was expressed.

In alternative embodiments the methods of the invention further comprise dividing the plurality of the cells co-expressing the nucleic acid of the invention in the cell and not adding the compound to be screened as an inhibitor to one of the divided cell samples.

In alternative embodiments the methods of the invention further comprise dividing the plurality of the cells co-expressing the nucleic acid of the invention in the cell and adding a known inhibitor of the HIV-1 protease (PR) to one of the divided cell samples.

In alternative embodiments, the amino acid motif or subsequence susceptible to cleavage by the protease, viral protease or HIV-1 protease (PR) under physiologic (cell culture) conditions comprises LEAQEEEEVGF (SEQ ID NO:3), or ATIMMQRGN (SEQ ID NO:2), or comprises a motif defined by and/or is definable by a protocol as described by Kurt (2003) Biophys J. 85(2):853-63; or Prabu-Jeyabalan (2002) Structure 10(3):369-81; or Prabu-Jeyabalan (2006) J. Virol. 80(7):3607-16; or Kontijevskis (2007) Proteins 68(1):305-12; or Shoeman (1991) FEBS Lett. 278 (2):199-203.

The HIV-1 protease (PR) can comprise or consist of SEQ ID NO:4 or SEQ ID NO:5, or an enzymatically active fragment thereof:

```
                                               (SEQ ID NO: 4)
PQVTLWQRPL VTIKIGGQLK EALLDTGADD TVLEEMSLPG

RWKPKMIGGI GGFIKVRQYD QILIEICGHKAIGTVLVGPT

PVNIIGRNLL TQIGCTLNF (SEQ ID NO: 5)
PQITLWQRPLVTIKIGGQLKEALLDTGADDTVLEEMNLPGRWKPKMIGGI

GGFIKVRQYDQILIEICGHKAIGTVLVGPTPVNIIGRNLLTQIGCTLNF
```

The exemplary SEQ ID NO:5 is a prototype of an NL4-3 genome, but can be used with any other sequences from other strains of HIV.

In alternative embodiments the transcriptional regulatory unit comprises a promoter, an inducible promoter or a constitutive promoter.

In alternative embodiments the cell is a mammalian cell, a monkey cell or a human cell.

In alternative embodiments the scaffold proteins of the invention comprise all or part of a mouse Lyt2 or a human CD8 polypeptide.

In alternative embodiments the detectable moiety comprises an epitope for an antibody, or a FLAG tag. The detectable moiety can be detected or measured on the extracellular surface of the cell by a high throughput screen, a flow cytometry or microscope visualization.

In alternative embodiments the compound to be screened as an inhibitor of the protease, viral protease or HIV-1 protease (PR) comprises a small molecule, a nucleic acid, a polypeptide or peptide, a peptidomimetic, a polysaccharide or a lipid.

In alternative embodiments the compound to be screened as an inhibitor of the protease, viral protease or HIV-1 protease (PR) is a member of a library of compounds to be screened, or a member of a random peptide library or a chemical compound library.

The invention provides cell-based methods for monitoring the activity of a protease comprising:

(1) (a) providing a nucleic acid encoding a scaffold protein operatively linked to a transcriptional regulatory unit, wherein the scaffold protein comprises:
  (i) an amino acid motif or subsequence susceptible to cleavage by the protease under physiologic (cell culture) conditions;
  (ii) a transmembrane domain;
  (iii) a signal sequence or any amino acid motif that places the scaffold protein on the extracellular surface of the cell; and
  (iv) a detectable moiety,
  wherein the amino acid motif or subsequence susceptible to cleavage by the protease is positioned within the scaffold protein such that when the detectable moiety is cleavage away from (off from) the scaffold protein by the protease the remaining subsequence of scaffold protein on the extracellular surface of the cell lacks the detectable moiety;

(b) providing a nucleic acid encoding the protease operatively linked to a transcriptional regulatory unit, or a cell that expresses a heterologous or endogenous protease;

(c) inserting (transfecting) the nucleic acid of the invention into the cell if the cell does not already express a heterologous or endogenous protease;

(d) co-expressing the nucleic acid of the invention in the cell, or expressing the nucleic acid of (a) in the cell if the cell already expresses a heterologous or endogenous protease; and (e) determining whether the scaffold protein comprising the detectable moiety is expressed on the extracellular surface of the cell,
wherein an intact scaffold protein comprising the detectable moiety is expressed on the extracellular surface of the cell when the protease is not enzymatically active, and an intact scaffold protein is not or is substantially less expressed on the extracellular surface of the cell when the protease is enzymatically active (the detectable moiety is cleaved off by the protease); or (2) the method of (1), wherein the scaffold protein further comprises an endoplasmic reticulum (ER) retention motif or a KDEL (SEQ ID NO:1) motif,
wherein the ER retention motif or KDEL motif is positioned in the scaffold protein such that when PR is active the scaffold will be separated into two pieces, leaving the ER retention motif-comprising or KDEL motif-comprising portion of the polypeptide in the ER and freeing the detectable moiety-comprising portion to the cell's extracellular membrane, and if PR is blocked or inactive, the entire scaffold polypeptide will be retained in the ER, and as a consequence will not be detected on the cell's extracellular surface.

In alternative embodiments the methods of the invention further comprise screening for an inhibitor of a protease by:
(a) providing a compound to be screened as an inhibitor of protease, or providing a nucleic acid to be screened as encoding an inhibitor of protease;

(b) contacting a plurality of the cells with the compound or nucleic acid of either before, during and/or after the co-expressing the nucleic acid in the cell; and (c) determining whether the scaffold protein comprising the detectable moiety is expressed on the extracellular surface of the cell, wherein an intact scaffold protein comprising the detectable moiety is expressed on the extracellular surface of the cell when the protease is inhibited by: the compound, a composition encoded by the nucleic acid, or a compound present in the cell only because the nucleic acid was expressed, and an intact scaffold protein is not or is substantially less expressed on the extracellular surface of the cell when the protease is enzymatically active (the detectable moiety is cleaved off by the protease) and the enzymatic activity of the protease is not significantly inhibited by: the compound, a composition encoded by the nucleic acid, or a compound present in the cell only because the nucleic acid was expressed.

In alternative embodiments the methods of the invention further comprise dividing the plurality of the cells co-expressing the nucleic acid of the invention in the cell and not adding the compound to be screened as an inhibitor to one of the divided cell samples.

In alternative embodiments the methods of the invention further comprise dividing the plurality of the cells co-expressing the nucleic acid of the invention in the cell and adding a known inhibitor of the protease to one of the divided cell samples.

In alternative embodiments the transcriptional regulatory unit comprises a promoter, or an inducible promoter, or a constitutive promoter.

In alternative embodiments the cell is a mammalian cell, a monkey cell or a human cell.

In alternative embodiments the scaffold proteins of the invention comprise all or part of a mouse Lyt2 or a human CD8 polypeptide.

In alternative embodiments the detectable moiety comprises an epitope for an antibody, or a FLAG tag. The detectable moiety can be detected or measured on the extracellular surface of the cell by a high throughput screen, a flow cytometry or microscope visualization.

In alternative embodiments the compound to be screened as an inhibitor of protease comprises a small molecule, a nucleic acid, a polypeptide or peptide, a peptidomimetic, a polysaccharide or a lipid. The compound to be screened can be an inhibitor of protease is a member of a library of compounds to be screened, or a member of a random peptide library or a chemical compound library.

In alternative embodiments the protease is an HIV-1 protease (PR), or the protease is a viral, a microbial or a mammalian protease.

The invention provides cell-based methods for monitoring the activity of a cell's ER and/or trans-Golgi network comprising:

(1) (a) providing a nucleic acid encoding a scaffold protein operatively linked to a transcriptional regulatory unit, wherein the scaffold protein comprises:

(i) a transmembrane domain;
(ii) a signal sequence or any amino acid motif that places the scaffold protein on the extracellular surface of the cell; and
(iii) a detectable moiety;

(b) inserting (transfecting) the scaffold protein-encoding nucleic acid of (a) into the cell;

(d) expressing the nucleic acid of (a); and (e) determining whether the scaffold protein comprising the detectable moiety is expressed on the extracellular surface of the cell, wherein the scaffold protein is expressed on the extracellular surface of the cell when the activity of the cell's ER and trans-Golgi network is functioning; or (2) the method of (1), wherein the scaffold protein further comprises an endoplasmic reticulum (ER) retention motif or a KDEL motif, wherein the ER retention motif or KDEL motif is positioned in the scaffold protein such that when PR is active the scaffold will be separated into two pieces, leaving the ER retention motif-comprising or KDEL motif-comprising portion of the polypeptide in the ER and freeing the detectable moiety-comprising portion to the cell's extracellular membrane, and if PR is blocked or inactive, the entire scaffold polypeptide will be retained in the ER, and as a consequence will not be detected on the cell's extracellular surface.

In alternative embodiments the methods of the invention further comprise screening for an inhibitor of the cell's ER and trans-Golgi network by:

(a) providing a compound or nucleic acid to be screened as an inhibitor of the cell's ER and trans-Golgi network;

(b) contacting a plurality of the cells with the compound or nucleic acid of (a) either before, during and/or after the co-expressing the nucleic acid of the invention in the cell; and (c) determining whether the scaffold protein comprising the detectable moiety is expressed on the extracellular surface of the cell, wherein an intact scaffold protein comprising the detectable moiety is expressed (or is substantially expressed) on the extracellular surface of the cell when the cell's ER and trans-Golgi network is not inhibited.

In alternative embodiments the methods of the invention further comprise dividing the plurality of the cells co-expressing the nucleic acid of the invention in the cell and not adding the compound to be screened as an inhibitor to one of the divided cell samples.

In alternative embodiments the methods of the invention further comprise running a positive control comprising dividing the plurality of the cells co-expressing the nucleic acid in the cell and adding a known inhibitor of the cell's ER and/or trans-Golgi network to one of the divided cell samples.

In alternative embodiments the transcriptional regulatory unit comprises a promoter, an inducible promoter or a constitutive promoter.

In alternative embodiments the cell is a mammalian cell, a monkey cell or a human cell.

In alternative embodiments the scaffold proteins of the invention comprise all or part of a mouse Lyt2 or a human CD8 polypeptide.

In alternative embodiments the detectable moiety comprises an epitope for an antibody, or a FLAG tag. The detectable moiety can be detected or measured on the extracellular surface of the cell by a high throughput screen, a flow cytometry or microscope visualization.

In alternative embodiments the compound to be screened as an inhibitor of protease comprises a small molecule, a nucleic acid, a polypeptide or peptide, a peptidomimetic, a polysaccharide or a lipid. In alternative embodiments the compound to be screened as an inhibitor of protease is a member of a library of compounds to be screened, or a member of a random peptide library or a chemical compound library.

In alternative embodiments the protease is an HIV-1 protease (PR). The protease can be a viral, a microbial or a mammalian protease.

The invention provides isolated, recombinant or synthetic nucleic acids encoding a scaffold protein operatively linked to a transcriptional regulatory unit, wherein the scaffold protein comprises:

(a) (i) an amino acid motif or subsequence susceptible to cleavage by a protease under physiologic (cell culture) conditions;

(ii) a transmembrane domain;

(iii) a signal sequence or any amino acid motif that places the scaffold protein on the extracellular surface of the cell; and (iv) a detectable moiety; or (b) the nucleic acid of (a), wherein the scaffold protein further comprises an endoplasmic reticulum (ER) retention motif or a KDEL motif, wherein the ER retention motif or KDEL motif is positioned in the scaffold protein such that when PR is active the scaffold will be separated into two pieces, leaving the ER retention motif-comprising or KDEL motif-comprising portion of the polypeptide in the ER and freeing the detectable moiety-comprising portion to the cell's extracellular membrane, and if PR is blocked or inactive, the entire scaffold polypeptide will be retained in the ER, and as a consequence will not be detected on the cell's extracellular surface.

In alternative embodiments the protease is an HIV-1 protease (PR), or the protease is a viral, a microbial or a mammalian protease.

In alternative embodiments the scaffold proteins of the invention comprise all or part of a mouse Lyt2 or a human CD8 polypeptide.

In alternative embodiments the detectable moiety comprises an epitope for an antibody, or a FLAG tag.

The invention provides vectors, expression cassettes, cosmids or plasmids comprising the isolated, recombinant or synthetic nucleic acids of the invention, and cells comprising any one, several or all of these embodiments.

The invention provides isolated, recombinant or synthetic polypeptides, e.g., the so-called "scaffold proteins" of the invention, encoded by a nucleic acid of the invention.

The invention provides cells comprising the isolated, recombinant or synthetic nucleic acid of the invention, the vector, expression cassette, cosmid or plasmid of the invention, or isolated, recombinant or synthetic polypeptide of the invention.

A chimeric (e.g., recombinant) polypeptide comprising:

(i) an amino acid motif or subsequence susceptible to cleavage by the HIV-1 protease (PR) under physiologic (cell culture) conditions;

(ii) a transmembrane domain;

(iii) a signal sequence or any amino acid motif that places the scaffold protein on the extracellular surface of the cell; and (iv) a detectable moiety, wherein the amino acid motif or subsequence susceptible to cleavage by the HIV-1 protease (PR) is positioned within the scaffold protein such that when the detectable moiety is cleavage away from (off from) the scaffold protein by the HIV-1 protease (PR) the remaining subsequence of scaffold protein on the extracellular surface of the cell lacks the detectable moiety;

(2) the chimeric polypeptide of (1), wherein the scaffold protein further comprises an endoplasmic reticulum (ER) retention motif or a KDEL motif, wherein the ER retention motif or KDEL motif is positioned in the scaffold protein such that when PR is active the scaffold will be separated into two pieces, leaving the ER retention motif-comprising or KDEL motif-comprising portion of the polypeptide in the ER and freeing the detectable moiety-comprising portion to the cell's extracellular membrane, and if PR is blocked or inactive, the entire scaffold polypeptide will be retained in the ER, and as a consequence will not be detected on the cell's extracellular surface; or (3) the chimeric polypeptide of (1), wherein the scaffold protein further comprises a p2/p7 recognition site imbedded in the cytoplasmic loop of the scaffold, wherein optionally the p2/p7 recognition sequence comprises or consists of ATIMMQRGN (SEQ ID NO:2), or optionally an exemplary amino-acid sequence of p2/p7 comprises AEAMSQVTNS/ATIMMQRGN/FRNQRKIVKCFNCGKEGHTARNCRAPRKKGCWK CGKEGHQMKDCTERQAN ATIMMQRGN (SEQ ID NO:3).

A chimeric (e.g., recombinant) polypeptide comprising:

(i) an amino acid motif or subsequence susceptible to cleavage by the protease under physiologic (cell culture) conditions;

(ii) a transmembrane domain;

(iii) a signal sequence or any amino acid motif that places the scaffold protein on the extracellular surface of the cell; and (iv) a detectable moiety, wherein the amino acid motif or subsequence susceptible to cleavage by the protease is positioned within the scaffold protein such that when the detectable moiety is cleavage away from (off from) the scaffold protein by the protease the remaining subsequence of scaffold protein on the extracellular surface of the cell lacks the detectable moiety; or (2) the chimeric polypeptide of (1), wherein the scaffold protein further comprises an endoplasmic reticulum (ER) retention motif or a KDEL (SEQ ID NO:1) motif, wherein the ER retention motif or KDEL motif is positioned in the scaffold protein such that when PR is active the scaffold will be separated into two pieces, leaving the ER retention motif-comprising or KDEL motif-comprising portion of the polypeptide in the ER and freeing the detectable moiety-comprising portion to the cell's extracellular membrane, and if PR is blocked or inactive, the entire scaffold polypeptide will be retained in the ER, and as a consequence will not be detected on the cell's extracellular surface.

A chimeric (e.g., recombinant) polypeptide comprising:

(i) a transmembrane domain;

(ii) a signal sequence or any amino acid motif that places the scaffold protein on the extracellular surface of the cell; and (iii) a detectable moiety; or (2) the chimeric polypeptide of (1), wherein the scaffold protein further comprises an endoplasmic reticulum (ER) retention motif or a KDEL (SEQ ID NO:1) motif, wherein the ER retention motif or KDEL motif is positioned in the scaffold protein such that when PR is active the scaffold will be separated into two pieces, leaving the ER retention motif-comprising or KDEL motif-comprising portion of the polypeptide in the ER and freeing the detectable moiety-comprising portion to the cell's extracellular membrane, and if PR is blocked or inactive, the entire scaffold polypeptide will be retained in the ER, and as a consequence will not be detected on the cell's extracellular surface.

In one embodiment, assays and cells of the invention can be used to identify whether or not a viral protease (PR) is active. This is based on the detection of a tag on the surface of a mammalian cell, e.g., a human cell. If PR is active, no tag will be detected. If PR is inactive or blocked, the tag will appear on the surface of the cell. This can be easily recognized with antibodies that are coupled to a fluorescent dye through a technique referred to as flow cytometry. As a result, analysis of various drugs on the expression of the tag on the surface of the cell can be conducted. If the drug inhibits or blocks PR, the cells will become positive for tag surface expression. In contrast, if the drug is not active against PR, the cells will be negative for tag expression.

In one embodiment, assays and cells of the invention rely on the engineering of a recombinant polypeptide, the so-called "scaffold protein". In one embodiment, this scaffold is referred to as p2/7; which is one of the natural targets of PR, and PR cleaves it at the boundary between p2 and p7 during normal HIV-1 infection. PR is essential for the viral lifecycle.

Drugs against PR can hinder its capacity to cleave its targets, resulting in inhibitory effects on viral replication. Thus, in some embodiments of this invention a p2/p7 scaffold is engineered in such a way that instead of being expressed inside the cell, it is expressed on the surface of the cell. To achieve surface expression, a "scaffold protein" such as the exemplary p2/p7 is fused to a signal (e.g., signal sequence) that directs it to the cell surface. Addition of another segment; a transmembrane domain (or motif), allows it to become incorporated into the cell surface. A marker (tag) is added to the p2/p7 scaffold to allow detection of its presence on the surface.

In one embodiment, assays and cells of the invention are adapted to a high throughput system, where they can be used e.g., in the search of much needed novel drugs against PR.

In alternative embodiments, methods of the invention are practiced in vitro or in vivo. For example, the cells need not be intact for membrane analysis of the presence or absence of detectable moieties.

In alternative embodiments, the invention provides cell-based methods (e.g., wherein the cell is a lymphocyte, such as a T cell, e.g., a CD4$^+$ cell) for monitoring the activity of an enzyme, e.g., a protease, e.g., an HIV protease, e.g., an HIV-1 protease (PR), or an NS2/NS3 or NS3/NS4A protease of hepatitis C virus, or HCV), comprising:

(1) (a) providing a nucleic acid encoding a scaffold protein operatively linked to a transcriptional regulatory unit, wherein the scaffold protein comprises:
  (i) an amino acid motif or subsequence susceptible to cleavage by the enzyme, e.g., a protease, e.g., an HIV protease, e.g., an HIV-1 protease (PR), or an NS2/NS3 or NS3/NS4A protease of hepatitis C virus, under physiologic (e.g., cell culture) conditions;
  (ii) a transmembrane domain;
  (iii) a signal sequence or any amino acid motif that places the scaffold protein on the extracellular surface of the cell; and
  (iv) a detectable moiety (e.g., a Green Fluorescent Protein (GFP) or a luciferase, or any compound that can be directly or indirectly detected),
  wherein in alternative embodiments the amino acid motif or subsequence susceptible to cleavage by the enzyme, e.g., the protease, e.g., HIV protease, e.g., HIV-1 protease (PR), or an NS2/NS3 or NS3/NS4A HCV protease, is positioned within the scaffold protein such that when the detectable moiety (e.g., Green Fluorescent Protein (GFP) or luciferase) is cleaved away from (off from) the scaffold protein by the enzyme, e.g., protease, e.g., HIV protease, e.g., HIV-1 protease (PR), or an NS2/NS3 or NS3/NS4A HCV protease, and the remaining subsequence of scaffold protein on the extracellular surface of the cell lacks the detectable moiety;

(b) providing a nucleic acid encoding the enzyme, e.g., the protease, e.g., HIV protease, e.g., HIV-1 protease (PR), or NS2/NS3 or NS3/NS4A HCV protease, operatively linked to a transcriptional regulatory unit, or a cell that expresses a heterologous or endogenous enzyme, e.g., protease, e.g., HIV protease, e.g., HIV-1 protease (PR);

(c) inserting (transfecting) the nucleic acid of step (b) (e.g., comprising a nucleic acid encoding the enzyme, e.g., the protease, e.g., HIV protease, e.g., HIV-1 protease) into the cell (e.g., a lymphocyte, such as a T cell, e.g., a CD4$^+$ cell) if the cell does not already express a heterologous or endogenous enzyme, e.g., protease, e.g., HIV protease, e.g., HIV-1 protease (PR));

(d) co-expressing the nucleic acid of step (a) and (b) in the cell, or expressing the nucleic acid of (a) in the cell if the cell already expresses a heterologous or endogenous HIV-1 protease (PR); and (e) determining whether the scaffold protein comprising the detectable moiety (e.g., a Green Fluorescent Protein (GFP) or a luciferase) is expressed on the extracellular surface of the cell (e.g., by flow cytometry or any high-throughput assay), wherein in alternative embodiments an intact scaffold protein comprising the detectable moiety is expressed on the extracellular surface of the cell when the enzyme, e.g., protease, e.g., HIV protease, e.g., HIV-1 protease (PR), or NS2/NS3 or NS3/NS4A HCV protease, is not enzymatically active, and an intact scaffold protein is not or is substantially less expressed on the extracellular surface of the cell when the enzyme, e.g., protease, e.g., HIV protease, e.g., HIV-1 protease (PR), or NS2/NS3 or NS3/NS4A HCV protease, is enzymatically active (the detectable moiety is cleaved off by the enzyme, e.g., protease, e.g., HIV protease, e.g., HIV-1 protease (PR), or NS2/NS3 or NS3/NS4A HCV protease);

(2) the method of (1), wherein the scaffold protein further comprises an endoplasmic reticulum (ER) retention motif or a KDEL motif, wherein in alternative embodiments the ER retention motif or KDEL motif is positioned in the scaffold protein such that when enzyme, e.g., protease, e.g., HIV protease, e.g., HIV-1 protease (PR), or NS2/NS3 or NS3/NS4A HCV protease, is active the scaffold will be separated into two pieces, leaving the ER retention motif-comprising or KDEL motif-comprising portion of the polypeptide in the ER and freeing the detectable moiety-comprising portion to the cell's extracellular membrane, and if the enzyme, e.g., protease, e.g., HIV protease, e.g., HIV-1 protease (PR), or NS2/NS3 or NS3/NS4A HCV protease, is blocked or inactive, the entire scaffold polypeptide will be retained in the ER, and as a consequence will not be detected on the cell's extracellular surface; or (3) the method of (1), wherein the scaffold protein further comprises a p2/p7 recognition site imbedded in the cytoplasmic loop of the scaffold; wherein optionally the p2/p7 recognition sequence comprises or consists of ATIM-MQRGN (SEQ ID NO:2), or optionally an exemplary amino-acid sequence of p2/p7 comprises AEAMSQVTNS/ ATIMMQRGN/FRNQRKIVKCFNCGKEGHTARN-CRAPRKKGCWK CGKEGHQMKDCTERQAN ATIM-MQRGN (SEQ ID NO:3).

In alternative embodiments the methods of the invention further comprise screening for an inhibitor of an enzyme, e.g., protease, e.g., HIV protease, e.g., HIV-1 protease (PR) by:

(a) providing a compound to be screened as an inhibitor of an enzyme, e.g., protease, e.g., HIV protease, e.g., HIV-1 protease (PR), or NS2/NS3 or NS3/NS4A HCV protease, or providing a nucleic acid to be screened as encoding an inhibitor of an enzyme, e.g., protease, e.g., HIV protease, e.g., HIV-1 protease (PR), or NS2/NS3 or NS3/NS4A HCV protease;

(b) contacting a plurality of the cells (e.g., lymphocytes, such as T cells, e.g., CD4+ cells) with the compound or nucleic acid of (a) either before, during and/or after the co-expressing the nucleic acid in the cell; and (c) determining whether the scaffold protein comprising the detectable moiety (e.g., a Green Fluorescent Protein (GFP) or a luciferase) is expressed on the extracellular surface of the cell (e.g., by flow cytometry or any high-throughput assay), wherein in alternative embodiments an intact scaffold protein comprising the detectable moiety is expressed on the extracellular surface of the cell when the enzyme, e.g., protease, e.g., HIV protease, e.g., HIV-1 protease (PR), or NS2/NS3 or NS3/NS4A HCV protease, is inhibited by: the compound, a composition encoded by the nucleic acid, or a compound present in the cell only because the nucleic acid was expressed, and an intact scaffold protein is not or is substantially less expressed (in quantitative terms) on the extracellular surface of the cell when the enzyme, e.g., protease, e.g., HIV protease, e.g., HIV-1 protease (PR), or NS2/NS3 or NS3/NS4A HCV protease, is enzymatically active; for example, in one embodiment the detectable moiety is cleaved off by the enzyme, e.g., protease, e.g., HIV protease, e.g., HIV-1 protease (PR), or NS2/NS3 or NS3/NS4A HCV protease, and the enzymatic activity of the enzyme, e.g., protease, e.g., HIV protease, e.g., HIV-1 protease (PR), or NS2/NS3 or NS3/NS4A HCV protease, is not significantly inhibited by: the compound, a composition encoded by the nucleic acid or a compound present in the cell only because the nucleic acid was expressed.

In alternative embodiments the methods of the invention further comprise dividing the plurality of the cells co-expressing the nucleic acid or nucleic acids in the cell (e.g., as noted above, co-expressing the nucleic acid of step (a) and (b) in the cell, or expressing the nucleic acid of (a) in the cell if the cell already expresses a heterologous or endogenous enzyme, e.g., protease, e.g., HIV protease, e.g., HIV-1 protease (PR), or NS2/NS3 or NS3/NS4A HCV protease, and not adding the compound to be screened as an inhibitor to one of the divided cell samples.

In alternative embodiments the methods of the invention further comprise dividing the plurality of the cells co-expressing the nucleic acid or nucleic acids in the cell (e.g., as noted above, co-expressing the nucleic acid of step (a) and (b) in the cell, or expressing the nucleic acid of (a) in the cell if the cell already expresses a heterologous or endogenous HIV-1 protease) and adding a known inhibitor of the enzyme, e.g., protease, e.g., HIV protease, e.g., HIV-1 protease (PR), or NS2/NS3 or NS3/NS4A HCV protease, to one of the divided cell samples.

In alternative embodiments, the amino acid motif or subsequence susceptible to cleavage by the enzyme, e.g., protease, e.g., HIV protease, e.g., HIV-1 protease (PR), under physiologic (cell culture) conditions comprises LEAQEEEEVGF (SEQ ID NO:3), or ATIMMQRGN (SEQ ID NO:2), or comprises a motif defined by and/or is definable by a protocol as described by Kurt (2003) Biophys J. 85(2):853-63; or Prabu-Jeyabalan (2002) Structure 10(3):369-81; or Prabu-Jeyabalan (2006) J. Virol. 80(7):3607-16; or Kontijevskis (2007) Proteins 68(1):305-12; or Shoeman (1991) FEBS Lett. 278(2):199-203.

The HIV-1 protease (PR) can comprise or consist of SEQ ID NO:4 or SEQ ID NO:5, or an enzymatically active fragment thereof:

```
                                          (SEQ ID NO: 4)
PQVTLWQRPL VTIKIGGQLK EALLDTGADD TVLEEMSLPG

RWKPKMIGGI GGFIKVRQYD QILIEICGHKAIGTVLVGPT

PVNIIGRNLL TQIGCTLNF (SEQ ID NO: 5)
PQITLWQRPLVTIKIGGQLKEALLDTGADDTVLEEMNLPGRWKPKMIGGI

GGFIKVRQYDQILIEICGHKAIGTVLVGPTPVNIIGRNLLTQIGCTLNF
```

The exemplary SEQ ID NO:5 is a prototype of an NL4-3 genome, but can be used with any other sequences from other strains of HIV.

In alternative embodiments the transcriptional regulatory unit comprises a promoter, an inducible promoter or a constitutive promoter.

In alternative embodiments the cell is a mammalian cell, a monkey cell or a human cell, or the cell is a lymphocyte such as a T cell, e.g., a CD4' or CD8' cell.

In alternative embodiments the scaffold proteins of the invention comprise all or part of a mouse Lyt2 or a human CD8 polypeptide.

In alternative embodiments the detectable moiety comprises an epitope for an antibody, or a FLAG tag. The detectable moiety can be detected or measured on the extracellular surface of the cell by a high throughput screen, a flow cytometry or microscope visualization.

In alternative embodiments the compound to be screened as an inhibitor of enzyme, e.g., protease, e.g., HIV protease, e.g., HIV-1 protease (PR), or NS2/NS3 or NS3/NS4A HCV protease, comprises a small molecule, a nucleic acid, a polypeptide or peptide, a peptidomimetic, a polysaccharide or a lipid.

In alternative embodiments the compound to be screened as an inhibitor of enzyme, e.g., protease, e.g., HIV protease, e.g., HIV-1 protease (PR), or NS2/NS3 or NS3/NS4A HCV protease, is a member of a library of compounds (e.g., a peptide library) to be screened, or a member of a random peptide library or a chemical compound library.

The invention provides cell-based methods (e.g., wherein the cell is a lymphocyte, such as a T cell, e.g., a CD4 cell) for monitoring the activity of a protease comprising:

(1) (a) providing a nucleic acid encoding a scaffold protein operatively linked to a transcriptional regulatory unit, wherein the scaffold protein comprises:
  (i) an amino acid motif or subsequence susceptible to cleavage by the protease under physiologic (cell culture) conditions;
  (ii) a transmembrane domain;
  (iii) a signal sequence or any amino acid motif that places the scaffold protein on the extracellular surface of the cell; and
  (iv) a detectable moiety (e.g., a Green Fluorescent Protein (GFP) or a luciferase, or any compound that can be directly or indirectly detected),
  wherein in alternative embodiments the amino acid motif or subsequence susceptible to cleavage by the protease is positioned within the scaffold protein such that when the detectable moiety is cleaved away from (off from) the scaffold protein by the protease the remaining subsequence of scaffold protein on the extracellular surface of the cell lacks the detectable moiety;

(b) providing a nucleic acid encoding the protease operatively linked to a transcriptional regulatory unit, or a cell that expresses a heterologous or endogenous protease;

(c) inserting (transfecting) the nucleic acid of (b) into the cell if the cell does not already express a heterologous or endogenous protease;

(d) co-expressing the nucleic acid of (a) and (b) in the cell, or expressing the nucleic acid of (a) in the cell if the cell already expresses a heterologous or endogenous protease; and (e) determining whether the scaffold protein comprising the detectable moiety is expressed on the extracellular surface of the cell (e.g., by flow cytometry or any high-throughput assay), wherein in alternative embodiments an intact scaffold protein comprising the detectable moiety is expressed on the extracellular surface of the cell when the protease is not enzymatically active, and an intact scaffold protein is not or is substantially less expressed on the extracellular surface of the cell when the protease is enzymatically active (the detectable moiety is cleaved off by the protease); or (2) the method of (1), wherein the scaffold protein further comprises an endoplasmic reticulum (ER) retention motif or a KDEL motif, wherein in alternative embodiments the ER retention motif or KDEL motif is positioned in the scaffold protein such that when PR is active the scaffold will be separated into two pieces, leaving the ER retention motif-comprising or KDEL motif-comprising portion of the polypeptide in the ER and freeing the detectable moiety-comprising portion to the cell's extracellular membrane, and if PR is blocked or inactive, the entire scaffold polypeptide will be retained in the ER, and as a consequence will not be detected on the cell's extracellular surface.

In alternative embodiments the methods of the invention further comprise screening for an inhibitor of a protease by:

(a) providing a compound to be screened as an inhibitor of protease, or providing a nucleic acid to be screened as encoding an inhibitor of protease;

(b) contacting a plurality of the cells with the compound or nucleic acid of either before, during and/or after the co-expressing the nucleic acid in the cell; and (c) determining whether the scaffold protein comprising the detectable moiety is expressed on the extracellular surface of the cell (e.g., by flow cytometry or any high-throughput assay), wherein in alternative embodiments an intact scaffold protein comprising the detectable moiety is expressed on the extracellular surface of the cell when the protease is inhibited by: the compound, a composition encoded by the nucleic acid, or a compound present in the cell only because the nucleic acid was expressed, and an intact scaffold protein is not or is substantially less expressed on the extracellular surface of the cell when the protease is enzymatically active (the detectable moiety is cleaved off by the protease) and the enzymatic activity of the protease is not significantly inhibited by: the compound, a composition encoded by the nucleic acid, or a compound present in the cell only because the nucleic acid was expressed.

In alternative embodiments the methods of the invention further comprise dividing the plurality of the cells co-expressing the nucleic acid or nucleic acids (e.g., as noted above, co-expressing the nucleic acid of step (a) and (b) in the cell, or expressing the nucleic acid of (a) in the cell if the cell already expresses a heterologous or endogenous HIV-1 protease) and not adding the compound to be screened as an inhibitor to one of the divided cell samples.

In alternative embodiments the methods of the invention further comprise dividing the plurality of the cells co-expressing the nucleic acid or nucleic acids in the cell and adding a known inhibitor of the protease to one of the divided cell samples.

In alternative embodiments the transcriptional regulatory unit comprises a promoter, or an inducible promoter, or a constitutive promoter.

In alternative embodiments the cell is a mammalian cell, a monkey cell or a human cell.

In alternative embodiments the scaffold proteins of the invention comprise all or part of a mouse Lyt2 or a human CD8 polypeptide.

In alternative embodiments the detectable moiety comprises an epitope for an antibody, or a FLAG tag. The detectable moiety can be detected or measured on the extracellular surface of the cell by a high throughput screen, a flow cytometry or microscope visualization.

In alternative embodiments the compound to be screened as an inhibitor of protease comprises a small molecule, a nucleic acid, a polypeptide or peptide, a peptidomimetic, a polysaccharide or a lipid. The compound to be screened can be an inhibitor of protease is a member of a library of compounds to be screened, or a member of a random peptide library or a chemical compound library.

In alternative embodiments the protease is an HIV-1 protease (PR), or the protease is a viral, a microbial or a mammalian protease.

The invention provides cell-based methods for monitoring the activity of a cell's (e.g., a lymphocyte, such as a T cell, e.g., a CD4$^+$ cell) ER and/or trans-Golgi network or a cell's ER and/or monitoring the activity of a cell's ER and/or trans-Golgi transport proteins, comprising:

(1) (a) providing a nucleic acid encoding a scaffold protein operatively linked to a transcriptional regulatory unit, wherein the scaffold protein comprises:
 (i) a transmembrane domain;
 (ii) a signal sequence or any amino acid motif that places the scaffold protein on the extracellular surface of the cell; and
 (iii) a detectable moiety (e.g., a Green Fluorescent Protein (GFP) or a luciferase, or any compound that can be directly or indirectly detected);

(b) inserting (transfecting) the scaffold protein-encoding nucleic acid of (a) into the cell;

(d) expressing the nucleic acid of (a); and (e) determining whether the scaffold protein comprising the detectable moiety is expressed on the extracellular surface of the cell (e.g., by flow cytometry or any high-throughput assay), wherein in alternative embodiments the scaffold protein is expressed on the extracellular surface of the cell when the activity of the cell's ER and trans-Golgi network is functioning; or (2) the method of (1), wherein the scaffold protein further comprises an endoplasmic reticulum (ER) retention motif or a KDEL motif, wherein in alternative embodiments the ER retention motif or KDEL motif is positioned in the scaffold protein such that when PR is active the scaffold will be separated into two pieces, leaving the ER retention motif-comprising or KDEL motif-comprising portion of the polypeptide in the ER and freeing the detectable moiety-comprising portion to the cell's extracellular membrane, and if PR is blocked or inactive, the entire scaffold polypeptide will be retained in the ER, and as a consequence will not be detected on the cell's extracellular surface.

In alternative embodiments the methods of the invention further comprise screening for an inhibitor of the cell's ER and trans-Golgi network by:

(a) providing a compound or nucleic acid to be screened as an inhibitor of the cell's ER and trans-Golgi network;

(b) contacting a plurality of the cells with the compound or nucleic acid of (a) either before, during and/or after the co-expressing the nucleic acid of the invention in the cell; and (c) determining whether the scaffold protein comprising the detectable moiety is expressed on the extracellular surface of the cell, wherein an intact scaffold protein comprising the detectable moiety is expressed (or is substantially expressed) on the extracellular surface of the cell when the cell's ER and trans-Golgi network is not inhibited.

In alternative embodiments the methods of the invention further comprise dividing the plurality of the cells co-expressing the nucleic acid of the invention in the cell and not adding the compound to be screened as an inhibitor to one of the divided cell samples.

In alternative embodiments the methods of the invention further comprise running a positive control comprising dividing the plurality of the cells co-expressing the nucleic acid in the cell and adding a known inhibitor of the cell's ER and/or trans-Golgi network to one of the divided cell samples.

In alternative embodiments the transcriptional regulatory unit comprises a promoter, an inducible promoter or a constitutive promoter.

In alternative embodiments the cell is a mammalian cell, a monkey cell or a human cell.

In alternative embodiments the scaffold proteins of the invention comprise all or part of a mouse Lyt2 or a human CD8 polypeptide.

In alternative embodiments the detectable moiety comprises an epitope for an antibody, or a FLAG tag. The detectable moiety can be detected or measured on the extracellular surface of the cell by a high throughput screen, a flow cytometry or microscope visualization.

In alternative embodiments the compound to be screened as an inhibitor of protease comprises a small molecule, a nucleic acid, a polypeptide or peptide, a peptidomimetic, a polysaccharide or a lipid. In alternative embodiments the compound to be screened as an inhibitor of protease is a member of a library of compounds to be screened, or a member of a random peptide library or a chemical compound library.

In alternative embodiments the enzyme, e.g., protease, is an HIV enzyme, e.g., an HIV-1 protease (PR), or a hepatitis enzyme, e.g., an NS2/NS3 or NS3/NS4A HCV protease. The protease can be a viral, a microbial or a mammalian enzyme, e.g., a protease. The viral enzyme, e.g., protease, can be any retroviral enzyme, lentiviral enzyme, HIV enzyme, hepatitis enzyme or any viral protease or other enzyme.

The invention provides isolated, recombinant or synthetic nucleic acids encoding a scaffold or other structural protein operatively linked to a transcriptional regulatory unit, wherein the scaffold or other structural protein comprises:

(a) (i) an amino acid motif or subsequence susceptible to cleavage by an enzyme, e.g., a protease, under physiologic (cell culture) conditions;

(ii) a transmembrane domain;

(iii) a signal sequence or any amino acid motif that places the scaffold protein on the extracellular surface of the cell; and (iv) a detectable moiety (e.g., a Green Fluorescent Protein (GFP) or a luciferase, or any compound that can be directly or indirectly detected); or (b) the nucleic acid of (a), wherein the scaffold or other structural protein further comprises an endoplasmic reticulum (ER) retention motif or a KDEL motif, wherein in alternative embodiments the ER retention motif or KDEL motif is positioned in the scaffold or other structural protein such that when enzyme, e.g., protease or PR, is active the scaffold will be separated into two pieces, leaving the ER retention motif-comprising or KDEL motif-comprising portion of the polypeptide in the ER and freeing the detectable moiety-comprising portion to the cell's extracellular membrane, and if the enzyme, e.g., protease or PR, is blocked or inactive, the entire scaffold polypeptide will be retained in the ER, and as a consequence will not be detected on the cell's extracellular surface.

In alternative embodiments the enzyme is a protease, e.g., an HIV-1 protease (PR), or the protease is a viral, a microbial or a mammalian protease.

In alternative embodiments the scaffold proteins comprise all or part of a mouse Lyt2 or a human CD8 polypeptide.

In alternative embodiments the detectable moiety comprises an epitope for an antibody, or a FLAG tag.

The invention provides vectors, expression cassettes, cosmids or plasmids comprising the isolated, recombinant or synthetic nucleic acids or the invention or used to practice this invention, and cells comprising any one, several or all of these embodiments.

The invention provides isolated, recombinant or synthetic polypeptides, e.g., the so-called "scaffold proteins" of the invention, encoded by a nucleic acid of the invention.

The invention provides cells comprising the isolated, recombinant or synthetic nucleic acid of the invention, the vector, expression cassette, cosmid or plasmid of the invention, or isolated, recombinant or synthetic polypeptide of the invention.

A chimeric (e.g., recombinant) polypeptide comprising:

(i) an amino acid motif or subsequence susceptible to cleavage by an enzyme, e.g., a protease or an HIV-1 protease (PR), or an NS2/NS3 or NS3/NS4A protease of HCV, under physiologic (cell culture) conditions;

(ii) a transmembrane domain;

(iii) a signal sequence or any amino acid motif that places the scaffold protein on the extracellular surface of the cell; and (iv) a detectable moiety (e.g., a Green Fluorescent Protein (GFP) or a luciferase, or any compound that can be directly or indirectly detected), wherein in alternative embodiments the amino acid motif or subsequence susceptible to cleavage by the enzyme, e.g., protease or HIV-1 protease (PR), or an NS2/NS3 or NS3/NS4A protease of HCV, is positioned within the scaffold protein such that when the detectable moiety is cleaved away from (off from) the scaffold protein by the enzyme, e.g., protease or HIV-1 protease (PR), or an NS2/NS3 or NS3/NS4A protease of HCV, the remaining subsequence of scaffold protein on the extracellular surface of the cell lacks the detectable moiety;

(2) the chimeric polypeptide of (1), wherein the scaffold protein further comprises an endoplasmic reticulum (ER) retention motif or a KDEL motif, wherein in alternative embodiments the ER retention motif or KDEL motif is positioned in the scaffold protein such that when the enzyme, e.g., protease or HIV-1 protease (PR), or an NS2/NS3 or NS3/NS4A protease of HCV, is active the scaffold will be separated into two pieces, leaving the ER retention motif-comprising or KDEL motif-comprising portion of the polypeptide in the ER and freeing the detectable moiety-comprising portion to the cell's extracellular membrane, and if the enzyme, e.g., protease or HIV-1 protease (PR), or an NS2/NS3 or NS3/NS4A protease of HCV, is blocked or inactive, the entire scaffold polypeptide will be retained in the ER, and as a consequence will not be detected on the cell's extracellular surface; or (3) the chimeric polypeptide of (1), wherein the scaffold protein further comprises a p2/p7 recognition site imbedded in the cytoplasmic loop of the scaffold, wherein in alternative embodiments the p2/p7 recognition sequence comprises or consists of ATIMMQRGN (SEQ ID NO:2), or optionally an exemplary amino-acid sequence of p2/p7 comprises AEAMSQVTNS/ATIMMQRGN/FRN-QRKIVKCFNCGKEGHTARNCRAPRKKGCWK CGKEGHQMKDCTERQAN ATIMMQRGN (SEQ ID NO:3).

A chimeric (e.g., recombinant) polypeptide comprising:
(i) an amino acid motif or subsequence susceptible to cleavage by an enzyme, e.g., protease or HIV-1 protease (PR), or an NS2/NS3 or NS3/NS4A protease of HCV, under physiologic (cell culture) conditions;
(ii) a transmembrane domain;
(iii) a signal sequence or any amino acid motif that places the scaffold protein on the extracellular surface of the cell; and
(iv) a detectable moiety (e.g., a Green Fluorescent Protein (GFP) or a luciferase, or any compound that can be directly or indirectly detected), wherein in alternative embodiments the amino acid motif or subsequence susceptible to cleavage by the enzyme, e.g., protease or HIV-1 protease (PR), or NS2/NS3 or NS3/NS4A protease of HCV, is positioned within the scaffold protein such that when the detectable moiety is cleaved away from (off from) the scaffold protein by the enzyme, e.g., protease or HIV-1 protease (PR), or NS2/NS3 or NS3/NS4A protease of HCV, the remaining subsequence of scaffold protein on the extracellular surface of the cell lacks the detectable moiety; or (2) the chimeric polypeptide of (1), wherein the scaffold protein further comprises an endoplasmic reticulum (ER) retention motif or a KDEL motif, wherein in alternative embodiments the ER retention motif or KDEL motif is positioned in the scaffold protein such that when the enzyme, e.g., protease or HIV-1 protease (PR), or NS2/NS3 or NS3/NS4A protease of HCV, is active the scaffold will be separated into two pieces, leaving the ER retention motif-comprising or KDEL motif-comprising portion of the polypeptide in the ER and freeing the detectable moiety-comprising portion to the cell's extracellular membrane, and if the enzyme, e.g., protease or HIV-1 protease (PR), or NS2/NS3 or NS3/NS4A protease of HCV, is blocked or inactive, the entire scaffold polypeptide will be retained in the ER, and as a consequence will not be detected on the cell's extracellular surface.

A chimeric (e.g., recombinant) polypeptide comprising:
(i) a transmembrane domain;
(ii) a signal sequence or any amino acid motif that places the scaffold protein on the extracellular surface of the cell; and
(iii) a detectable moiety (e.g., a Green Fluorescent Protein (GFP) or a luciferase, or any compound that can be directly or indirectly detected); or (2) the chimeric polypeptide of (1), wherein the scaffold protein further comprises an endoplasmic reticulum (ER) retention motif or a KDEL motif, wherein in alternative embodiments the ER retention motif or KDEL motif is positioned in the scaffold protein such that when PR is active the scaffold will be separated into two pieces, leaving the ER retention motif-comprising or KDEL motif-comprising portion of the polypeptide in the ER and freeing the detectable moiety-comprising portion to the cell's extracellular membrane, and if PR is blocked or inactive, the entire scaffold polypeptide will be retained in the ER, and as a consequence will not be detected on the cell's extracellular surface.

In one embodiment, assays and cells of the invention can be used to identify whether or not an enzyme, e.g., protease or HIV-1 protease (PR), or NS2/NS3 or NS3/NS4A protease of HCV, is active. This is based on the detection of a tag on the surface of a mammalian cell, e.g., a human cell. If the enzyme, e.g., protease or HIV-1 protease (PR), or NS2/NS3 or NS3/NS4A protease of HCV, is active, no tag will be detected. If the enzyme, e.g., protease or HIV-1 protease (PR), or NS2/NS3 or NS3/NS4A protease of HCV, is inactive or blocked, the tag will appear on the surface of the cell. This can be easily recognized with antibodies that are coupled to a fluorescent dye through a technique referred to as flow cytometry. As a result, analysis of various drugs on the expression of the tag on the surface of the cell can be conducted. If the drug inhibits or blocks the enzyme, e.g., protease or HIV-1 protease (PR), or NS2/NS3 or NS3/NS4A protease of HCV, the cells will become positive for tag surface expression. In contrast, if the drug is not active against the enzyme, e.g., protease or HIV-1 protease (PR), or NS2/NS3 or NS3/NS4A protease of HCV, the cells will be negative for tag expression.

In one embodiment, assays and cells of the invention rely on the engineering of a recombinant polypeptide, the so-called "scaffold protein". In one embodiment, this scaffold is referred to as p2/7; which is one of the natural targets of PR, and PR cleaves it at the boundary between p2 and p7 during normal HIV-1 infection. PR is essential for the viral lifecycle.

Drugs against the enzyme, e.g., protease or HIV-1 protease (PR), or NS2/NS3 or NS3/NS4A protease of HCV, can hinder its capacity to cleave its targets, resulting in inhibitory effects on viral replication. Thus, in some embodiments of this invention a p2/p7 scaffold is engineered in such a way that instead of being expressed inside the cell, it is expressed on the surface of the cell. To achieve surface expression, a "scaffold protein" such as the exemplary p2/p7 is fused to a signal (e.g., signal sequence) that directs it to the cell surface. Addition of another segment; a transmembrane domain (or motif), allows it to become incorporated into the cell surface. A marker (tag) is added to the p2/p7 scaffold to allow detection of its presence on the surface.

In one embodiment, assays and cells of the invention are adapted to a high throughput system, where they can be used e.g., in the search of much needed novel drugs against the enzyme, e.g., protease or HIV-1 protease (PR), or NS2/NS3 or NS3/NS4A protease of HCV.

In alternative embodiments, methods of the invention are practiced in vitro or in vivo. For example, the cells need not be intact for membrane analysis of the presence or absence of detectable moieties (e.g., Green Fluorescent Protein (GFP), luciferase or any compound that can be directly or indirectly detected).

Cell-Based Methods and Multiplexed Systems

In alternative embodiments, the invention provides cell-based methods and multiplexed systems for monitoring the activity of any enzyme, e.g., protease or HIV-1 protease (PR), or NS2/NS3 or NS3/NS4A protease of HCV, comprising:

(1) (a) providing: a nucleic acid encoding a chimeric (hybrid) protein operatively linked to a transcriptional regulatory unit (e.g., a promoter); and, a cell comprising an environment capable of supporting the expression of the chimeric (hybrid) protein by the nucleic acid, wherein the chimeric (hybrid) protein comprises a chimeric Gal4 expression system comprising (i) an N-terminal Gal4 DNA-binding domain (e.g., DBD: aa 1-147); (ii) an enzyme whose activity is to be monitored, or an enzymatically active fragment thereof; and (iii) a Gal4 C-terminal Transactivation domain (e.g., TAD: aa 768-881), and the enzyme whose activity is to be monitored or the enzymatically active fragment thereof is positioned in or within the chimeric protein such that an enzymatically active enzyme or enzymatically active fragment thereof is capable of cleaving or physically separating or otherwise functionally separating the N-terminal Gal4 DNA-binding domain from the Gal4 C-terminal Transactivation domain such that the Gal4 can no longer act as a functional transcription factor, and if the enzyme whose activity is to be monitored is inhibited such that it is no longer enzymatically active (or substantially no longer enzymatically active) the Gal4 C-terminal Transactivation domain in conjunction with the N-terminal Gal4 DNA-binding domain can function as a functional transcription factor;

(b) inserting (transfecting) the nucleic acid of (a) into the cell, wherein optionally the cell does not already express a heterologous or endogenous enzyme, e.g., protease or HIV-1 protease (PR), or NS2/NS3 or NS3/NS4A protease of HCV; and (c) contacting the cell with a putative (test) enzyme inhibitor, wherein optionally the enzyme inhibitor comprises a small molecule, a protein, a nucleic acid, a polysaccharide and/or a lipid, and optionally the enzyme inhibitor is added to the cell before, during and/or after inserting (transfecting) the nucleic acid of (a) into the cell and/or expressing the chimeric protein encoded by the nucleic acid of (a) in the cell, and optionally cell-based method further comprises a negative control set of cells into which the nucleic acid of (a) also has been inserted and transfected and expresses the chimeric protein encoded by the nucleic acid of (a), but the negative control set of cells is not exposed to the putative (test) enzyme inhibitor or is exposed to a different putative (test) enzyme inhibitor;

(d) determining whether the putative (test) enzyme inhibitor is an effective or sufficient inhibitor of the enzyme or enzymatically active fragment thereof by measuring the ability of the Gal4 C-terminal Transactivation domain in conjunction with the N-terminal Gal4 DNA-binding domain to function as a functional transcription factor;

(2) the method of (1), wherein the enzyme is a protease or an HIV-1 protease (PR), or a NS2/NS3 or NS3/NS4A protease of HCV; or (3) the method of (1), wherein the cell is a lymphocyte or a T cell, or a CD4+ T cell, or a human cell.

In alternative embodiments the methods further comprise running a negative control comprising dividing the plurality of the cells co-expressing the nucleic acid of (a) in the cell and not adding the compound to be screened (the putative (test) enzyme inhibitor) as an inhibitor to one of the divided cell samples.

In alternative embodiments the methods further comprise running a positive control comprising dividing the plurality of the cells co-expressing the nucleic acid of (a) in the cell and adding a known inhibitor of the enzyme, e.g., a known inhibitor of a protease or an HIV-1 protease (PR), or a NS2/NS3 or NS3/NS4A protease of HCV, to one of the divided cell samples.

In alternative embodiments of the methods, the transcriptional regulatory unit comprises a promoter, an inducible promoter or a constitutive promoter.

In alternative embodiments of the methods, the cell is a mammalian cell, a monkey cell or a human cell.

In alternative embodiments of the methods, the positive activity of the Gal4 C-terminal Transactivation domain in conjunction with the N-terminal Gal4 DNA-binding domain to function as a functional transcription factor is detected or measured by a high throughput screen, a flow cytometry or microscope visualization.

In alternative embodiments of the methods, the ("test") compound to be screened as an inhibitor of the enzyme, e.g., protease or HIV-1 protease (PR), or NS2/NS3 or NS3/NS4A protease of HCV, comprises a small molecule, a nucleic acid, a polypeptide or peptide, a peptidomimetic, a polysaccharide or a lipid.

In alternative embodiments of the methods, the compound to be screened as an inhibitor of the enzyme, e.g., protease or HIV-1 protease (PR), or NS2/NS3 or NS3/NS4A protease of HCV, is a member of a library of compounds to be screened, or a member of a random peptide library or a chemical compound library.

In alternative embodiments of the methods, the transcriptional regulatory unit comprises a promoter, e.g., an inducible promoter or a constitutive promoter.

In alternative embodiments of the methods, the cell is a mammalian cell, a monkey cell or a human cell; or a lymphocyte, or a T cell, or a CD4- or CD8-expressing cell.

In alternative embodiments of the methods, the enzyme is a viral protease, a microbial protease or a mammalian protease.

In alternative embodiments the invention provides isolated, recombinant or synthetic nucleic acids encoding a chimeric (hybrid) protein operatively linked to a transcriptional regulatory unit (e.g., a promoter)

wherein the chimeric (hybrid) protein comprises a chimeric Gal4 expression system comprising (i) an N-terminal Gal4 DNA-binding domain (e.g., DBD: aa 1-147); (ii) an enzyme whose activity is to be monitored, or an enzymatically active fragment thereof; and (iii) a Gal4 C-terminal Transactivation domain (e.g., TAD: aa 768-881), and the enzyme whose activity is to be monitored or the enzymatically active fragment thereof is positioned in or within the chimeric protein such that an enzymatically active enzyme or enzymatically active fragment thereof is capable of cleaving or physically separating or otherwise functionally separating the N-terminal Gal4 DNA-binding domain from the Gal4 C-terminal Transactivation domain such that the Gal4 can no longer act as a functional transcription factor, and if the enzyme whose activity is to be monitored is inhibited such that it is no longer enzymatically active (or substantially no longer enzymatically active) the Gal4 C-terminal Transactivation domain in conjunction with the N-terminal Gal4 DNA-binding domain can function as a functional transcription factor.

In alternative embodiments the invention provides cells comprising the isolated, recombinant or synthetic nucleic acid of the invention.

In alternative embodiments the invention provides vectors, expression cassettes, cosmids or plasmids comprising or having contained therein the isolated, recombinant or synthetic nucleic acid of the invention.

In alternative embodiments the invention provides chimeric Gal4 expression systems comprising a polypeptide comprising (i) an N-terminal Gal4 DNA-binding domain (e.g., DBD: aa 1-147); (ii) an enzyme whose activity is to be monitored, or an enzymatically active fragment thereof; and (iii) a Gal4 C-terminal Transactivation domain (e.g., TAD: aa 768-881), and the enzyme whose activity is to be monitored or the enzymatically active fragment thereof is positioned in or within the chimeric protein such that an enzymatically active enzyme or enzymatically active fragment thereof is capable of cleaving or physically separating or otherwise functionally separating the N-terminal Gal4 DNA-binding domain from the Gal4 C-terminal Transactivation domain such that the Gal4 can no longer act as a functional transcription factor, and if the enzyme whose activity is to be monitored is inhibited such that it is no longer enzymatically active (or substantially no longer enzymatically active) the Gal4 C-terminal Transactivation domain in conjunction with the N-terminal Gal4 DNA-binding domain can function as a functional transcription factor.

In alternative embodiments the enzyme is a viral protease, a microbial protease or a mammalian protease, or the enzyme is an HIV-1 protease (PR), or a NS2/NS3 or a NS3/NS4A protease.

In alternative aspects, compositions and methods of the invention are practiced in vitro or in vivo. For example, the cells need not be intact for analysis of the effectiveness of a test compound to be sufficiently effective in inhibiting the activity of an enzyme, e.g., an HIV protease.

In alternative aspects, compositions and methods of the invention are practiced as multiplexed systems adapted for multiplexed analysis of a plurality of enzyme (more than one enzyme) inhibitors or modulators, comprising: a chimeric Gal4 expression system of the invention, or a cell of the invention, or the cell-based method for monitoring the activity of any enzyme of the invention, wherein inhibition of different enzymes is monitored by the expression of a different detectable moiety, e.g., a different Fluorescent Protein (FP), e.g., an e-green fluorescent protein, or eGFP (excited with the 488 nm blue laser, an e-cyan fluorescent protein (or eCFP, using a 405 nm violet laser), and/or an mOrange or an mCherry (561 nm yellow laser).

Cell-Based Assays for the Identification of Compositions that Inhibit Envelop Processing In alternative embodiments, the invention provides cell-based assays to screen for compositions, e.g., small molecules or drugs, that inhibit or modify the activity of enzymes such as calcium-dependent protein convertases involved in HIV envelop protein processing, including cleavage of the HIV gp160 envelope precursor, resulting in gp120 and gp41 envelope products.

In alternative embodiments, the invention provides isolated, recombinant or synthetic nucleic acids encoding a chimeric (hybrid) protein, wherein the chimeric (hybrid) protein comprises (or consists of) from N- to C-terminus:

(a) (i) a signal sequence (motif) for Endoplasmic Reticulum (ER) targeting, (ii) a tag or detection moiety, or "scaffold", capable of being recognized on a cell surface, (iii) at least two transmembrane domains that span the ER membrane, with an extra loop at the ER luminal face, (iv) an enzyme recognition/cleavage site spanning a segment of a gp120/41 boundary, facing the ER lumen, and (v) an ER retention sequence or motif;

(b) the chimeric (hybrid) protein of (a), wherein the tag or detection moiety, or "scaffold", comprises a tag for an antibody or an antigen binding fragment thereof (the antibody binding specifically to the tag or detection moiety, or "scaffold"), or the tag or detection moiety, or "scaffold", comprises a ligand, or the tag or detection moiety, or "scaffold", comprises a FLAG molecule or equivalent thereof;

(c) the chimeric (hybrid) protein of (a), wherein enzyme recognition/cleavage site comprises a furin enzyme recognition/cleavage site, a calcium-dependent protein convertase enzyme recognition/cleavage site, prohormone convertase-1 (PC1) enzyme recognition/cleavage site, or an enzyme recognition/cleavage site derived from a member of the subtilisin/kexin family of proprotein convertases;

(d) the chimeric (hybrid) protein of (a), wherein enzyme recognition/cleavage site comprises an enzyme recognition/cleavage site within the V3 loop of gp120;

(e) the chimeric (hybrid) protein of (a), wherein the ER retention sequence or motif comprises a KDEL (SEQ ID NO:1) sequence or equivalent thereof;

(f) the chimeric (hybrid) protein of (a), wherein the gp120/41 is an HIV-1 gp120/41;

(g) the chimeric (hybrid) protein of (a), wherein the at least two transmembrane domains that span the ER membrane consist of two transmembrane domains;

(h) the chimeric (hybrid) protein of (a), wherein the at least two transmembrane (TM) domains that span the ER membrane comprise at least one TM of a CRR5;

(i) the chimeric (hybrid) protein of (h), wherein the at least two transmembrane (TM) domains that span the ER membrane comprise TM1 and TM2 from the CRR5;

(j) the chimeric (hybrid) protein of (a), wherein the gp120/gp41 boundary comprises the recognition/cleavage site REKRA (SEQ ID NO:14), (k) the chimeric (hybrid) protein of (a), wherein the gp120/gp41 boundary further comprises a restriction enzyme recognition site acids at both sides, or comprises additional amino-acids at both sides comprising AKRRV-VQREKR (SEQ ID NO:15) and AVGIGALF (SEQ ID NO:16); or (l) the isolated, recombinant or synthetic nucleic acid encoding the chimeric (hybrid) protein is operatively linked to a transcriptional regulatory unit, or a promoter such as an inducible or constitutive promoter.

In alternative embodiments, the invention provides vectors, recombinant viruses, cloning vehicles, expression cassettes, cosmids or plasmids comprising (or consisting of) or having contained therein the isolated, recombinant or synthetic nucleic acid of the invention.

In alternative embodiments, the invention provides chimeric or hybrid polypeptides comprising (or consisting of): (a) the polypeptide encoded by the nucleic acid of the invention; or (b) the chimeric (hybrid) protein of (a), wherein the protein comprises a synthetic protein or peptide, recombinant protein or peptide, a peptidomimetic or a combination thereof.

In alternative embodiments, the invention provides chimeric or hybrid proteins comprising (or consisting of) from N- to C-terminus:

(a)) (i) a signal sequence (motif) for Endoplasmic Reticulum (ER) targeting, (ii) a tag or detection moiety, or "scaffold", capable of being recognized on a cell surface, (iii) at least two transmembrane domains that span the ER membrane, with an extra loop at the ER luminal face, (iv) an enzyme recognition/cleavage site spanning a segment of a gp120/41 boundary, facing the ER lumen, and (v) an ER retention sequence or motif;

(b) the chimeric (hybrid) protein of (a), wherein the tag or detection moiety, or "scaffold", comprises a tag for an antibody or an antigen binding fragment thereof (the antibody binding specifically to the tag or detection moiety, or "scaffold"), or the tag or detection moiety, or "scaffold", comprises a ligand, or the tag or detection moiety comprises a FLAG molecule or equivalent thereof;

(c) the chimeric (hybrid) protein of (a), wherein enzyme recognition/cleavage site comprises a furin enzyme recognition/cleavage site, a calcium-dependent protein convertase enzyme recognition/cleavage site, prohormone convertase-1 (PC1) enzyme recognition/cleavage site, or an enzyme recognition/cleavage site derived from a member of the subtilisin/kexin family of proprotein convertases;

(d) the chimeric (hybrid) protein of (a), wherein enzyme recognition/cleavage site comprises an enzyme recognition/cleavage site within the V3 loop of gp120;

(e) the chimeric (hybrid) protein of (a), wherein the ER retention sequence or motif comprises a KDEL (SEQ ID NO:1) sequence or equivalent thereof;

(f) the chimeric (hybrid) protein of (a), wherein the gp120/41 is an HIV-1 gp120/41;

(g) the chimeric (hybrid) protein of (a), wherein the at least two transmembrane domains that span the ER membrane consist of two transmembrane domains;

(h) the chimeric (hybrid) protein of (a), wherein the at least two transmembrane (TM) domains that span the ER membrane comprise at least one TM of a CRR5;

(i) the chimeric (hybrid) protein of (h), wherein the at least two transmembrane (TM) domains that span the ER membrane comprise TM1 and TM2 from the CRR5;

(j) the chimeric (hybrid) protein of (a), wherein the gp120/gp41 boundary comprises the recognition/cleavage site REKRA (SEQ ID NO:2);

(k) the chimeric (hybrid) protein of (a), wherein the gp120/gp41 boundary further comprises a restriction enzyme recognition site acids at both sides, or comprises additional amino-acids at both sides comprising AKRRV-VQREKR (SEQ ID NO:15) and AVGIGALF (SEQ ID NO:16); or (l) the chimeric (hybrid) protein of (a), wherein the protein comprises (or consists of) a synthetic protein or peptide, recombinant protein or peptide, a peptidomimetic or a combination thereof.

In alternative embodiments, the invention provides cells comprising (a) an isolated, recombinant or synthetic nucleic acid of the invention; (b) a vector, recombinant virus, cloning vehicle, expression cassette, cosmid or plasmid of the invention; (c) a chimeric or hybrid polypeptide of the invention; or, (d) the cell of (a), (b) or (c), wherein the cell is a mammalian or a human cell.

In alternative embodiments, the invention provides cell-based methods for monitoring the activity of an enzyme, or for screening for an inhibitor of the enzyme, comprising:

(1) (a) providing: (i) a nucleic acid encoding the chimeric (hybrid) protein of the invention, or the nucleic acid of the invention, operatively linked to a transcriptional regulatory unit (e.g., a promoter, such as an inducible or constitutive promoter), or (ii) the vector, recombinant virus, cloning vehicle, expression cassette, cosmid or plasmid of the invention; and, a cell comprising an environment capable of supporting the expression of the chimeric (hybrid) protein by the nucleic acid;

(b) inserting (e.g., transfecting or infecting) the nucleic acid, vector, recombinant virus, cloning vehicle, expression cassette, cosmid or plasmid of (a) into the cell; and (c) contacting the cell with a putative (test) enzyme inhibitor, wherein optionally the enzyme inhibitor is added to the cell before, during and/or after inserting (transfecting) the nucleic acid, vector, recombinant virus, cloning vehicle, expression cassette, cosmid or plasmid of (a) into the cell and/or expressing the chimeric protein encoded by a nucleic acid of (a) in the cell, and optionally the cell-based method further comprises a negative, positive and/or alternative control set of cells into which the nucleic acid, vector, recombinant virus, cloning vehicle, expression cassette, cosmid or plasmid of (a) also has been inserted (or transfected) and expresses the chimeric protein encoded by a nucleic acid of (a), but the negative control set of cells is not exposed to the putative (test) enzyme inhibitor or is exposed to a different putative (test) enzyme inhibitor, or a different amount of putative (test) enzyme inhibitor, or a positive control wherein the cells are exposed to a known inhibitor of the enzyme; and (d) determining whether the putative (test) enzyme inhibitor is an effective or sufficient inhibitor or modulator of the enzyme or an enzymatically active fragment thereof by measuring the ability of the putative (test) enzyme inhibitor to partially or completely inhibit cleavage of the enzyme recognition/cleavage site;

(2) measuring the ability of the putative (test) enzyme inhibitor to partially or completely inhibit cleavage of the enzyme recognition/cleavage site comprises detecting and/or measuring the amount of tag or detection moiety, or "scaffold", on the cell surface; or (3) the method of (1) or (2), wherein the cell is a lymphocyte or a T cell, or a CD4+ T cell, or a human cell.

In one embodiment the method further comprises running a negative control comprising dividing the plurality of the cells co-expressing a nucleic acid of (a) in the cell and not adding the compound to be screened (the putative (test) enzyme inhibitor) as an inhibitor to one of the divided cell samples.

In one embodiment the method further comprises running a positive control comprising dividing the plurality of the cells co-expressing the nucleic acid of (a) in the cell and adding a known inhibitor of the enzyme, e.g., a known inhibitor of a furin enzyme, a calcium-dependent protein convertase enzyme, prohormone convertase-1 (PC1) enzyme, or an enzyme from a member of the subtilisin/kexin family of proprotein convertases, to one of the divided cell samples.

In one embodiment of a method of the invention the transcriptional regulatory unit comprises a promoter, an inducible promoter or a constitutive promoter. The cell can be a mammalian cell, a monkey cell or a human cell.

In one embodiment of a method of the invention the tag or detection moiety, or "scaffold", is detected or measured on the cell surface by a high throughput screen, a flow cytometry or microscope visualization.

In one embodiment of a method of the invention the compound to be screened as an inhibitor of the enzyme comprises a small molecule, a nucleic acid, a polypeptide or peptide, a peptidomimetic, a polysaccharide and/or a lipid. In one embodiment of a method of the invention the compound to be screened as an inhibitor of the enzyme is a member of a library of compounds to be screened, or a member of a random peptide library or a chemical compound library.

In one embodiment of a method of the invention the cell is a mammalian cell, a monkey cell or a human cell; or a lymphocyte, or a T cell, or a CD4- or CD8-expressing cell. In alternative aspects, methods of the invention are practiced in vitro or in vivo. For example, the cells need not be intact for analysis of the effectiveness of a test compound to be sufficiently effective in inhibiting the activity of an enzyme.

The details of one or more embodiments of the invention are set forth in the accompanying drawings and the description below. Other features, objects, and advantages of the invention will be apparent from the description and drawings, and from the claims.

All publications, patents, patent applications, GenBank sequences and ATCC deposits, cited herein are hereby expressly incorporated by reference for all purposes.

DESCRIPTION OF DRAWINGS

FIG. 9 illustrates a fluorescence analysis showing indirect confirmation of HIV-1 PR activity.

FIG. 12 illustrates a Western Blot of PR/GFP fusion proteins with anti-PR antibody, as discussed in detail in Example 1, below.

FIG. 15 illustrates two exemplary constructs of the invention: pCMV/GFP=>Zeo, and pCMV/GFP=>SS-FLAG/P2-P7/TM=>Zeo; and flow cytometry analysis of the expression of these two scaffold proteins on the surface of 293T cells.

FIG. 19 schematically illustrates an overview of an exemplary assay of the invention: FIG. 19A—Wild type Gal4 as control, no Dox; FIG. 19B—In the presence of Dox, Gal4 expression is induced; FIG. 19C—The same system with the PR/Gal4 fusion; FIG. 19D—The same scenario as in 19C but in the presence of a PR inhibitor; as discussed in detail in Example 2, below.

FIG. 20 illustrates a transient expression of components of an exemplary assay in HEK293T cells: FIG. 20A schematically illustrates constructs used for transient expression of the assay elements; FIG. 20B: Top Panel: illustration of a fluorescence microscopy of eGFP expression in HEK293T cells 24 hours post transfection with the reporter vector (pFR), or co-transfection with the reporter vector plus either the Gal4, PR/Gal4, or PRm/Gal4 vectors; Bottom panel: HEK293T cells were analyzed by flow cytometry at 24 hours post transfection with the same conditions top panel; FIG. 20C graphically illustrates the quantification of eGFP expression in HEK293T transfected with various assay elements; as discussed in detail in Example 2, below.

FIG. 21 illustrates generation of a monoclonal T-cell line stably expressing inducible assay elements: FIG. 21A (upper left) schematically illustrates exemplary constructs utilized to generate infectious particles for the transduction of SupT1 cells with the various assay elements; FIG. 21B (right) illustrates data from a cell sorting assay; FIG. 21C (lower left) illustrates images of fluorescence microscopy of SupT1 clones expressing the assay elements; as discussed in detail in Example 2, below.

FIG. 22 graphically illustrates data determining the optimal conditions for activating the assay to screen for PR inhibition: FIG. 22A graphically illustrates a doxycycline titration using clonal SupT1 cells harboring an inducible Gal4, PR/Gal4 or PRm/Gal4 pre-incubated with either DMSO or 10 µM Indinavir and then either left untreated, or activated with 50, 100, 200, 500, 1000, or 20000 ng/mL of Dox; FIG. 22B graphically illustrates the time course of eGFP Induction in response to Doxycyline activation in the presence of DMSO or a PI; as discussed in detail in Example 2, below.

FIG. 24A schematically illustrates: No doxycycline, Gal4 (DB and TA domains) cannot be expressed; FIG. 24B schematically illustrates: In the presence of doxycycline: D, rtTA binds to the tet-responsive element (TRE) and induces Gal4 expression resulting in the activation of GFP expression; FIG. 24C schematically illustrates: protease/Gal4 is expressed; however, its catalytic activity results in the separation of the Gal4 domains, resulting in the lack of GFP expression; FIG. 24D schematically illustrates: in the presence of a protease inhibitor (PI), the PR/Gal4 fusion remains intact, resulting in the induction of GFP expression; as discussed in detail in Example 3, below.

FIG. 27A. Fluorescence microscopy; FIG. 27B. Flow cytometry; FIG. 27C Quantification of Flow data; PI=10 µM Indinavir; as discussed in detail in Example 3, below.

FIG. 38 schematically illustrates constructs for assays of the invention; as discussed in detail in Example 4, below.

Like reference symbols in the various drawings indicate like elements.

DETAILED DESCRIPTION

Figure 1:
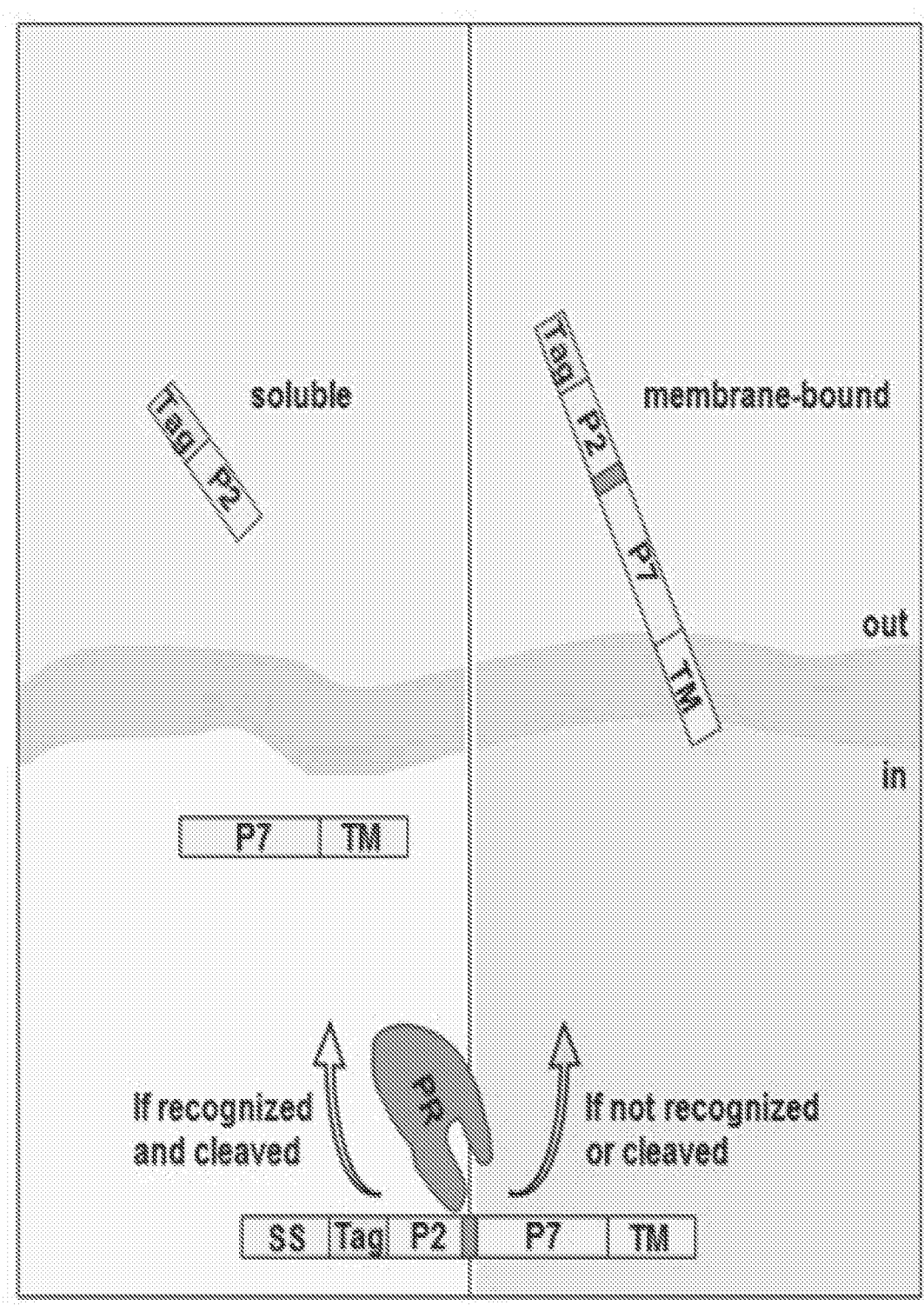
FIG. 1 graphically illustrates a representation of an exemplary assay of the invention, as discussed in detail, below.

The invention provides methods and compositions, including chimeric recombinant proteins, nucleic acids that encode them, and cells and kits comprising them, to screen for compositions, e.g., small molecule drugs, that can modulate, e.g., inhibit or enhance, viral proteases, including retroviral (e.g., HIV) proteases.

In one embodiment, the invention provides cells and cell-based assays for monitoring the activity of viral proteases, e.g., HIV-1 protease (PR), which is an aspartyl protease. In one embodiment, these cells and cell-based assays are used to screen for and identify novel viral protease, e.g., PR, inhibitors. In one embodiment, assays of the invention effectively couple the surface (extracellular) expression of a protein used as a scaffold (a scaffold protein), with the activity of the viral protease, e.g., PR. In alternative embodiments, polypeptides of the invention comprise HIV p2, p7 or both p2 and p7; p2/p7 of the HIV-1 strain HXB2 (taken as the prototype genome) is part of that virus's viral proteome, and contains one of the natural targets for the recognition and cleavage site of PR.

In one embodiment, the scaffold is engineered for its conditional expression on the surface of a cell, e.g., a eukaryotic, a yeast or a mammalian cell. For that purpose, in one embodiment, the scaffold is fused to a signal sequence to enable efficient and/or directed transport, and a transmembrane domain (e.g., an Lyt2, the murine CD8 molecule, and the like) is used to enable subsequent insertion in the cell membrane. In one embodiment, a tag such as a FLAG tag is added to the scaffold downstream of the signal sequence for detection, e.g., for antibody detection, e.g., through flow cytometry or equivalent visualization.

In one embodiment, the assay co-expresses both the scaffold protein and the viral protease, e.g., the HIV-1 PR, which if active will bind to and cleave the scaffold at the protease recognition sequence.

In one embodiment, both scaffold and protease are co-expressed in T cells, e.g., SupT1 T-cells, in an inducible off/on-based vector system (e.g., activated upon addition of tetracycline or doxycycline). Inducible expression of protease, e.g., PR, helps avoid its possible cytopathic effects. Inducible expression of the scaffold is necessary as protease, e.g., PR, will only be able to prevent surface expression of newly synthesized intact scaffold, as the pre-inserted scaffold would not be removed from the cell surface by protease.

In one embodiment, the logic behind the engineering of the scaffold as a membrane-expressed protein is as follows: in the presence of the active viral protease, the proteolytic enzyme will cleave the scaffold, resulting in the loss of transmembrane domain, thus preventing tag cell surface expression. In the absence of protease, or when protease is blocked or inhibited, the scaffold will be intact and incorporated into the membrane. As a result, the surface expression of the scaffold can be determined by flow cytometry allowing the discrimination between active and inactive or blocked protease. The assay is cell-based, and can be easily implemented for a high throughput screen, e.g., FACS. As such, the assay is invaluable for drug discovery, and can be utilized in biological screens aimed at finding novel protease inhibitors through random peptide libraries or chemical compounds libraries.

FIG. 1 is an illustration that is a representation of an exemplary assay of the invention that will enable discrimination between cleavage (left panel) and no cleavage (right panel) by HIV PR. SS: Signal sequence, TM: Transmembrane domain, PR: protease, orange box: protease recognition/cleavage site.

In one embodiment, the invention engineers a protein scaffold bearing the protease cleavage site on the cell surface of a mammalian cell. In one embodiment, the invention expresses, or co-expresses, a protease, e.g., a HIV-1 protease, and a scaffold used as a target, in an inducible manner (the protease, the scaffold, or both can be expressed via an inducible mechanism, e.g., an inducible transcriptional regulator).

In one embodiment, the invention provides assays that can be adapted for a high throughput manner using e.g. flow cytometry such as FACS, and can discriminate between active and non-active or blocked protease. In one embodiment, the invention provides assays that can be easily adapted for high throughput screening. In one embodiment, the invention provides assays of this invention can be used to screen for novel protease inhibitors.

In one embodiment, the invention provides assays of this invention adapted for the screen of random peptide libraries or chemical compounds for drug discovery.

In one embodiment, the methods of the invention use a random peptide library or any peptide of choice, which can be introduced 'in cis', replacing the p2/p7 recognition/cleavage site, enabling the discovery of higher affinity sites for PR, which can be the basis for the development of competitor peptidomimetic drugs. In one embodiment, the random peptide library is expressed 'in trans', enabling the discovery of competitors/inhibitors for PR, which can be the basis for peptidomimetic drugs.

In one embodiment, the non-biased approach of the invention permits the rescue of peptides or chemicals targeted not necessarily to the catalytic site of PR. Thus, the assays of the invention provide for extensive characterization of PR, facilitating the elucidation of interactions of PR with cellular targets, its mode of action and modulation, in the context of the host cell. Assays of this invention will permit the replacement of PR with PR from different viral strains or clades, or truncated versions of PR, enabling further dissection of PR activity, and study its modulation through co-expression of cellular factors or addition of drugs.

The assays of this invention can be further adapted to proteases of different viruses such as Hepatitis C by just exchanging the recognition/cleavage site segment of the scaffold. The assays of this invention can thus be exploited for the search for protease inhibitors against any of the known viral pathogens that utilize their own protease/s as part of their lifecycles.

The assays of this invention can be adapted for the search of HIV envelope processing inhibitors. One of the HIV proteins, envelope, is processed by furin and other cellular convertases. By just exchanging the recognition/cleavage segment of the scaffold with the envelope recognition site, the assay can be further utilized for the finding of envelope processing inhibitors. This same scaffold is useful for the search of transport inhibitors, as envelope is transported through the ER, trans-Golgi network in order to be inserted within the cell membrane.

In alternative embodiments, the assays of this invention comprise expression of a scaffold naturally expressed in the cytoplasm that is able to be exported into the cell membrane.

In alternative embodiments, assays of this invention comprise expression of both PR and scaffold in an off/on system for inducible expression.

In alternative embodiments, assays of this invention comprise expression of a protein that is expressed on the surface of the mammalian cell only when not cleaved by a protease, e.g., an HIV protease.

In alternative embodiments, assays of this invention can be adapted for the screen of random peptide libraries or chemical compounds.

In alternative embodiments, assays of this invention can be implemented in mammalian cells and other cells, e.g., yeast or bacterial cells.

In alternative embodiments, methods provide for the construction of the scaffold and its expression on the cell surface. In alternative embodiments, the p2/p7 scaffold has been engineered as described and effectively expressed on the cell surface. In alternative embodiments, the scaffold has been introduced in a retroviral vector.

In one study, for proof of principle, the expression of an exemplary scaffold correlates with the Green Fluorescent Protein (GFP) expression, as the vector (illustrated in FIG. 2A) contains an internal ribosome entry site followed by GFP. The p2/p7-engineered scaffold with the FLAG tag and a signal sequence was introduced upstream of the internal ribosome entry site (IRES) GFP cassette of the retroviral vector pBMN-IRES-eGFP (illustrated in FIG. 2A) (kindly provided by Garry Nolan from Stanford University). The scaffold construct has been introduced in a Tet-off/on vector for inducible expression upon addition of doxycycline.

Figure 2A:
FIG. 2A graphically illustrates an exemplary vector used to corroborate the expression of a scaffold of this invention on a cell surface by flow cytometry, as graphically illustrated in FIG. 2B, as discussed in detail, below.
Figure 2B:
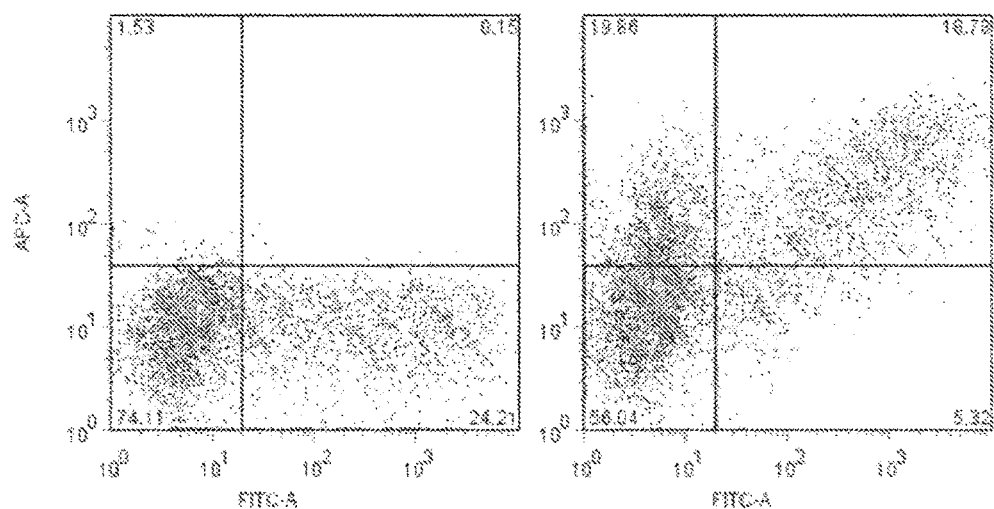

This construct allows stable expression of the insert and correlation of green fluorescence with expression of the gene of interest (p2/p7 in our case). This vector was used to corroborate the expression of a scaffold of this invention on the cell surface by flow cytometry, as graphically illustrated in FIG. 2B: a FACS analysis of 293T and 293T-FLAG-p2/p7 expressing cells. The FLAG-p2/p7 scaffold was introduced upstream an IRES-GFP cassette in the pBMN-IRES-eGFP retroviral vector (as illustrated in FIG. 2A). Cells were stained with anti-FLAG (Sigma) and APC-coupled secondary antibody (Invitrogen, Carlsbad, Calif.) (right lower panel). SS: Signal Sequence, TM: Transmembrane domain.

The Expression of Protease in a Non-Toxic Inducible Manner.

Figure 3:
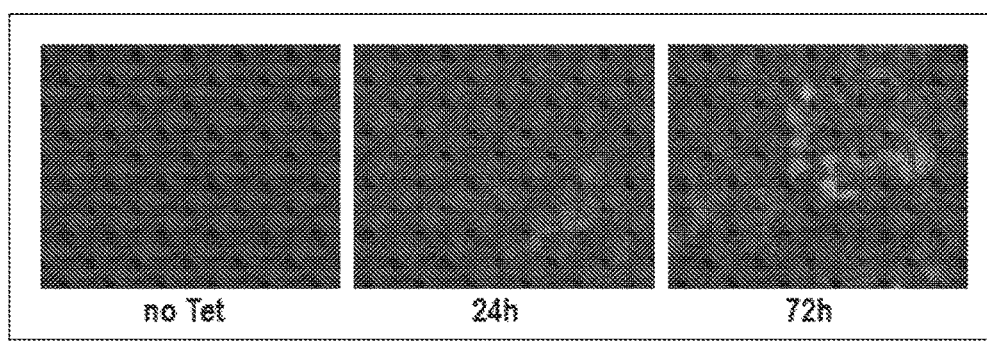
FIG. 3 illustrates by fluorescence microscopy use of an exemplary vector of the invention, a Tet-inducible HIV-based self-inactivating vector, that allows regulated expression of a gene of interest, as discussed in detail, below.

In one embodiment, to achieve low levels of protease, e.g., PR, expression in mammalian cells, a tetracycline (Tet) inducible system is used. FIG. 3 illustrates by fluorescence microscopy use of an exemplary vector of the invention, a Tet-inducible HIV-based self-inactivating vector, that allows regulated expression of the gene of interest. In this case, we have used the enhanced green fluorescent protein (eGFP) as the ectopic gene. This vector allows different levels of protein expression. Tight repression and expression of PR at low levels may be crucial to avoid the possible side effects of PR. It is important to mention that this system is an off/on system that allows for expression of the gene of interest only upon addition of tetracycline or doxycycline. The inducible system allows for de novo synthesis of the scaffold, needed for the successful implementation of the assay. FIG. 3 illustrates by fluorescence microscopy HeLa cells infected with a Tet inducible HIV-based self-inactivating vector. The cells were incubated with 1 μg/ml Tet and eGFP expression was observed by fluorescence microscopy 24 and 72 h post addition of Tet. PR was expressed by itself and as a GFP fusion. As high level expression of PR might be toxic to the cell, the PR inhibitor Saquinavir was added to inhibit its activity but not its expression.

Figure 4:
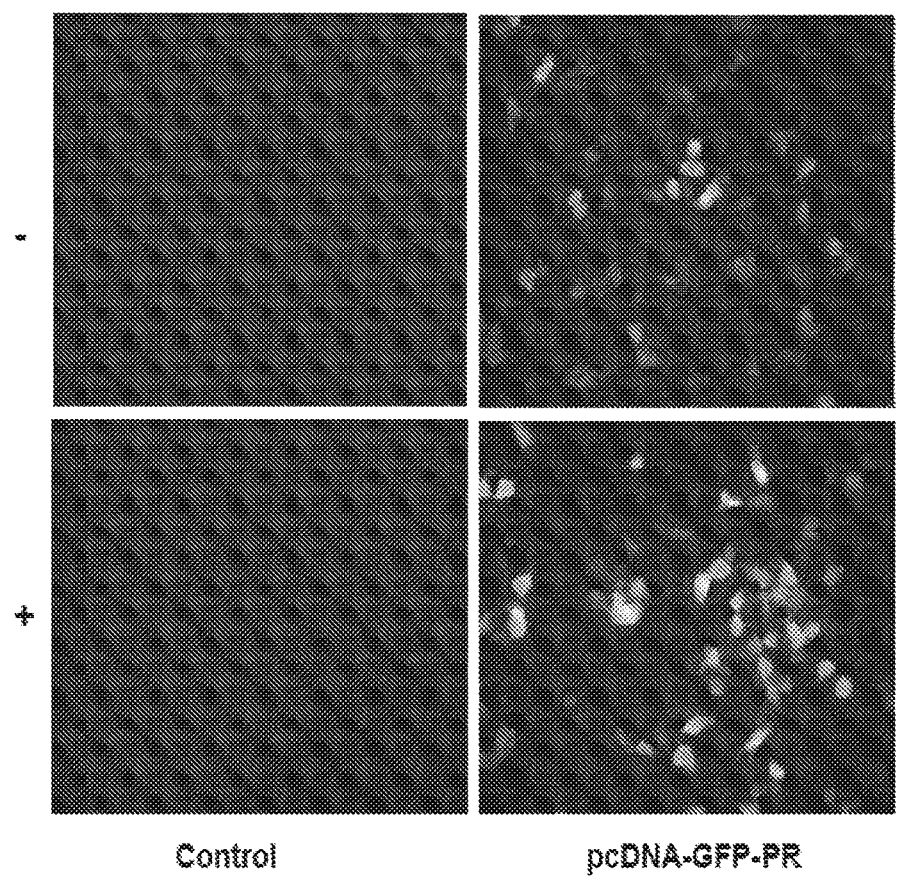
FIG. 4, lower panels, illustrate by fluorescence microscopy that a N-terminal GFP fusion is highly expressed, as illustrated in FIG. 4; and, this fusion seems to be expressed at low levels even in the absence of inhibitor, as illustrated in FIG. 4, upper panels and FIG. 5, demonstrating that active PR can be expressed at low levels without cytotoxic effects, as discussed in detail, below.

As expected, the N-terminal GFP fusion is highly expressed in this case, as illustrated in FIG. 4, lower panels. Importantly, this fusion seems to be expressed at low levels even in the absence of inhibitor (as illustrated in FIG. 4, upper panels and FIG. 5), demonstrating that active PR can be expressed at low levels without cytotoxic effects. In summary, FIG. 4 illustrates fluorescent microscopy analysis of cells transfected with pcDNA control (Invitrogen) and pcDNA-GFP-PR. GFP expression was analyzed 24 h post transfection. FIG. 4 Upper panels: untreated cells, FIG. 4 Lower panels: PR inhibitor, Saquinavir (NIH Reagents Program) was added at 0 and 24 h post transfection.

Figure 5:
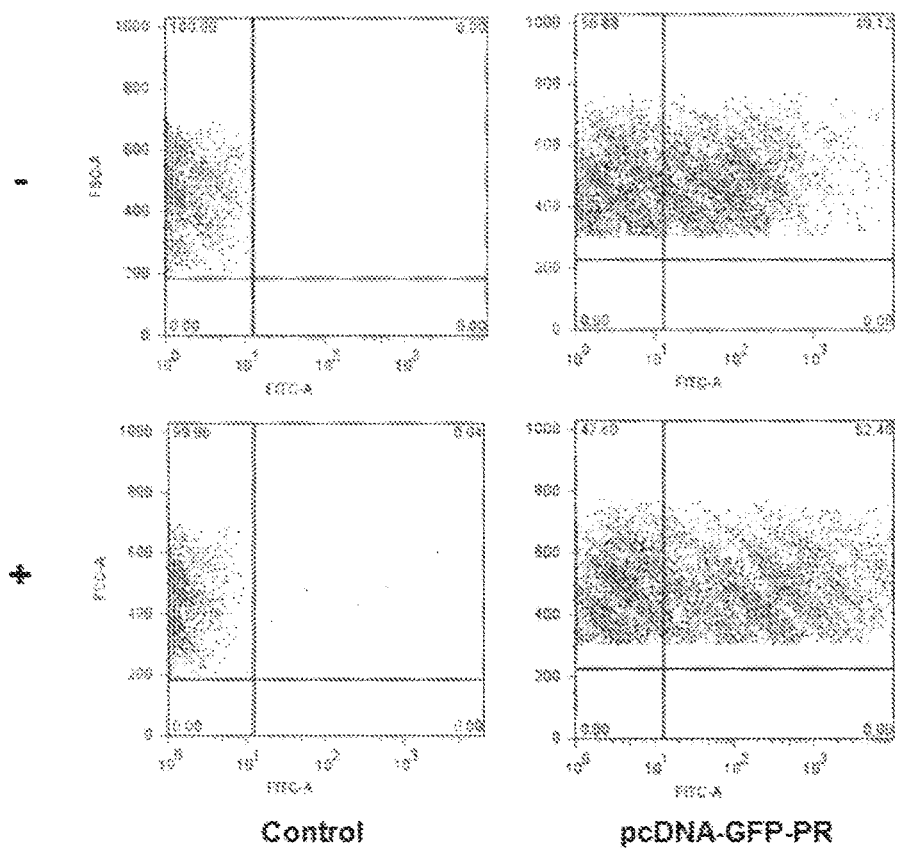
FIG. 5 graphically illustrates flow cytometry analysis of cells expressing PR-GFP fusion, as discussed in detail, below.

In summary, FIG. 5 graphically illustrates flow cytometry analysis of cells expressing PR-GFP fusion. Cells transfected with pcDNA (control) or pcDNA-GFP-PR fusions were collected 48 hr post-transfection and analyzed for GFP expression. FIG. 5 Upper panels: untreated cells. FIG. 5 Lower panels: Cells treated with Saquinavir.

Figure 6:
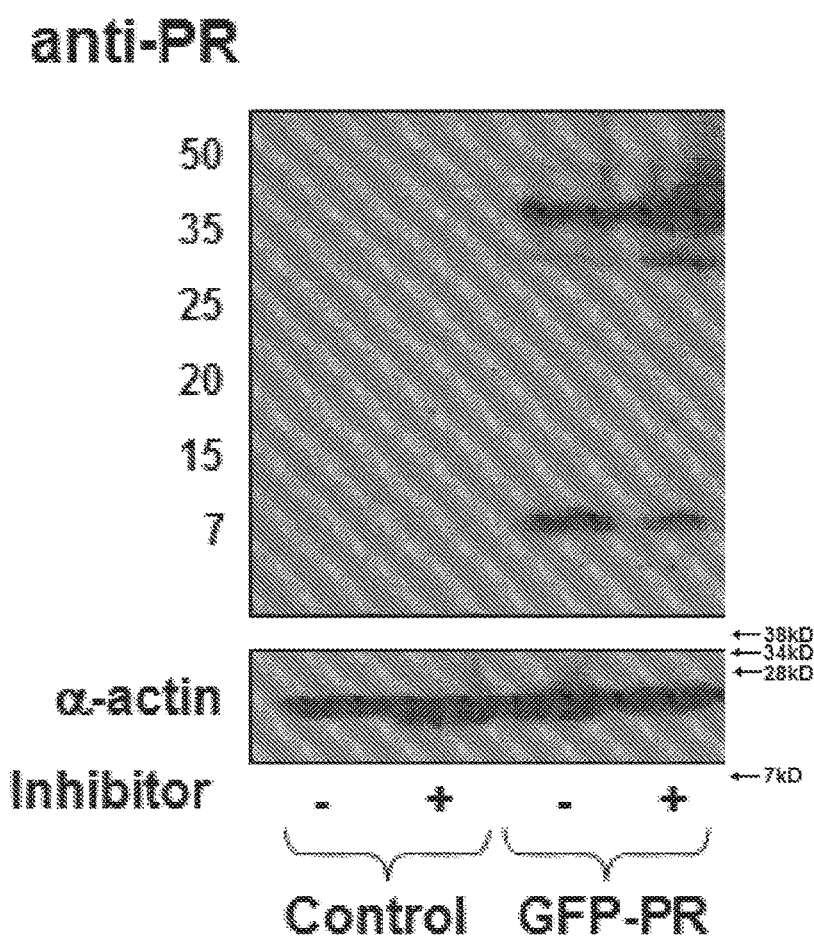
FIG. 6 illustrates a Western blot analysis of protease (PR) activity using the exemplary vector of FIG. 3, as discussed in detail, below.

In order to prove that those cells are actually expressing active PR, cells transfected with the pcDNA control or the N-terminal GFP fusion; GFP-PR were collected for Western blot analysis with anti-PR antibody (NIH Reagents Program). The presence of degradation products of autolysis when no inhibitors are added demonstrates that PR retains its activity, see FIG. 6. FIG. 6 illustrates a Western blot analysis of protease (PR) activity. 293T cells transfected with pcDNA (control) or pcDNA-GFP-PR fusions and either untreated or treated with Saquinavir (3 μM/ml) (e.g., INVIRASE™ or FORTOVASE™) at 0 h and 24 hr post-transfection) were collected for the blots. The expected autolysis products are shown. Upper panel: anti-PR antibody (NIH AIDS reagent). Lower panel: anti-alpha-actin antibody (Invitrogen, Carlsbad, Calif.) as loading control.

This exemplary scaffold of the invention, an adapted scaffold, is based on the same idea, but with an important difference. In one embodiment, when protease (e.g., PR) is active the FLAG or other detectable tag will be present on the surface and detectable e.g., by flow cytometry, whereas when protease (e.g., PR) is blocked or inactive, the FLAG will be lost and not expressed on the cell surface. This scaffold is based on the idea that generally, proteins to be expressed on the surface of the cell have a signal sequence (SS) on their N terminus that targets them to the endoplasmic reticulum (ER) and a transmembrane domain (TM) that retains them in the membrane.

Figure 7:
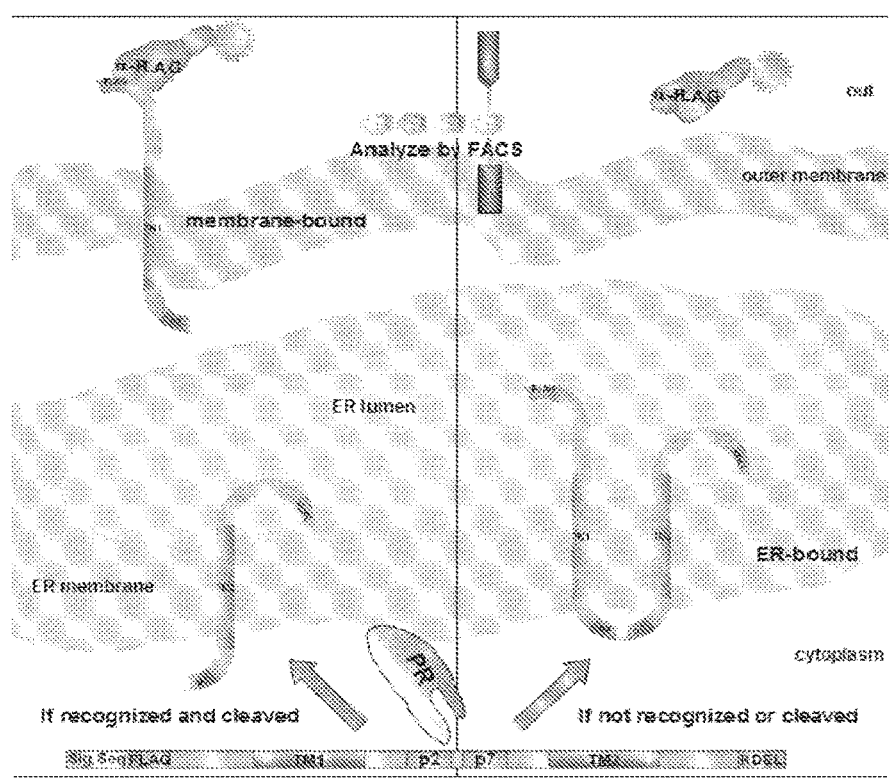
FIG. 7 illustrates an exemplary construct of the invention and an exemplary scenario for monitoring of protease, e.g., PR, activity, as discussed in detail, below: briefly, when protease, e.g., PR, is active (left panel of FIG. 7), the scaffold will be separated into two pieces, leaving the KDEL portion in the ER and freeing the FLAG tag portion to the membrane, where it will be detected by flow cytometry; if protease, e.g., PR, is blocked or inactive (right panel of FIG. 7), the entire scaffold will be retained in the ER, and as a consequence will not be detected on the surface.
Figure 8:
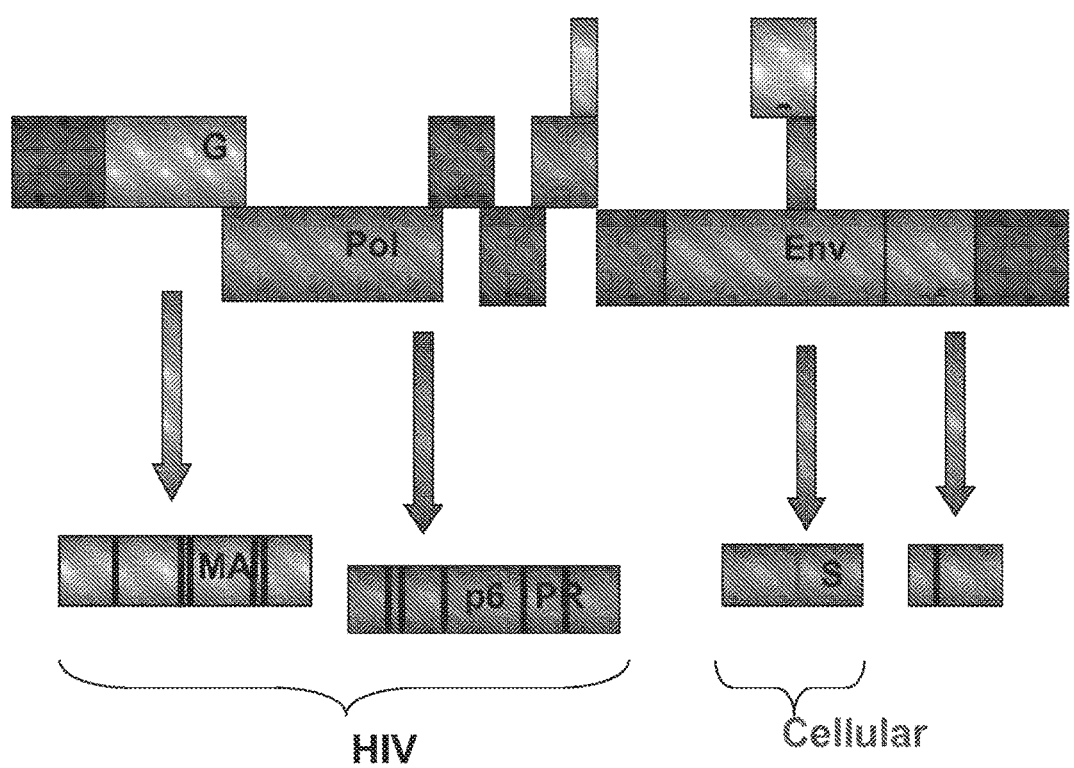
FIG. 8 illustrates HIV-1 Genome organization, as discussed in detail in Example 1, below.
Figure 9A:
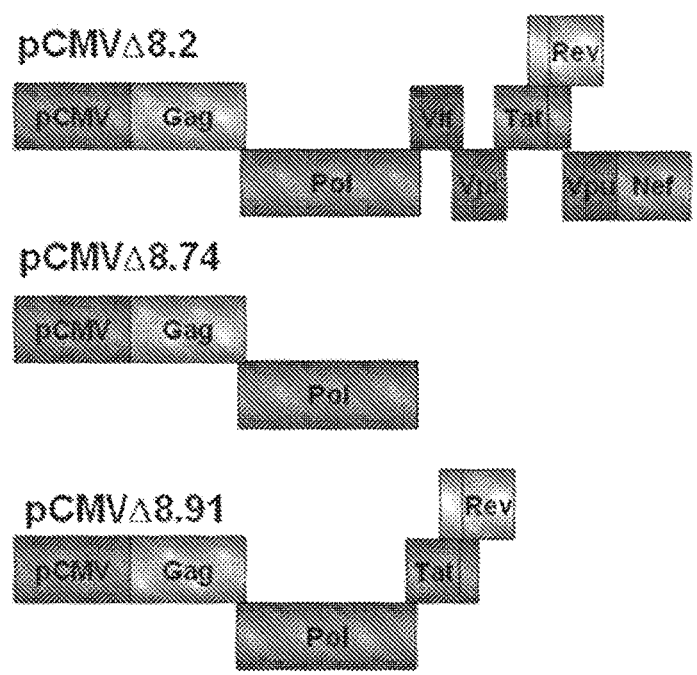
FIG. 9A illustrates exemplary plasmids pCMVD8.2, D8.7 and D8.91.
Figure 9B:
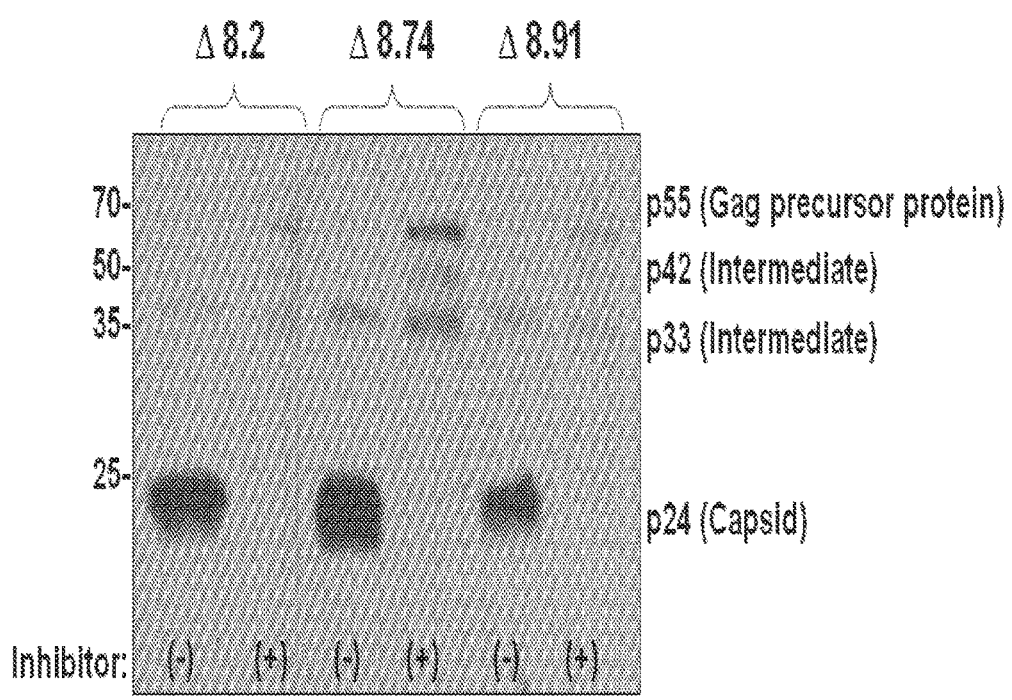
FIG. 9B illustrates a Western blot detecting the presence of p24; as discussed in detail in Example 1, below
Figure 10:
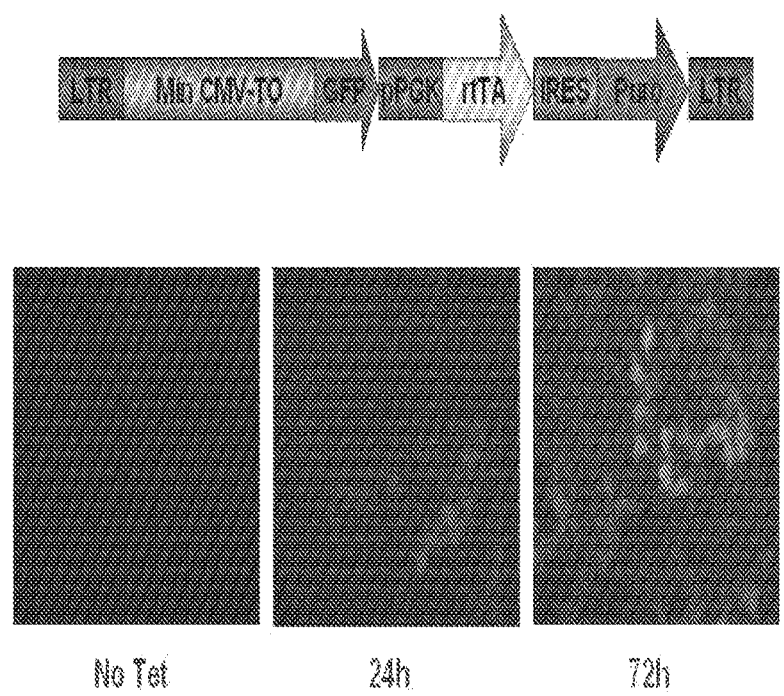
FIG. 10 illustrates an exemplary construct of the invention (LTR/Min CMV-TO/GFP/pPGK/rtTA/IRES/Puro/LTR) and the results of an inducible expression system of the invention, as discussed in detail in Example 1, below.
Figure 11:
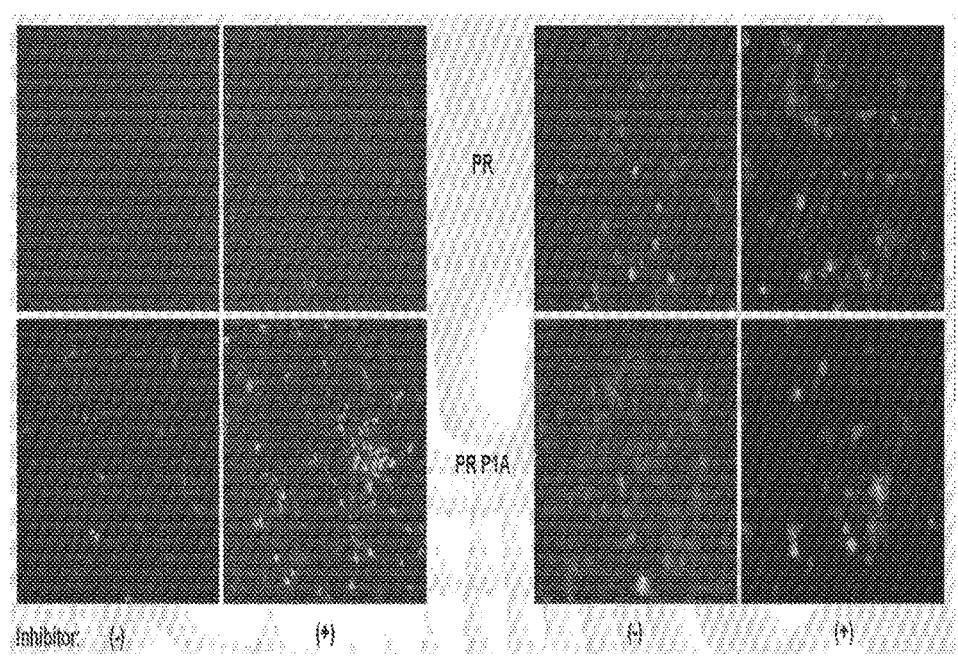
FIG. 11 and FIG. 12 graphically illustrate expression of exemplary HIV-1 PR/GFP fusion proteins of the invention: in order to detect PR expression, GFP was fused to the carboxy- (C-) or amino- (N-) terminus of PR, as discussed in detail in Example 1, below.
Figure 12:
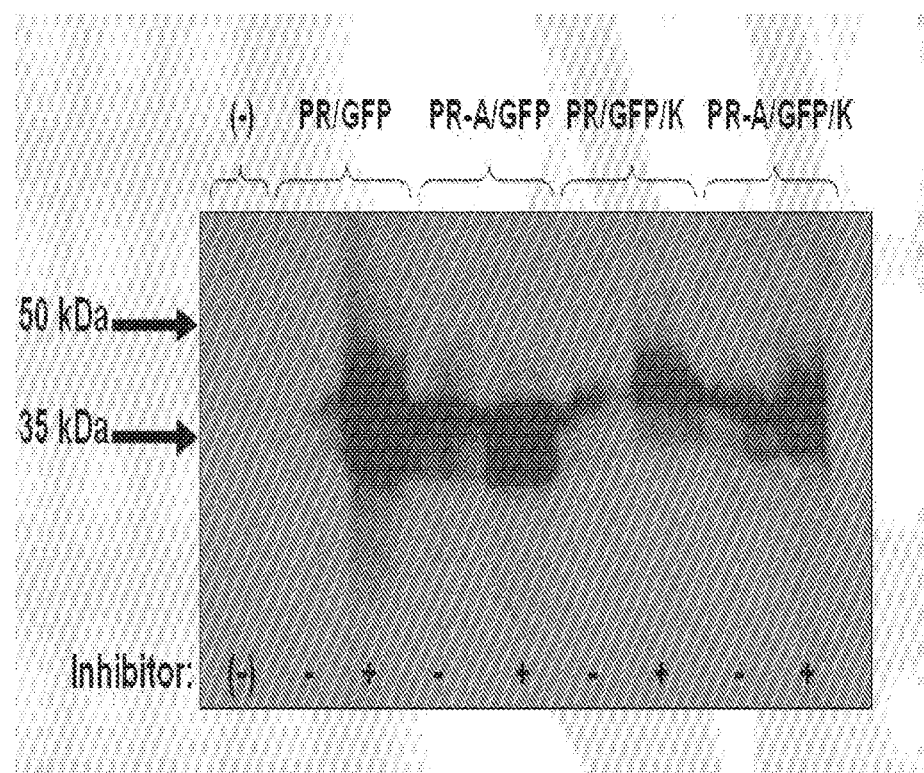

On the other hand, proteins that are retained in the ER, will have, in addition to the SS and the TM, an ER-retention signal such as the prototypic KDEL sequence. This sequence is known to have strong affinity to the KDEL receptor (SEQ ID NO:1), acing the luminal side of the ER. In one embodiment, the ER retention motif or KDEL (SEQ ID NO:1) motif is positioned in the scaffold protein such that when PR is active the scaffold will be separated into two pieces, leaving the ER retention motif-comprising or KDEL (SEQ ID NO:1) motif-comprising portion of the polypeptide in the ER and freeing the detectable moiety-comprising portion to the cell's extracellular membrane, and if PR is blocked or inactive, the entire scaffold polypeptide will be retained in the ER, and as a consequence will not be detected on the cell's extracellular surface FIG. 7 illustrates an exemplary construct of the invention that is based on CCR5 but has only the two first TM domains (rather than the original seven). As shown in the figure, the scaffold is further fused to a KDEL sequence at its C-terminus This scaffold allows, as mentioned earlier, to introduce a recognition sequence in the loop facing the lumen (for peptidases such as furin), or in the loop facing the cytoplasm (for viral proteases). FIG. 7 illustrates shows an exemplary scenario for monitoring of protease, e.g., PR, activity. When protease, e.g., PR, is active (left panel of FIG. 7), the scaffold will be separated into two pieces, leaving the KDEL portion in the ER and freeing the FLAG tag portion to the membrane, where it will be detected by flow cytometry. If protease, e.g., PR, is blocked or inactive (right panel of FIG. 7), the entire scaffold will be retained in the ER, and as a consequence will not be detected on the surface.

For example, the exemplary CCR5 engineered protein (or partial CCR5 as described here and in the figure) can be replaced by any other protein of choice or hybrid protein. For example, one exemplary embodiment comprises a hybrid protein comprising the N-terminus of the CD8 molecule or the CD8 molecule equivalent in mice (referred to as Lyt2), comprising its natural SS, and the C-terminus of the chemokine receptor CCR5 including only the last TM domain. In this embodiment, only requirement is that the resulting protein will, when cleaved, retain the KDEL-containing side in the ER and the N-terminus on the cell surface.

In alternative embodiments, any protein is used as scaffold (instead of the one exemplary protein described herein), provided that by adding a KDEL sequence at the C terminus the polypeptide will be retained it in the ER, unless separated from the N-terminus.

In this embodiment, a p2/p7 recognition site is imbedded in the cytoplasmic loop of the scaffold, as PR is known to be active in this environment.

In alternative embodiments, the scaffold is engineered for the search of viral PR inhibitors (active in the cytoplasm) and/or for proteases/peptidases active in the lumen of the ER. In one embodiment, the loop facing the luminal face of ER is substituted by a recognition site cleaved by cellular peptidases. This can include the gp120/gp41 boundary, known to be cleaved by peptidases such as furin. These enzymes are known to be active in the inner side of the ER, that is its luminal face, making this exemplary scaffold adaptable for the search of HIV envelope processing and for transport inhibitors.

In alternative embodiments, the invention provides methods and compositions, including chimeric recombinant proteins, nucleic acids that encode them, and cells and kits comprising them, to screen for compositions, e.g., small molecule drugs, that can modulate, e.g., inhibit or enhance, any enzyme, e.g., protease or HIV-1 protease (PR), or NS2/NS3 or NS3/NS4A protease of HCV, or any viral protease, including retroviral (e.g., HIV) proteases, and/or any transport and/or structural protein.

In one embodiment, the invention provides cells and cell-based assays for monitoring the activity of activity an HIV-1 protease (PR), which is an aspartyl protease. In one embodiment, these cells and cell-based assays are used to screen for and identify novel PR inhibitors. In one embodiment, assays of the invention effectively couple the surface (extracellular) expression of a protein used as a scaffold (a scaffold protein), with the activity of the viral PR. p2/p7 of the HIV-1 strain HXB2 (taken as the prototype genome) is part of that virus's viral proteome, and contains one of the natural targets for the recognition and cleavage site of PR.

In one embodiment, the scaffold is engineered for its conditional expression on the surface of a cell, e.g., a yeast or a mammalian cell. For that purpose, in one embodiment, the scaffold is fused to a signal sequence to enable efficient transport, and a transmembrane domain (e.g., an Lyt2, the murine CD8 molecule, and the like) is used to enable subsequent insertion in the cell membrane. A tag such as a FLAG tag is added to the scaffold downstream of the signal sequence for detection, e.g., for antibody detection, e.g., through flow cytometry or equivalent visualization.

In one embodiment, the assay co-expresses both the scaffold protein and the HIV-1 PR, which, if active, will bind to and cleave the scaffold.

In one aspect, both scaffold and protease are co-expressed in a lymphocyte, e.g., a T cell or T cells, e.g., a SupT1 T-cell, in an inducible off/on-based vector system (e.g., activated upon addition of tetracycline or doxycycline). Inducible expression of PR helps avoid its possible cytopathic effects. Inducible expression of the scaffold is necessary as PR will only be able to prevent surface expression of newly synthesized intact scaffold, as the pre-inserted scaffold would not be removed from the cell surface by PR.

Kits

The invention provides kits comprising compositions and instructions for use of the invention. The kits can include: cells comprising nucleic acids encoding the chimeric polypeptides of the invention (the "scaffold proteins") and/or vectors comprising these nucleic acids, or chimeric polypeptides of the invention, transfecting agents, transducing agents, instructions (regarding the methods of the invention), or any combination thereof. As such, kits, cells, and libraries of compounds are provided herein.

Cell-Based Methods and Multiplexed Systems

In alternative embodiments, the invention provides cells and cell-based assays and multiplexed systems for monitoring the activity of activity of proteases, e.g., an HIV-1 protease (PR), which is an aspartyl protease. In one embodiment, these cells and cell-based assays are used to screen for and identify novel PR inhibitors ("PIs"). In one embodiment, the invention provides methods and compositions, including chimeric recombinant proteins, nucleic acids that encode them, and cells and kits comprising them, to screen for compositions, e.g., small molecule drugs, that can modulate, e.g., inhibit or enhance, any enzyme, e.g., protease or HIV-1 protease (PR), or NS2/NS3 or NS3/NS4A protease of HCV, or any viral protease, including retroviral (e.g., HIV) proteases.

In one embodiment, the invention provides assays and multiplexed systems in T cells to monitor the proteolytic activity of a protease, e.g., the HIV-1 protease (PR). The assay is based on an inducible Gal4 HIV-1 PR fusion which binds to upstream activation sequences and activates a reporter gene only in the presence of a PR inhibitor ("PI"). The assay was developed through retroviral technology in T-cells to mimic the natural environment of HIV infection.

In one embodiment, the invention provides clones which, when activated, express eGFP as a biosensor of PR activity. This assay of the invention has a robust and reliable readout that relies on green fluorescence, making it ideal for high-throughput screening utilizing flow cytometry. Thus, the assay of the invention will greatly facilitate the search for novel peptide- and chemical-compound-based PIs in T-cells.

In one embodiment, the invention provides a simple, rapid and straightforward method and multiplexed systems for monitoring a protease, e.g., PR, activity to facilitate the search for novel inhibitors/competitors of the protease that could lead to new therapeutics, e.g., to treat HIV (e.g., AIDS).

In one embodiment, assays of the invention are based on the classical Gal4-UAS system, a broadly utilized system for the analysis of gene expression. The yeast Gal4 protein represents a prototypic transcription factor consisting of two separate domains: An N-terminal DNA-binding domain (DBD: aa 1-147) and a C-terminal Transactivation domain (TAD: aa 768-881)'. The Gal4 protein binds to consensus Upstream Activation Sequences (UAS's) via its DBD and activates transcription of downstream genes through its TAD. However, when the two Gal4 domains are separated, neither half of the protein can independently serve as a functional transcription factor.

Murray (1993) Gene 134(1):123-128, demonstrated the ability for HIV-1 PR fused within Gal4 to auto-catalytically remove itself, leaving behind the two non-functional domains of Gal4. When the PR/Gal4 fusion protein is mutated at the catalytic site, however, or is in the presence of an inhibitor, the fusion protein remains intact, retaining its ability to bind to UAS through the DBD and activate transcription through TAD. In alternative embodiments, this property is incorporated into this invention to express a reporter gene in an inversely proportional manner to PR activity and serve as template for this assay.

In alternative embodiments, assays and multiplexed systems of this invention are based on the expression of the PR/Gal4 fusion as an inducible fusion through a Tet-On system (e.g., in one embodiment, adapted from Clontech, Takara Bio Inc., Shiga, Japan), thus drastically reducing its possible toxic side effects. In this embodiment, the reverse tetracycline transactivator (rtTA) is utilized, allowing for the induction of PR/Gal4 expression only upon addition of tetracycline (Tet) or doxycycline (Dox). The readout; eGFP expression, will appear only when PR/Gal4 expression is induced in the presence of inhibitor. Moreover, all the elements of the assay have been constructed in retroviral vectors for their stable expression in mammalian cells. In alternative embodiments, the assays of the invention are designed for use in lymphocytes such as T cells to facilitate the high-throughput screening for novel inhibitors in a more natural milieu.

In alternative embodiments, assays of the invention are adapted such that the cells carry several enzyme, e.g., protease or HIV-1 protease (PR), or NS2/NS3 or NS3/NS4A protease of HCV, mutant variants, including for example the most prevalent PR mutant shown to be resistant to FDA-approved inhibitors. In alternative embodiments, clones comprising different enzymes (e.g., PRs), when inhibited, activate the transcription of a different fluorescent marker. Accordingly, in alternative embodiments, the assays of the invention are adapted as multiplexed systems.

We have proved the clones of this invention to be very valuable for the screening of inhibitors against the specific PR used in the assay; from the HXB2 consensus T-tropic strain. Due to the high mutational rate it is crucial to adapt the assay to as many protease variants as possible—and the assays and multiplexed systems of the invention are adaptable to multiple protease variants. In alternative embodiments, assays of the invention are adapted to an array of proteases that include the most prevalent protease variants resistant to the existing FDA-approved PIs, In alternative embodiments, these assays are configured as multiplexed systems of the invention.

In alternative embodiments, assays of the invention are adapted to mutations in at least 18 different positions within the 90 amino-acids of PR which have been described to confer drug resistance. In order to adapt the assay for multiplex analysis, we chose the three most prominent variants: L90M, I54V and V82A. For this purpose, in alternative embodiments, L90M, I54V and V82A are introduced between the Gal4 DBD and TA domains. In alternative embodiments, each PR variant when inhibited will activate a different fluorescent protein. While the wild-type variant described in FIG. 6 data activates e-green fluorescent protein, or eGFP (excited with the 488 nm blue laser, the other mutants will activate an e-cyan fluorescent protein (or eCFP, using a 405 nm violet laser), and mOrange or mCherry (561 nm yellow laser). This will allow screening for compounds that inhibit all, some or one PR variant at a time, based on the specific fluorescence observed. Importantly, other clones expressing a different set of mutant PR will be produced in the future, when necessary.

In alternative embodiments, assays of the invention are adapted to multiplexed formats with various enzyme (e.g., PR) mutants/variants and reporter combinations to simultaneously detect enzyme (e.g., PR) resistance to individual hits. In alternative embodiments, assays of the invention are adapted to Luminescence/plate reader-based formats. In alternative embodiments, assays of the invention are adapted to screening peptide and chemical-compound libraries.

Cell-Based Assays for the Identification of Compositions that Inhibit Envelop Processing In alternative embodiments, the invention provides cells and cell-based assays to screen for compositions, e.g., small molecules or drugs, that inhibit or modify the activity of enzymes such as calcium-dependent protein convertases such as furin involved in HIV envelop protein processing, including cleavage of the HIV gp160 envelope precursor, resulting in gp120 and gp41 envelope products.

In one embodiment, the invention provides assays to monitor the HIV-1 envelope processing process. This process is based on the cleavage of the gp160 envelope precursor, resulting in gp120 and gp41 envelope products. In one embodiment, the assay of the invention is based on the engineering of a receptor protein scaffold (or detection moiety) construct that will be targeted to the ER and transported to the cell surface only when the protein scaffold was efficiently cleaved by a gp160 envelope precursor processing enzyme such as a calcium-dependent protein convertase, e.g., prohormone convertase-1 ("PC1"), furin and/or similar enzymes (e.g., any member of the subtilisin/ kexin family of proprotein convertases), some of which reside in the ER-trans Golgi network.

In one embodiment, this is attained by fusing a KDEL (SEQ ID NO:1) retention signal, known to be recognized and bound by KDEL-receptors in the ER lumen, at the carboxy-terminus (C-terminus) of the scaffold (or detection moiety). An enzyme (e.g., furin, PC1, a member of the subtilisin/kexin family of proprotein convertases, and the like) recognition/cleavage site is introduced between the scaffold and the KDEL (SEQ ID NO:1) sequence. When enzyme (e.g., furin, PC1, etc.) processing is blocked or inhibited, the receptor will move from the ER to the trans-Golgi and recycled back to the ER, due to the presence of the KDEL (SEQ ID NO:1) sequence. In contrast, when the enzyme (e.g., furin, PC1, etc.) is active, it will cleave its recognition site and separate the KDEL (SEQ ID NO:1) sequence from the scaffold protein, which will then be allowed to travel to the surface.

In one embodiment, assays of the invention facilitate the monitoring of enzyme (e.g., furin, PC1, etc.) activity based on the presence or absence of the scaffold (including any detection moiety) on the surface of the cell. In alternative embodiments, fluorescent-coupled antibodies against a tag (e.g., FLAG in our example) can be used to analyze cells by flow cytometry or similar or equivalent detection system.

Assays of the invention can greatly facilitate the discovery of novel gp160 processing inhibitors, including screening for any composition, including a small molecule, protein, carbohydrate and the like that can act as a partial or complete gp160 processing inhibitor.

In one embodiment, assays of the invention are T-cell-based; in this embodiment the assay represents the natural milieu for HIV, e.g., HIV-1, infection.

In one embodiment, flow cytometry allows utilization of assays of this invention in a high-throughput manner. Thus, in alternative embodiments, assays of the invention can be used for the screening of chemical compound (e.g., small molecule) libraries aimed at finding novel inhibitors of gp160 processing. In one embodiment, the nature of the assay as cell-based will discriminate between drugs that target Furin (which would be detrimental to the cell), and those that target the specific cleavage of the gp120/41 boundary by Furin (or similar enzymes).

In one embodiment, the CCR5 receptor, a naturally present receptor in macrophages and other cell types, is engineered as a scaffold (e.g., detection moiety) to satisfy the needs of this assay. In this exemplary embodiment, the scaffold will be comprised of two transmembrane domains (TMs) of the CCR5 receptor fused to a FLAG molecule on the N-terminal region. We have chosen TM1 and TM2 from the original seven TMs of CRR5, but any TM could be used instead. The KDEL (SEQ ID NO:1) ER retention signal will be fused to the C-terminus in order to keep the scaffold bound to the ER membrane, at the luminal face.

In one embodiment, the gp120/gp41 boundary, including the recognition/cleavage site REKRA (SEQ ID NO:14) (amino-acids 515-519) and seven additional amino-acids at both sides (AKRRVVQREKR (SEQ ID NO:15) AVGI-GALF (SEQ ID NO:16), which represents amino-acids 502-519 of the HXB2 HIV-1 strain), are introduced into this exemplary chimeric protein of the invention.

Figure 13:
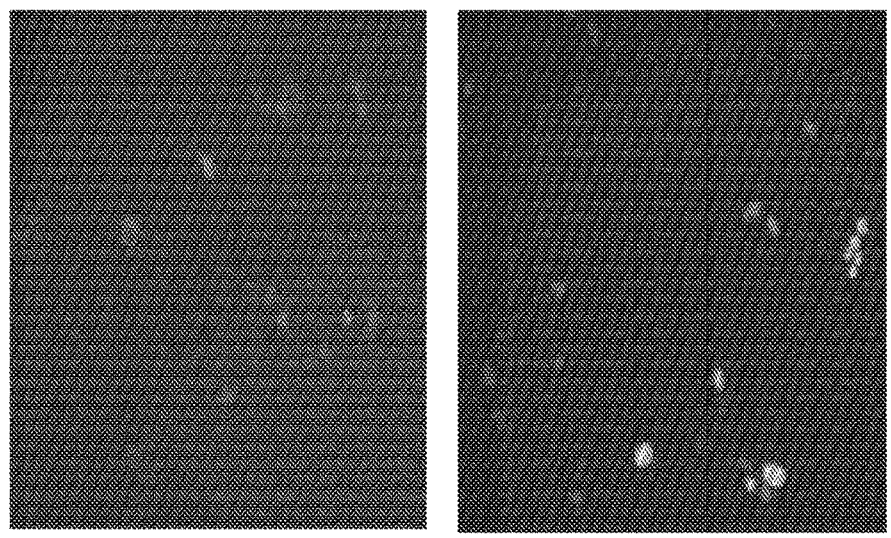
FIG. 13 illustrates targeting HIV-1 PR to different cellular compartments: PR was targeted to the nucleus by adding a nuclear localization signal to the C terminus using the exemplary vector, as discussed in detail in Example 1, below.

While the invention is not limited by any particular mechanism of action, if cellular proteases/peptidases, such as Furin or PC1, resident in the ER lumen, cleave the scaffold, the receptor will travel to the cell surface and be recognized with a detection system, e.g., a flow cytometry. If, in contrast, the protein is not cleaved, the scaffold level on the cell surface will be extremely diminished or completely abolished. As a control, a similar scaffold that lacks the cleavage site can be used to ensure expression in the ER but not on the surface. The introduction of the gp120/41 boundary can be performed with the addition of restriction enzyme cleavage sites on both sides of the sequence, allowing for easy replacement of other sequences in the future. This will also facilitate the exploration of other consensus sequences found to be recognized by Furin, or similar enzymes, such as the sequence within the V3 loop of gp120.

Though HIV envelope is known to be cleaved in the trans Golgi network, in one embodiment the scaffold is localized to the ER through the KDEL (SEQ ID NO:1) signal because the mechanism KDEL receptor-bound proteins are known to travel to the Golgi and subsequently recycled into to the ER.

While one exemplary embodiment comprises a protein scaffold based on CCR5, CCR5 was chosen only as a proof of concept—in alternative embodiments any protein, mimetic, peptidomimetic or equivalent scaffold can be used.

In alternative embodiments the assays of the invention are adapted to virtually any construct that behaves as described herein, and thus comprises, from N- to C-terminus:

a signal sequence for ER targeting, a tag for antibody recognition, two transmembrane domains that will span the ER membrane, with an extra loop at the ER luminal face a Furin or similar enzyme recognition/cleavage site spanning a segment of the gp120/41 boundary, facing the ER lumen a KDEL (SEQ ID NO:1) sequence for ER retention.

While one exemplary embodiment comprises introduction of only a short sequence of the gp120/gp41 boundary that contains the consensus Furin recognition/cleavage site (ten amino-acids in length), in alternative embodiments additional recognition sites of different lengths could be introduced instead. In alternative embodiments assays of the invention use two known consensus sequences of the HXB2 HIV strains gp120.gp41 boundary sites: AKRRVVQREKRAVGIGALF (SEQ ID NO:17) (recognition/cleavage site in bold). Other strains are used as well.

The different scaffolds used in various embodiments of this invention can further our understanding of protein transport through the ER to the cell surface.

In alternative embodiments the cell-based assays are used in T-cells through retroviral technology. T-cells are a cell type readily infected by HIV, thus providing an art-accepted model that mimics natural infection. In alternative embodiments, the assay is used in lymphocytes, e.g., T-cells—a cell type readily infected by HIV through retroviral technology.

In alternative embodiments these cell-based assays facilitate the discovery of novel drugs aimed at HIV-1-envelope processing rather than the host protease, thus avoiding toxic side-effects, e.g., avoiding cytotoxic side-effects.

In alternative embodiments, assays of the invention monitor HIV-1 envelope processing based on the cleavage of the gp160 envelope protein precursor, resulting in gp120 and gp41 products using a scaffold protein that will not be retained on the cell-surface when processing is blocked or inhibited. In alternative embodiments, the processing, or inhibition of processing, is detected by flow cytometry allowing the observer to discriminate between active and inactive envelope processing.

The invention will be further described with reference to the following examples; however, it is to be understood that the invention is not limited to such examples.

EXAMPLES

Example 1

Exemplary Assays of the Invention

The invention provides compositions and assays for screening for protease inhibitors, e.g., viral protease inhibitors such as HIV-1 protease (PR) (an aspartyl protease) inhibitors. PR is required for the efficient processing of the Gag and Gag-Pol precursor polyproteins; a critical step in the viral life cycle. In alternative embodiments, the invention provides compositions and assays for: (1) Discerning the effects of protease, e.g., PR, on signaling cascades of the host cell, and (2) Developing novel cell-based assays to enable screening of peptide libraries for the search of novel protease, e.g., PR, inhibitors. In alternative embodiments, a protease, e.g., PR, is expressed as a fusion protein in the presence of limiting levels of inhibitors, in different cellular compartments and in an inducible manner.

FIG. 8 illustrates HIV-1 Genome organization: HIV-1 has three structural genes (Gag, Pol and Env) and six regulatory genes. Both Gag and Pol, expressed as Gag-Pol precursor are cleaved by the HIV PR, while Env is cut by the cellular protease furin. PR autocatalytically cleaves itself from the precursor polyprotein. HIV PR therefore determines the infectious potential of the virus, as its activity is crucial for the conversion of the immature virion to the mature, infectious form.

FIG. 9 illustrates an indirect confirmation of HIV-1 PR activity: 293T cells were transfected with the plasmids pCMVD8.2, D8.7 and D8.91 (illustrated in FIG. 9A) with and without inhibitors. Ritonavir, a known PR inhibitor, was added to cells at a concentration of 3 mM/ml every 24 hours. Cells were extracted 48 hours post-transfection and analyzed for capsid (p24) expression. The presence of p24, detected by Western blot, as illustrated in FIG. 9B, is therefore an indicator of PR activity.

FIG. 10 illustrates an exemplary construct of the invention (LTR/Min CMV-TO/GFP/pPGK/rtTA/IRES/Puro/LTR) and the results of an inducible expression system of the invention: in one embodiment, for the expression of low levels of PR in mammalian cells, a tetracycline (Tet) inducible system is used. To corroborate the efficiency of the exemplary construct and system of the invention, Green Fluorescent Protein (GFP) was used as a marker for inducible expression. Fluorescence intensity was monitored in 293T cells transfected with the Tet inducible HIV-based self-inactivating vector that allows for the regulated expression of the gene of interest. Importantly, this exemplary vector allows for the controlled expression of PR, which may be essential in order to avoid PR-mediated cytotoxicity.

FIG. 11 illustrates the expression of two exemplary HIV-1 PR/GFP fusion proteins of the invention as illustrated in the schematics, and in summary:

FIG. 11A: expression of pCMV-PR/P1A/D25N-GFP=>pSV40-Zeo;

FIG. 11B: expression of pCMV-GFP-PR/P1A/D25N=>pSV40-Zeo. In order to detect PR expression, GFP was fused to the C (left panels) or N (right panels) terminus of PR. In addition to wild-type PR (top of panels), a mutant form; PIA was also expressed in 293T in a similar fashion (Bottom of Panels). This mutation may increase PR flexibility.

FIG. 12 illustrates a Western Blot of PR/GFP fusion proteins with anti-PR antibody. A KDEL sequence was fused for further expression in the ER (last 4 lanes).

FIG. 13 illustrates targeting HIV-1 PR to different cellular compartments. PR was targeted to the nucleus by adding a nuclear localization signal to the C terminus using the exemplary vector: pCMV-PR/P1A/D25N-GFP/NLS=>pSV40-Zeo. Nuclear expression of PR will allow co-localization with one of our scaffold proteins (GFP based scaffold, see FIG. 16). Moreover, expressing PR in a different cellular compartment may decrease its cytotoxic effects without affecting its catalytic activity.

Figure 14:
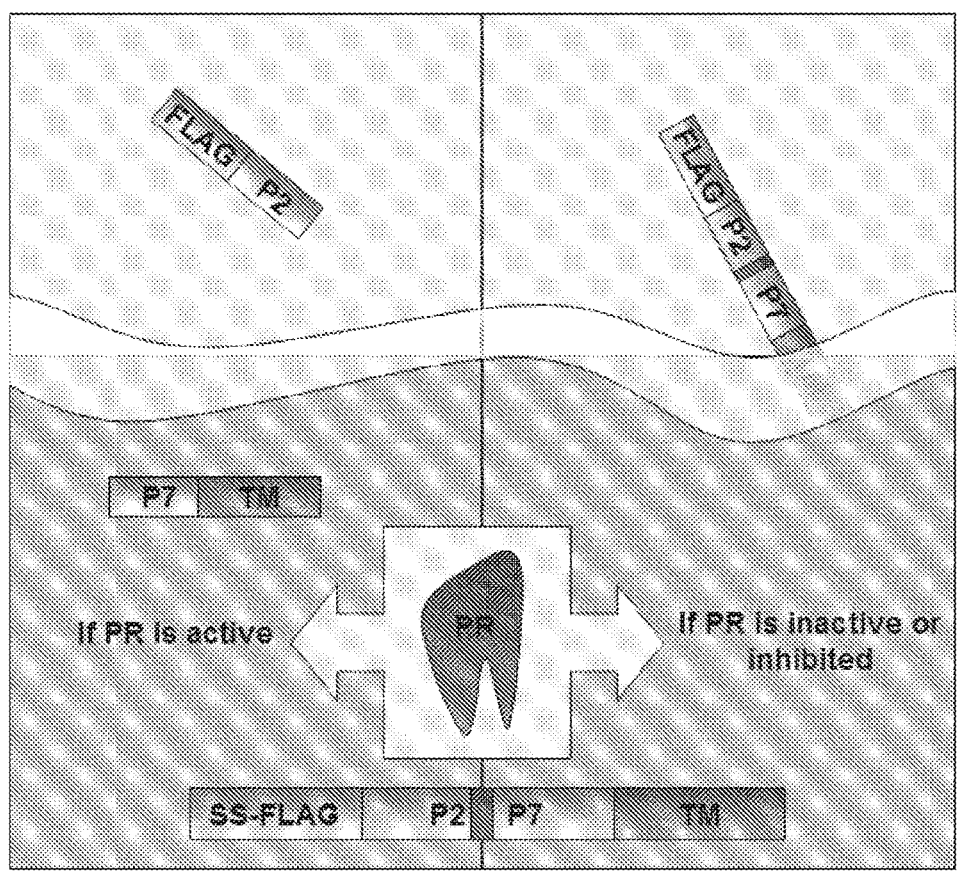
FIG. 14 illustrates a schematic representation of an exemplary scaffold of the invention and an exemplary protease (e.g., PR) assay based on surface expression of the scaffold protein, as discussed in detail in Example 1, below.

FIG. 14 illustrates a schematic representation of an exemplary scaffold of the invention and an exemplary protease (e.g., PR) assay based on surface expression of the scaffold protein. The scaffold (SS-FLAG/P2/P7/TM) was engineered to be expressed on the cell surface and consists of an HIV-1 sequence with one of the PR recognition/cleavage sites. This cleavage site has the highest affinity to PR and is the first one to be cleaved. The design of the scaffold allows for surface expression only when protease (e.g., PR) is inactive or inhibited. Surface expression of the scaffold can then be easily identified by flow cytometry. This assay serves as a platform for high throughput screening of peptide libraries targeted against protease (e.g., PR).

Figure 15A:
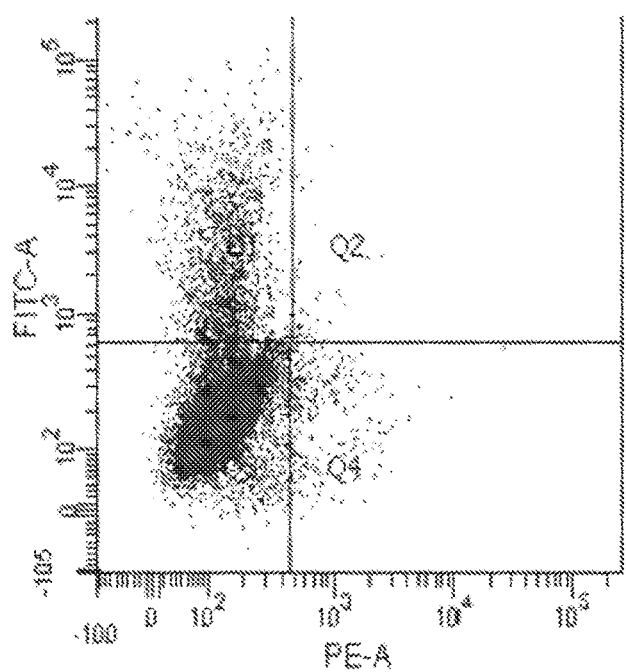
FIG. 15A illustrates results for the control construct and FIG. 15B illustrates results for the scaffold protein construct; as discussed in detail in Example 1, below.
Figure 15B:
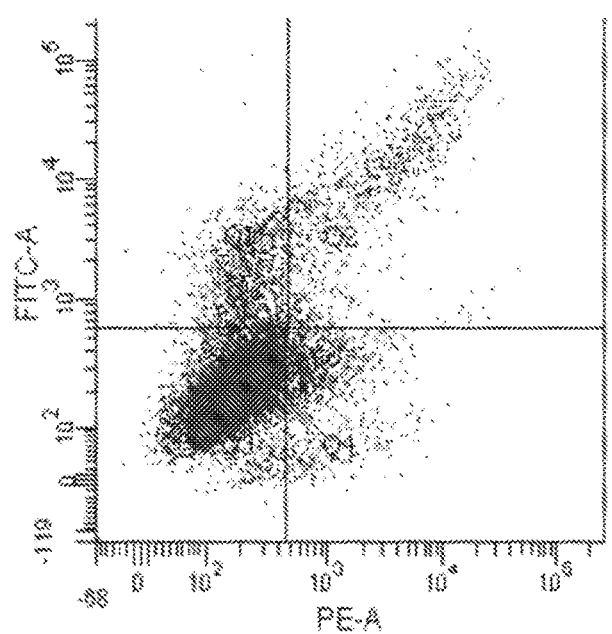

FIG. 15 illustrates two exemplary constructs of the invention: pCMV/GFP=>Zeo, and pCMV/GFP=>SS-FLAG/P2-P7/TM=>Zeo; and flow cytometry analysis of the expression of these two scaffold proteins on the surface of 293T cells. Cells were transfected with either a control GFP vector (pCMV/GFP=>Zeo) or a scaffold protein construct of the invention (pCMV/GFP=>SS-FLAG/P2-P7/TM=>Zeo). Cells were then stained with anti-FLAG-PE antibody and analyzed by flow cytometry; FIG. 15A illustrates results for the control construct and FIG. 15B illustrates results for the scaffold protein construct. The double-positive population expressing the scaffold can be enriched through sorting.

Figure 16:
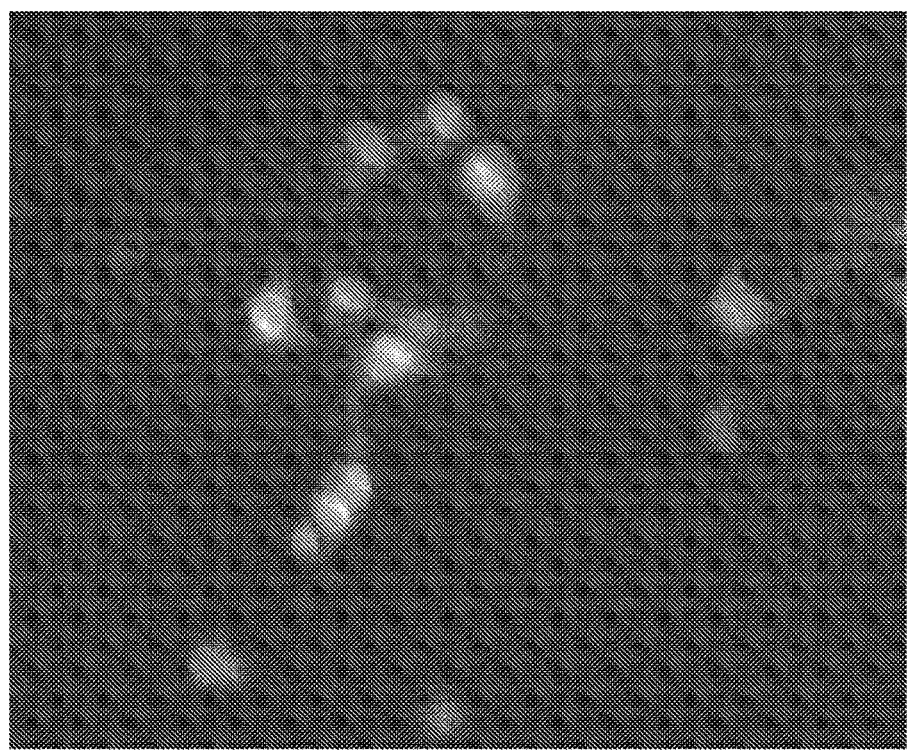
FIG. 16 illustrates the results of use of an exemplary construct of the invention, pCMV/GFP/PCS/GFP-NLS=Zeo, where GFP as a biosensor of PR activity; as discussed in detail in Example 1, below.

FIG. 16 illustrates the results of use of an exemplary construct of the invention, pCMV/GFP/PCS/GFP-NLS=Zeo, where GFP as a biosensor of PR activity. In this embodiment, the surface expression scaffold assay is based on GFP. The PR cleavage site (PCS) has been introduced into one of the loops of GFP. This construct was then transfected into 293T cells, corroborating that fluorescence was maintained. Thus, in this embodiment, the GFP is expressed in the absence of PR. In contrast, cleavage by PR will result in truncation of the GFP into two halves and thus, loss of fluorescence. It has been shown that the reconstitution of truncated GFP products can restore fluorescence. Therefore, we have fused a nuclear localization signal to the C terminal half to isolate it from the N terminal half, thus preventing the reconstitution of fluorescence. This exemplary scaffold can serve as an indicator of PR activity.

Figure 17:
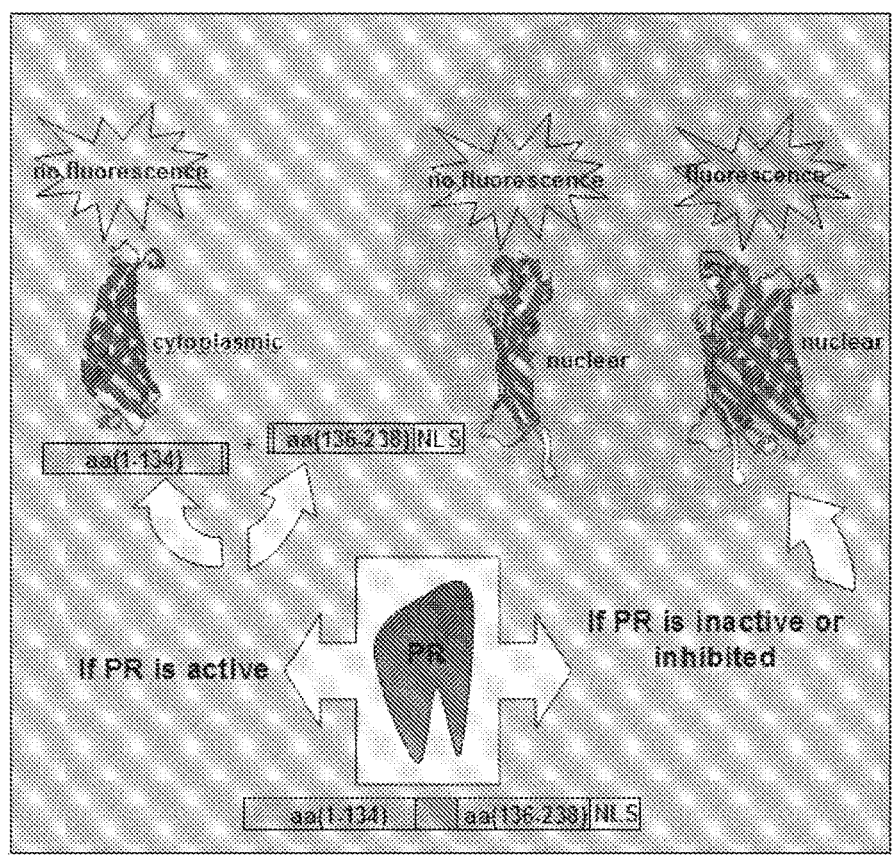
FIG. 17 illustrates an exemplary construct of the invention where a nuclear localization signal is separated by a detectable moiety, e.g., a fluorescent protein, by a protease cleavage site; as discussed in detail in Example 1, below.

FIG. 17 schematically illustrates an exemplary construct of the invention (aa1-134/protease cleavage site/aa136-238/NLS) where a nuclear localization signal (NLS) is separated by a detectable moiety, e.g., a fluorescent protein, by a protease cleavage site, and the protease cleavage site is spliced into the middle of the fluorescent protein; thus, if the protease (e.g., a PR) is inactive or inhibited, the NLS retains the detectable moiety in the nucleus, while an active protease completely eliminates the fluorescent signal.

Figure 18:
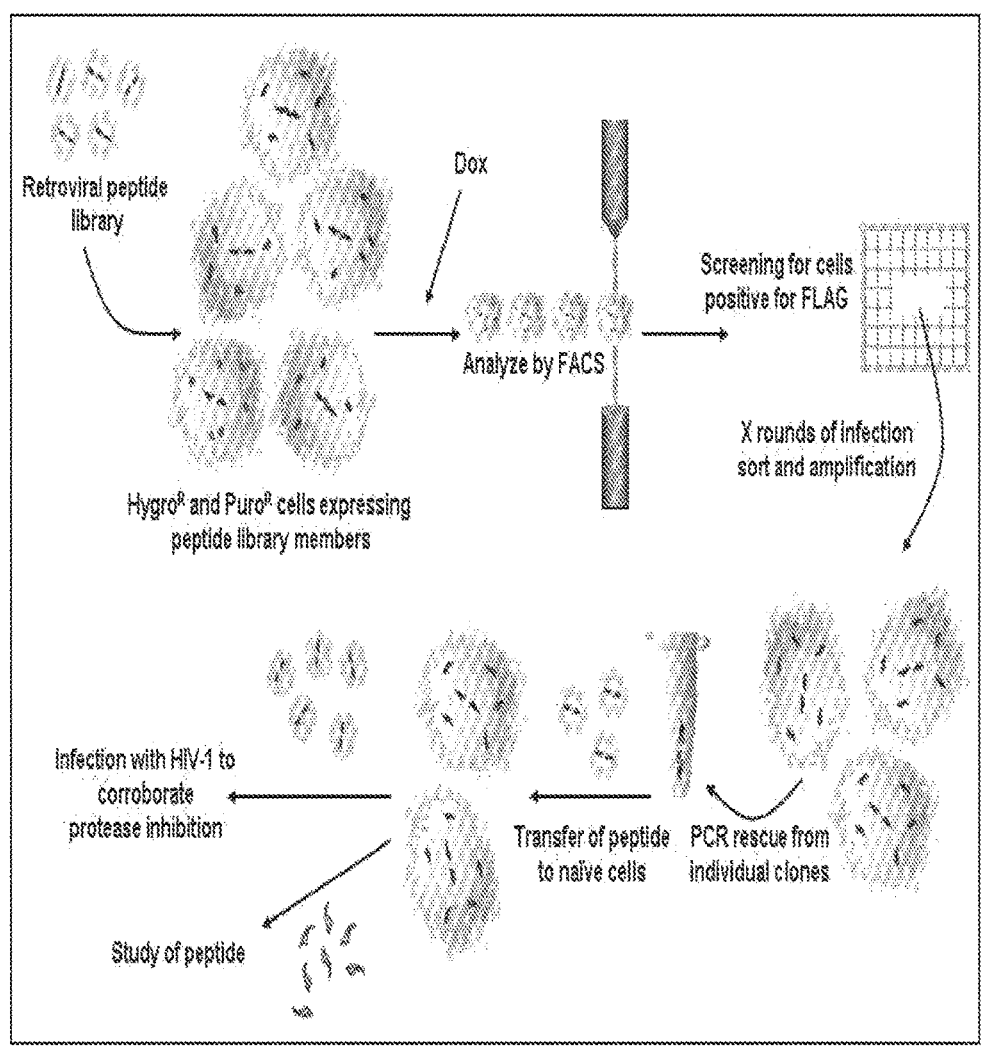
FIG. 18 schematically illustrates an exemplary assay of the invention for screening peptide libraries; as discussed in detail in Example 1, below.

FIG. 18 schematically illustrates an exemplary assay of the invention. In this embodiment, a random peptide library, the scaffold protein, and PR is co-transfected into SupT1 cells. Cells can be co-transfected with PR and the scaffold protein and, in one embodiment, expressed in an inducible manner, e.g., a Tet inducible manner. Cells selected for both PR and scaffold can be transfected with a random peptide library (e.g., a retroviral peptide library, as in the schematic).

Using FACS analysis, cells that are positive for the scaffold can be selected and cloned. In one inducible manner, the peptide will then be rescued by PCR and reintroduced into naïve cells to corroborate its inhibitory effect. The peptide can then be the basis for the development of peptidomimetic anti-viral drugs.

Conclusions

In alternative embodiments, the invention provides compositions and assays to measure the activity of proteases, e.g., viral proteases, such as HIV-1 PR, a difficult protein to study due to its instability and possible cytotoxic effects. In alternative embodiments the invention expresses PR in a stable manner for a cell based assay aimed at finding peptides that inhibit PR, as well as discerning its effect on signaling cascades. In alternative embodiments, GFP fusion proteins were constructed. These products allow determination of the sub-cellular localization of HIV-1 PR. Moreover; we have also shown that PR can be targeted to different organelles. This is important as it will enable decreasing its toxicity, without affecting the catalytic activity of PR.

In alternative embodiments, the invention elucidates the effects of PR on target cells. In alternative embodiments the invention PR is expressed in a Tet-inducible manner to help in elucidating the signaling cascades influenced by PR, as turning on/off the expression of PR can avoid cytotoxic effects and thus become the perfect model for studying signaling.

In alternative embodiments the invention provides assays for determining PR activity because PR is one of the main targets for antiviral therapy. In alternative embodiments PR is expressed to find novel PR inhibitors.

We have shown that a scaffold bearing a PR recognition site can be efficiently expressed on the surface of mammalian cells, enabling its detection by flow cytometry. We have also expressed a GFP scaffold with an internal PR cleavage site. In alternative embodiments, the scaffolds of the invention are used in high throughput screening for finding novel peptide inhibitors against PR.

Example 2

Exemplary Assays And Multiplexed Systems of The Invention

In alternative embodiments the invention provides compositions, assays and multiplexed systems for screening for protease, e.g., HIV-1 protease (PR) (an aspartyl protease), inhibitors. PR is required for the efficient processing of the Gag and Gag-Pol precursor polyproteins; a critical step in the viral life cycle.

Exemplary Assay overview: In order to establish a reliable and reproducible assay for monitoring the activity of HIV-1 PR, specifically designed to maximize throughput capabilities, it was important to address several issues.

First, we aimed at establishing the assay as a cell-based assay, and in a cell type that would mimic the natural environment of HIV-1 infection, such as T-cells. Secondly, because of the possible toxic side effects of PR the assay needed to be designed in an off/on system for the inducible expression of PR. Finally, in order for the assay to provide significant benefits, it needed to include a straight-forward readout such as eGFP expression. This would allow for the analysis by flow cytometry, with no necessary staining and make the assay easily adaptable to high-throughput screening. An overview of this exemplary assay of the invention is described in FIG. 1.

This exemplary assay relies on the presence or lack of eGFP expression that serves as biosensor for PR activity. The assay is designed so that cells expressing blocked or inactive PR can be easily discriminated from those expressing active PR based on eGFP expression.]

Confirmation of a Reporter/Activator (Gal4/UAS) System in Mammalian Cells:

Before the establishment of a stable cell line expressing all of the elements of the assay, it was crucial to first verify that the elements of the assay respond transiently as expected. Preliminary experiments were performed in adherent HEK 293T cells. First, we tested a reporter vector containing a 5×UAS Gal4 responsive element upstream of a minimal CMV promoter followed by the eGFP reporter gene. When 293T cells were transfected with this vector alone, there was little to no background. This lack of background expression from the reporter gene was vital to the success of developing a reliable assay. To investigate the level of Gal4-dependent eGFP expression, we first co-transfected the reporter vector with pcDNA3.1-Gal4, a construct based on the pcDNA3.1 vector for mammalian expression (see Figures). The Gal4 gene utilized here encodes only for the DBD and TAD segment of Gal4. While other variants of Gal4 (such as Gal4VP16) are capable of significantly higher induction of genes under UAS control, minimal Gal4 allows for simple insertion of a proteolytic enzyme within the two distinct domains whose behavior has been well characterized. As expected, co-transfection of the reporter vector with pcDNA-Gal4 led to a dramatic induction of eGFP expression in 293T cells (see Figures).

Insertion of the HIV-1 PR Sequence Between the Gal4 Domains does not Substantially Disrupt Gal4 Activity in Mammalian Cells:

Next, we corroborated that the insertion of a PR sequence within the Gal4 DBD and TAD domains maintains Gal4's ability to serve as a functional transcription factor. To test this, we first introduced a mutated version of PR reported to be inactive. This fusion was designed to ensure that the insertion 'per se' of the specific PR sequence does not jeopardize the ability of Gal4 to act as a transcription factor. For this purpose, the HXB2 HIV-1 sequence of the PR mutant version D25A including the 22 upstream amino-acids and the 32 downstream amino-acids of PR (to include the PR cleavage sites) was introduced in between the Gal4 DBD and TAD within a pcDNA3.1 vector (Figure). PR D25A has previously been shown to lack catalytic activity, and, as such, should not be able to separate the domains, nor disrupt the ability of DBD and TAD to work in conjunction and activate the reporter eGFP expression. As expected, reporter and pcDNA-PRmiGal4 co-transfection resulted in significant eGFP expression (see Figures). Although the induction of eGFP expression by the PRm/Gal4 fusion was less than that of Gal4 alone, the level of activation was sufficient for a clear and reliable readout.

Wildtype PR Fused Between the Gal4 DBD and TAD Results in a Transcription Factor with Abolished Activity:

We next substituted the PRm sequence with the wild-type sequence. This sequence contained the exact same additional 22-upstream and 32-downstream amino-acids from PR, but retained the wild-type aspartic acid residue at position 25. Co-transfection of the reporter vector with wild-type PR between the Gal4 domains led to a significant reduction in reporter eGFP expression compared to the mutant fusion or Gal4 alone.

Wildtype PR Fused within the Gal4 DBD and TAD has Restored Transcriptional activation in the Presence of a PR Inhibitor.

It was of critical importance to verify the ability for the PR/Gal4 fusion to activate the reporter eGFP by the addition of PR inhibitors. For that purpose, 293T cells were pre-treated with 10 µM Indinavir and then co-transfected with reporter and pcDNA-PR/Gal4 vectors. While control cells or cells incubated with 10 µM DMSO lacked eGFP expression, cells incubated with 10 uM Indinavir showed a drastic induction in HEK293T cells. As expected, the activity of PR/Gal4 was restored in the presence of inhibitor, as seen by the UAS-dependent transcription of the inhibited fusion protein (see Figures).

Design of Lentiviral Constructs and Infection of T-Cells with the Assay Elements.

We next addressed the question whether these results could be reproduced in T-cells, a cell-type that represents a more natural milieu for HIV-1 infection. For that purpose, we have utilized retroviral technology to stably express the elements of the assay in mammalian cells. Reporter element and Gal4 or PR/Gal4 fusions were transferred into lentiviral vectors. First, the reporter sequence was inserted into an HIV-based self-inactivating lentiviral vector with a modified U3 sequence was utilized to ensure that no reporter background activity was observed in the absence of an inhibitor. Secondly, we wished to create inducible expression of PR/Gal4 fusions. This would alleviate our concern for the difficulty in creating a stable cell line expressing PR due to the reported possible cytotoxicity of active PR in mammalian cells.

To obtain an inducible cell line, we utilized the tetracycline inducible system (Tet-On). For this purpose we constructed two lentiviral vectors; one harboring a 7× Tetracycline Response Element (TRE) upstream the gene of interest and another expressing the reverse tet-transactivator (rtTA) coupled to an IRES-mCherry cassette to corroborate rtTA expression. In this system, the TRE element is bound and activated by rtTA only in the presence of an inducer (Tet or Dox). Gal4, PR/Gal4 and PRm/Gal4 were all transferred into the TRE inducible vector (see Figures).

The UAS Reporter and PR(m)/Gal4 Fusions Behave Similarly in SupT1 Cells as HEK293T Cells.

We first confirmed whether the results obtained in the transient experiments in 293T cells with reporter and PR/Gal4 vectors could be reproduced with the lentiviral reporter and inducible Gal4 fusion proteins in T-cells. We have chosen SupT1 cells, a T-cell line easily infected by HIV-1 and broadly utilized in HIV-1 studies. Viral particles were produced as described in Methods. When SupT1 cells were infected with lentiviral particles containing the reporter vector alone, no detectable eGFP expression was observed, and similar results were obtained with virus encoding inducible Gal4 alone (see Figures). Importantly however, when cells were co-infected with virus produced from the reporter (pH-5×UAS-eGFP), rtTA (pBMN-rtTA-i-mCherry) and inducible Gal4 (pH-TRE-PRm/Gal4) encoding vectors, eGFP expression was still undetectable. However, when these cells were treated with 1 µg/mL Dox, eGFP expression was clearly induced. This confirmed the feasibility of engineering a Tet-off/on inducible system in T-cells to control PR expression.

SupT1 cells were transduced with viral particles generated from the reporter, rtTA and inducible PRm/Gal4 (pH-TRE-PRm/Gal4) which resulted in similar induction of eGFP as Gal4 alone, and again only in the presence of Dox (1 ug/ml). Finally, cells were infected with virus encoding the reporter, rtTA and inducible wild-type PR/Gal4 (pH-TRE-PR/Gal4) to test the ability for this system in T-cells to indicate the levels of PR activity. In the presence of 1 µg/mL Dox, eGFP levels were nearly undetectable. However, in the presence of both 1 µg/mL Dox and 10 µM Indinavir, a large induction of eGFP expression was observed. This validated the ability to utilize eGFP expression as a biosensor of an active PI in SupT1 cells.

Generation and Selection of Monoclonal Stable Cell Lines with the Highest Responsiveness in the Assay.

The experiments performed with lentiviral particles were analyzed from non-clonal cell populations and corroborated that the assay functions as expected. Nevertheless, our goal was to design an assay in T-cells that also had a definitive and robust readout. Therefore, it was important to purify and amplify specific clones from this population that possessed the lowest degree of background and highest degree of eGFP expression in response to the appropriate treatment.

Cells harboring rtTA, 5×UAS-eGFP and either Gal4 or PRm/Gal4 were activated with 1 µg/mL of Dox. Cells harboring rtTA, 5×UASeGFP and PR/Gal4 were activated with the same concentration of Dox, however were pre-incubated with 10 µM Indinavir. All cells were then sorted 24 hours later based on eGFP expression to enrich cells with an activatable reporter and an inducible transcription factor. One more round of sorting was performed under identical conditions. Finally, another round of sorting was performed seven days later to isolate cells with no eGFP expression (i.e. cells with little to no background). This resulted in a cell population that was up to 80% positive for eGFP after activation and with nearly zero background.

Finally, individual cells from these sorted populations were sorted into a 96 well plate based on the lack of eGFP expression. Clonal cell lines obtained from this experiment were later activated under the same conditions described above, and screened for the individual clones which responded as desired (minimal background and maximal eGFP activation). A clone for each of the inducible elements (Gal4, PRm/Gal4 and PR/Gal4) was obtained. The selected clones exhibited nearly 100% activation ability with nearly zero background. These clones were then expanded and further tested in the following experiments.

Doxycycline Activation Titration of the Clones:

In order to optimize the assay for maximal Gal4, PR/Gal4 or PRm/Gal4 induction, we analyzed the effect of increasing levels of Dox. Cells with 0, 50, 100, 250, 500, 750, 1,000, and 2,000 ng/mL Dox were either treated with 10 uM DMSO or 10 uM Indinavir and analyzed 32 hours later. TRE-Gal4 cells reached saturation with Doxycycline at about 1,000 ng/mL whether Indinavir was present or not. TRE-PRm/Gal4 was surprisingly induced at lower levels, reaching saturation at around 250 ng/mL in both uninhibited and Indinavir-treated cells. Again, as with transiently transfected 293 cells, TRE-PR/Gal4 cells had little to non-detectable eGFP expression at any given Dox concentration in the absence of 10 µM Indinavir. However, pre-incubation with 10 µM Indinavir showed maximal eGFP induction at around 500 ng/mL Dox (see Figures).

Determination of Optimal Time Point for the Analysis of Inhibitor Effect:

To determine the optimal time point for the analysis of eGFP expression in the presence of inhibitor, cells were activated with Dox and analyzed by flow cytometry 4, 8, 12, 16, 20, 25, 50, or 75 hours later. Six-well plates containing 250K cells per well in 3 mL media were treated either with DMSO alone as control, or 1 µg/mL Dox and 10 µM Indinavir. DMSO-treated cells maintained lack of fluorescence throughout the experiment (Figure). However, Dox-activated cells incubated with Indinavir showed an initial induction of eGFP expression at 8 hours reaching nearly 100% by 50 hours (h).

Assay Response to Various PR Inhibitors:

Finally, in order to address the sensitivity of the assay to other PR inhibitors, we have analyzed the effect of known FDA-approved inhibitors. For that purpose, cells were incubated with DMSO alone, as described above, or with increasing concentrations of Atazanavir, Amprenavir, Darunavir, Indinavir, Nelfinavir, Lopinavir, Ritonavir, Saquinavir and Tipranavir, all PR inhibitors, at a range including the most commonly used concentrations in cell culture, but also including low ranges not typically active in less sensitive assays. The range chosen extended from 1 nM to 20 µM.

Darunavir and Atazanavir had the strongest effect on PR inhibition, resulting in eGFP activation at only 1 nM. Indinavir and Tipranavir showed the lowest levels of reporter activation at low concentrations, although were also observed to induce nearly full activation at 5 µM. Interestingly, most of the tested PR inhibitors led to increasing eGFP expression levels at increasing concentration of inhibitor throughout the curve, up to 20 µM, the maximal level tested, however, Lopinavir and Nelfinavir resulted in significant cell death around 1 uM concentration, with significant decline in the number of eGFP positive cells as was the case for Saquinavir at 20 µM. Overall, every inhibitor tested showed significant inhibitory effect that resulted in the complete activation of eGFP expression in the reporter T-cell clones.

Discussion

This exemplary assay of the invention is designed to allow for the simple screening of novel inhibitory compound or peptide candidates in a simple flow cytometry-based platform. As such, it will allow investigators to perform screening of millions of candidates (through rational or non-rational-based approaches) in a single experiment, enhancing high throughput capacity. The assay described here is intended to greatly facilitate screening for the search of novel PR inhibitors in T-cells, one of the main natural targets of HIV infection. Importantly, we have established an assay whose elements can be easily transferred to other relevant cell types for the establishment of HIV infection and the search for novel PR inhibitors. These include cells such as macrophages or dendritic cells.

The mean fluorescence intensity of eGFP in activated cells steadily increased as inhibited cells continued to accumulate higher levels of eGFP, making those cells with an inhibited PR even more identifiable than those negative for PR inhibition.

In some aspects, analysis of a time point for the effect of an inhibitor may be critical. Thus, choosing a time-point that is average for all is only an estimation for the search of unknown inhibitors.

Methods

Cloning and Vector Construction:

Gal4, PR/Gal4 and PRm/Gal4 sequences were amplified by PCR for the production of the transient expression vectors pcDNA-Gal4, pcDNA-PR/Gal4 and pcDNA-PRm/Gal4 respectively. For that purpose the constructs pMA236, pHP236 and pHP236m (Murray et al., 1993) were used as template together with the Gal4 forward primer with extending HindIII and NotI sites ACGCACGCAAGCTTGCGGC-CGCCCACCATGAAGCTACTGTCTTCTATC (SEQ ID NO:6) and the Gal4 reverse primer with extending SalI site ATAGCTGCGTGCGTGCGTGTCGACT-TACTCTTTTTTTGGGTTTGG (SEQ ID NO:7).

PCR products were then digested with HindIII and SalI and ligated into pcDNA™3.1/Zeo (Invitrogen, Carlsbad Calif.). pFR-eGFP was kindly provided by Rainer de Martin (University of Vienna). In short, pFR-eGFP was created by adapting the pFR-Luc vector (Stratagene, San Diego, Calif.). The firefly luciferase gene was removed and replaced with eGFP.

For the construction of the inducible pH-TRE, pH-TRE-eGFP pH-TRE-Gal4, pH-TRE-PR/Gal4, pH-TRE-PRm/Gal4 vectors, a 7× tet-responsive element (TRE) was amplified from the pTRE-tight (Clontech) with the forward primer with extending NruI site AGCTAGCTAGCTTCGCGA-CACGAGGCCCTTTCGTCTTCA (SEQ ID NO:8) and a reverse primer to complementary to the PolyA signal with an extending BsrGI site CATTTTTTTCACTGCCTCGAGTG-TACAAGCTAGCTAGCT (SEQ ID NO:9).

The PCR product was digested with NruI/BsrGI and cloned into the pH-CMV-eGFP vector, (generously provided by Gary Nolan, Stanford University, CA) to replace the original CMV-eGFP cassette. eGFP was then amplified with a forward primer containing an extending BamHI site, and a reverse primer with an extending NheI site. The eGFP insert was then cut and ligated within the multiple cloning site of pH-TRE. The forward Gal4 primer with an extending BamHI site ATGCATGCGGATCCACCATGAAGCTACT-GTCTTCTATC (SEQ ID NO:10). and the reverse primer with an extending NheI site GCATGCATGCTAGCT-TACTCTTTTTTTGGGTTTGG (SEQ ID NO:11). were used to amplify the Gal4-based cassettes from pcDNA3.1-Gal4, pcDNA3.1-PR/Gal4, and pcDNA3.1-PRm/Gal4 and insert them into pH-TRE digested with BamHI/NheI.

pBMN-i-mCherry was constructed by amplifying mCherry from pmCherry-C1 (Clontech) with the forward primer with extending NcoI site ATCGATGGATCCCCAC-CATGGTGAGCAAGGGCGAGGAG (SEQ ID NO:12). and reverse primer with extending XhoI site: ATGGAC-GAGCTGTACAAGTAACTCGAGGATCGATC (SEQ ID NO:13), and inserting it into partially digested pBMN-i-eGFP (Gary Nolan, Stanford University) with NcoI/SalI. pBMN-i-mCherry-rtTA was then constructed by removing rtTA from the vector Tet-On® (Clontech) with EcoRI/BamHI and cloning it into pBluescript-SK (Invitrogen, Carlsbad Calif.). It was then removed with EcoRI/XhoI and ligated into pBMN-i-mCherry.

pH-5×UAS-eGFP was constructed by digesting pFR-eGFP with MfeI/BsrGI and ligating the 5×UAS-eGFP insert into pH-CMV-eGFP digested with MfeI/BsrGI to replace the CMV-eGFP cassette.

Transfections:

293T cells were transfected as follows. 15 µl of 2 mg/mL Polyethylenimine linear 25 kD (Polysciences, Inc.) were added to 125 µl of DMEM in a 1.8 ml Eppendorf tube. 3 µg of each DNA was added drop-wise to each tube. Tubes were mixed and incubated for 20 min at RT. This mixture was then added drop-wise to 293T cells in a 10 cm plate at ~60-75% confluence. Cells were then analyzed by fluorescence microscopy and/or flow cytometry 24 hrs post transfection.

Production of Viral Particles for Retroviral Transduction:

For the production of MLV based virus (pBMN-i-mCherry-rtTA virus), Phoenix GP cells (Nolan Lab, Stanford University, CA) at 50-60% confluence were transfected with 3 ug of the packaging vector (pBMN-i-mCherry-rtTA) and 3 µg of pCI-VSVg envelope vector. Media was changed after 24 hours leaving 6 mL of media (DMEM with 10% FCS, Pen-Strep, L-Glutamine) in a 10 cm plate. At 48 hours, viral supernatant was collected, filtered with 0.45 micron PTFE filters (Pall Corporation) and frozen at −80° C. in 1 mL aliquots and frozen at −80° C.

For the production of HIV based virus (pH vectors), 293T cells at 50-60% confluency were transfected with 3 µg packaging vector (pH vectors), 2 ug pCI-VSVg, VPR encoding vector, and 3 µg pCMVΔ8.2 (Didier Trono, EPFL, Switzerland). Media was changed at 24 hours leaving 6 mL fresh media (DMEM with 10% FCS, Pen-Strep, L-glutamine) Supernatant was collected at 48 hrs, filtered and collected as described above.

Infections:

A 2 ml reaction containing 4 µl of 5 µg/mL Polybrene (Hexadimethrene Bromide, Sigma), 500K SupT1 cells in RPMI (10% FCS, L-glutamine, Pen-strep) and 250 µl frozen viral stocks was mixed, added to wells in 6-well plates, and spun in a hanging bucket rotors Becton Dickinson centrifuge at 1500 RPM, for 120' at 32° C. Cells were re-suspended and placed in a 37° C. incubator for the analysis of expression at least 72 hours post-infection.

Fluorescence Microscopy for Analysis of Expression:

Cells were analyzed by fluorescence microscopy on a Zeiss Observer D1 microscope with a 50× lens and 40HMC filter connected to an AxioCam MRm camera, and analyzed on Axio-Vision software. The length of exposure for fluorescent channels was based on the exposure for the Gal4 only controls. This length was then kept constant for the exposures of all of the other samples.

Flow Cytometry and Sorting:

Flow Cytometry was performed on a BD FACSAria with 488 nm and 633 nm lasers. Data was collected on FACSDiva 6.1.1 software and then exported to FlowJo. eGFP expression was detected in the FITC channel and mCherry expression was detected on the PE-Texas-Red channel. Cells were first gated for size and granularity (FSC-A vs SSC-A) followed by doublet gating (FSC-A vs FSC-W and SSC-A vs. SSC-W). Sorted populations were gated on PE-TexasRed vs FITC plot. 250K cells were collected for each sample into 0.5 mL fetal calf serum (FCS) and 1 mL RPMI. Cells were then spun down at 1500 RPM and resuspended in fresh media in 6-well plates. Cells were allowed to grow for at least seven days to allow for expansion and loss of previously activated eGFP expression.

Figure Legends Example 2

FIG. 19 illustrates an overview of the assay: FIG. 19A. Wild type Gal4 as control, no Dox. Without the presence of Dox, rtTA can not bind to the tet-responsive element (TRE) and as a result, there is no induction of Gal4 expression. Consequently, there is no eGFP expressed from the reporter construct. FIG. 19B. In the presence of Dox, Gal4 expression is induced. Gal4 then binds to the 5×UAS of the reporter gene and activates eGFP expression. FIG. 19C. The same system with the PR/Gal4 fusion. In the presence of Dox PR/Gal4 is expressed; however, its catalytic activity results in the separation of the Gal4 domains, and thus there is no yield of eGFP. FIG. 19D. The same scenario as in C but in the presence of a PR inhibitor. PR/Gal4 fusion with Gal4 is retained, resulting in the induction of eGFP expression. Same results are expected if PR is mutated, with no additional need of PR inhibitors.

FIG. 20 illustrates a transient expression of the assay components in HEK293T cells. FIG. 20A schematically illustrates exemplary constructs used for transient expression of the assay elements. FIG. 20B. Top Panel: Fluorescence microscopy of eGFP expression in HEK293T cells 24 hours post transfection with the reporter vector (pFR), or co-transfection with the reporter vector plus either the Gal4, PR/Gal4, or PRm/Gal4 vectors. Bottom panel: HEK293T cells were analyzed by flow cytometry at 24 hours post transfection with the same conditions top panel. Gates were drawn to determine the ability to identify cells with an active PI. FIG. 20C. Quantification of eGFP expression in HEK293T transfected with various assay elements. The numbers of cells under various conditions were quantified for eGFP levels indicative of PR inhibition. Results shown are an average of 3 experiments.

FIG. 21 illustrates generation of a monoclonal T-cell line stably expressing inducible assay elements. FIG. 21A (upper left) schematically illustrates exemplary constructs utilized to generate infectious particles for the transduction of SupT1 cells with the various assay elements. FIG. 21B (right) illustrates data from a cell sorting assay comprising: a previously generated stable SupT1 cell line expressing rtTA and mCherry was infected with the reporter virus (generated from pH-5×UAS-eGFP), or co-infected with the reporter virus plus a virus encoding an inducible assay element (generated from pH-TRE-Gal4, pH-TRE-PR/Gal4, or pH-TRE-PRm/Gal4). Cells were then activated with either 1 µg/mL of Dox alone, or were pre-incubated for 5 minutes with 10 µM Indinavir following activation with 1 µg/mL Dox. Initial infections with low yields (left column) were then subjected to several rounds of sorting on a BD FACSAria to obtain a cell population with a higher assay response (middle column). Finally, single SupT1 cells from the purified population were sorted into 96 well plates and grown as a monoclonal population and then tested for optimal responses to assay induction of eGFP under appropriate conditions. FIG. 21C (lower left) illustrates images of fluorescence microscopy of SupT1 clones expressing the assay elements. Cells expressing various elements of the assay were treated as indicated with DMSO, DMSO+1 µg/mL Dox, or 1 µl/mL Dox+10 µM Indinavir and analyzed 24 hours later by fluorescence microscopy for mCherry and eGFP expression. D. Quantification of eGFP expression of clonal SupT1 cells treated with DMSO, DMSO+1 µg/mL Dox, or 1 µg/mL Dox+10 µM Indinavir.

FIG. 22 graphically illustrates data determining the optimal conditions for activating the assay to screen for PR inhibition. FIG. 22A graphically illustrates a Doxycycline titration. Clonal SupT1 cells harboring an inducible Gal4, PR/Gal4 or PRm/Gal4 were pre-incubated in a 96 well plate with either DMSO or 10 µM Indinavir and then either left untreated, or activated with 50, 100, 200, 500, 1000, or 20000 ng/mL of Dox. Cells were analyzed by flow cytometry and gated to determine the number of cells positive for eGFP expression. FIG. 22B graphically illustrates a time course of eGFP Induction in response to Doxycyline activation in the presence of DMSO or a PI. SupT1 clones harboring Gal4, PR/Gal4, or PRm/Gal4 were pre-incubated in a 96 well plate with either DMSO or 10 µM Indinavir and then activated with 1 µg/mL Dox. Cells were analyzed at either 4, 8, 12, 16, 20, 25, 50 or 75 hours by flow cytometry and gated for eGFP positive expression.

Figure 23:
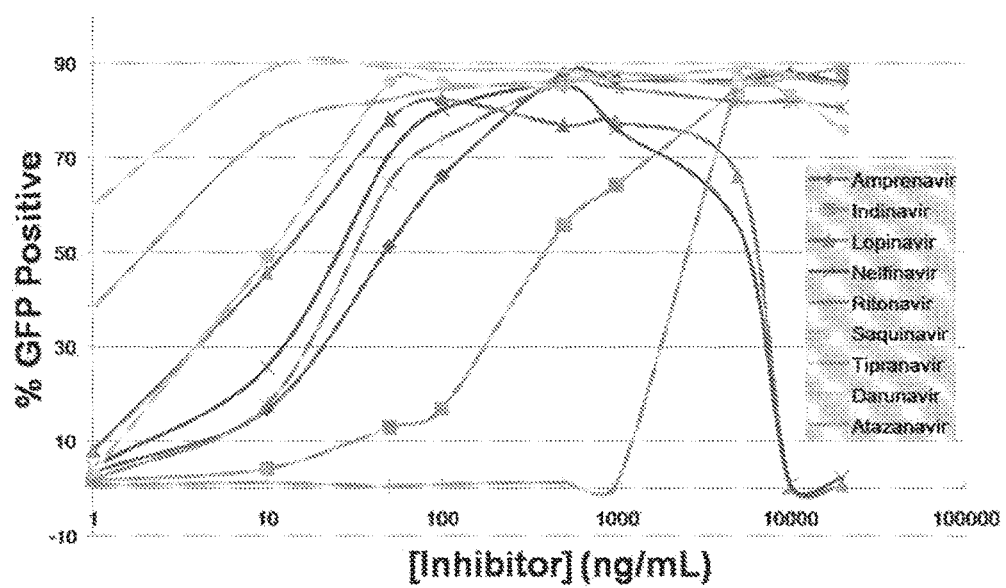
FIG. 23 graphically illustrates data from an assay response to existing PI's; as discussed in detail in Example 2, below.

FIG. 23 graphically illustrates data from an assay response to existing PI's. The selected SupT1 clone expressing rtTA and the 5×UAS-eGFP reporter and an inducible PR/Gal4 were activated with 1 µg/mL and incubated with various concentrations (1, 10, 50, 100, 500, 1000, 5000, 10000 or 20000 ng/mL) of an FDA approved PI: Either Amprenavir, Atazanavir, Darunavir, Indinavir, Lopinavir, Nelfinavir, Ritonavir, Saquinavir, or Tipranavir. Cells were then analyzed 50 hrs later for eGFP expression as determined by flow cytometry on a BD FACSAria.

Example 3

Exemplary Assays and Multiplexed Systems—Conditional Protease/Gal4 Fusion-Based Systems In alternative embodiments, the invention provides compositions and assays to screen for both protease inhibitors, including viral protease inhibitors such as PR, that can be used e.g., as anti-viral or anti-retroviral therapy against e.g., HIV-1, or AIDS, which remains a devastating disease. The invention provides assays for identifying novel drugs and targets in the fight against HIV and other diseases. The invention provides assays for identifying novel drugs not having the side-effects of existing drugs. The invention provides assays for identifying novel drugs effective against strains resistant to known drugs, e.g., because of the high rate of HIV mutation.

In alternative embodiments, the invention provides protease assays, e.g., HIV Protease (PR) assays, for the detection of novel protease inhibitors (PI's), e.g., HIV protease inhibitors, in vivo, or in a cell such as a mammalian cell, a T cell, a bacteria or a yeast, or in vitro. In alternative embodiments, the invention's assays screen for PI's within T-cells, thus allowing a search for inhibitory compounds within a realistic cellular environment and producing more reliable hits. Additionally, in this embodiment the screening can concurrently reveal the toxicity level of drug candidates on T-cells, ruling out lethal hits.

We have engineered a clonal T-cell line with a Doxycycline inducible PR-Gal4 fusion and a Green Fluorescent Protein (GFP), or eGFP, reporter of its activity. Thus, in this exemplary assay of the invention, eGFP acts as a biosensor of PR activity, making it ideal for flow cytometry-based screening. Clones with the highest sensitivity, and robust, reliable and reproducible reporter activity were tested for their ability to detect the presence of a potent PI. The selected clones exhibit eGFP expression in nearly 100% of the population with the addition of every FDA-approved inhibitor tested, with sensitivities ranging down to nanomolar concentrations. This exemplary assay/platform of the invention is a High Throughput Screening assay for PIs that can be performed in T-cells and other mammalian cells, and can facilitate the search for novel peptide- and chemical-compound-based PIs.

Figure 24:
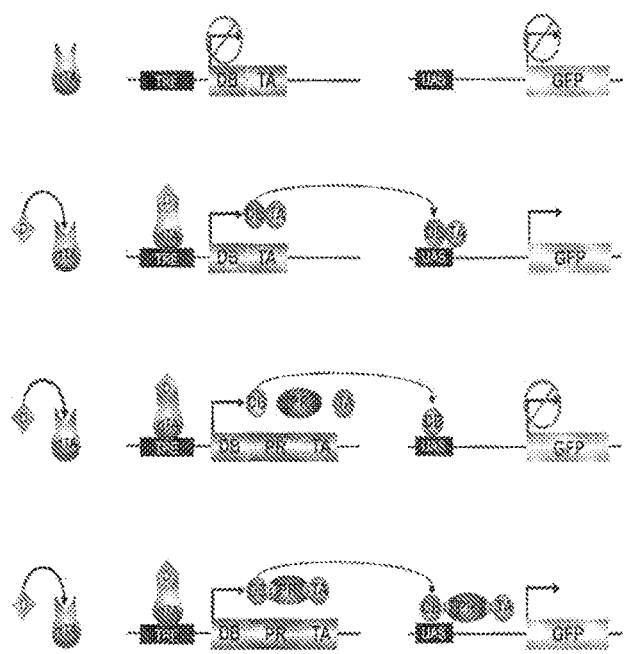
FIG. 24 schematically illustrates an exemplary assay of the invention, a conditional Protease/Gal4 fusion-based system, where GFP is activated only in the presence of a Protease Inhibitor.

FIG. 24 schematically illustrates an exemplary assay of the invention, a conditional Protease/Gal4 fusion-based system, where GFP is activated only in the presence of a Protease Inhibitor:

FIG. 24 A schematically illustrates: No doxycycline, Gal4 (DB and TA domains) cannot be expressed.

FIG. 24 B schematically illustrates: In the presence of doxycycline: D, rtTA binds to the tet-responsive element (TRE) and induces Gal4 expression resulting in the activation of GFP expression.

FIG. 24 C schematically illustrates: Protease/Gal4 is expressed; however, its catalytic activity results in the separation of the Gal4 domains, resulting in the lack of GFP expression.

FIG. 24 D schematically illustrates: In the presence of a protease inhibitor (PI), the PR/Gal4 fusion remains intact, resulting in the induction of GFP expression. The same result is expected with an inactive mutant PR.

Figure 25:
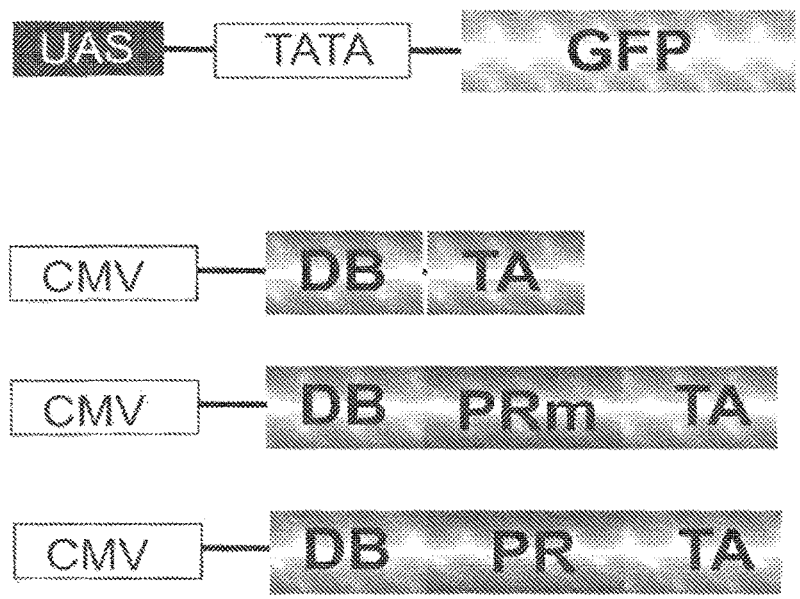
FIG. 25 schematically illustrates exemplary plasmids of the invention; as discussed in detail in Example 3, below.

Transient Assay in Mammalian Cells:

FIG. 25 schematically illustrates exemplary plasmids of the invention for transfection in HEK293T cells; PRm=inactive mutant (D25A). the plasmids are named, from top to bottom of the figure: "pFR-GFP"; "pGal4"; "pPRm/Gal4"; and "pPR/Gal4".

Figure 26:
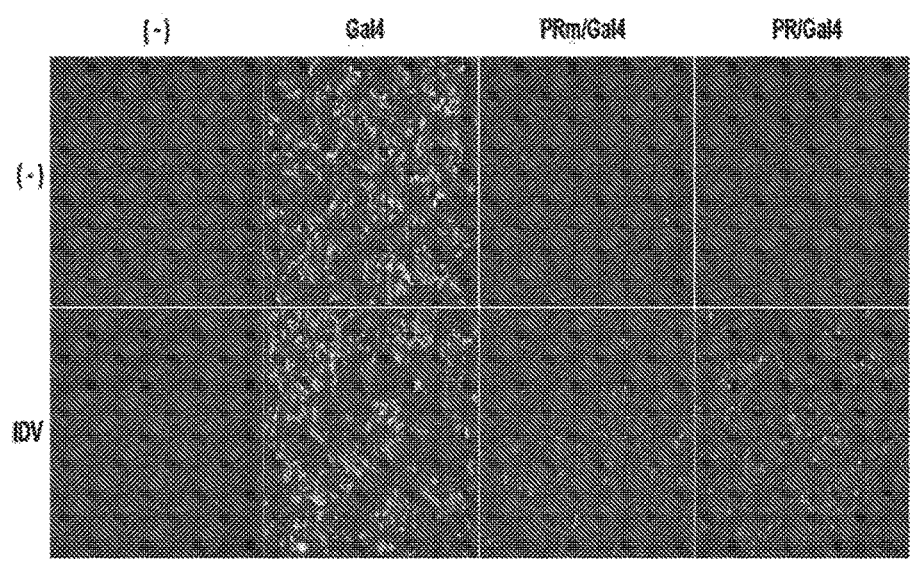
FIG. 26 illustrates data from a fluorescent cell sorting assay, a FACS, showing that GFP is expressed only with the addition of an active PI; as discussed in detail in Example 3, below.

FIG. 26 illustrates data from a fluorescent cell sorting assay, a FACS, showing that GFP is expressed only with the addition of an active PI.

Figure 27:
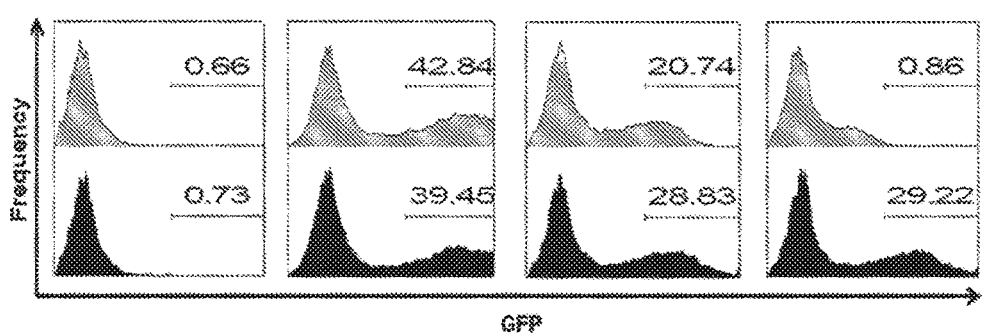
FIG. 27 graphically summarizes the data analysis for 24 h post transfection.

FIG. 27 graphically summarizes the data analysis for 24 h post transfection: FIG. 27A. Fluorescence microscopy; FIG. 27B. Flow cytometry; FIG. 27C Quantification of Flow data; PI=10 µM Indinavir.

Figure 28:
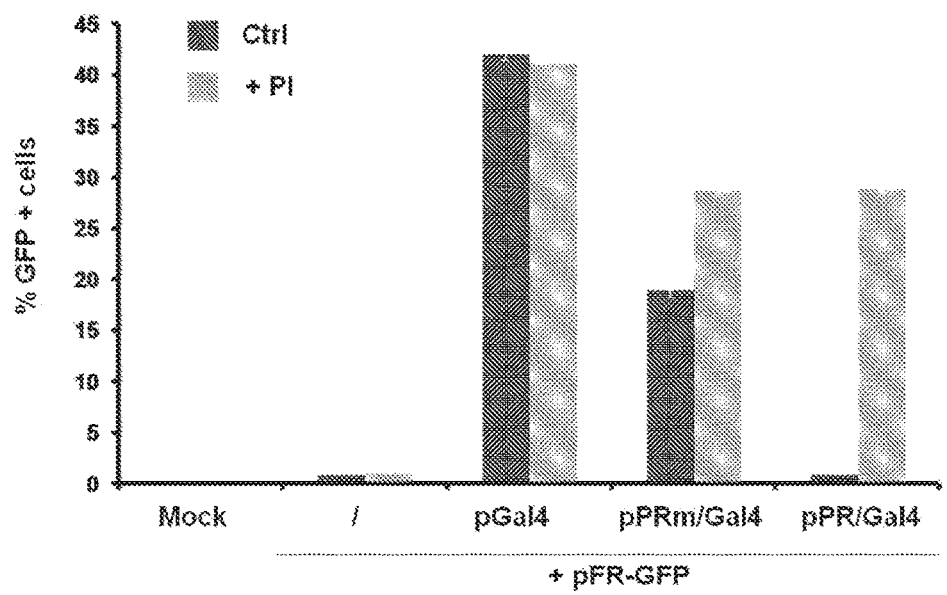
FIG. 28 illustrates data: the y axis is: % GFP+ cells; the x axis is +FRGFP; for each of the paired columns the left column is control and the right column is with inhibitor; the first lane (no columns) is mock run; the second column pair is negative control; the third column pair is "pGal4"; the fourth column pair is "pPRm/Gal4"; and the fifth column pair is "pPR/Gal4"; as discussed in detail in Example 3, below.

FIG. 28 illustrates data: the y axis is: % GFP+ cells; the x axis is +FRGFP; for each of the paired columns the left column is control and the right column is with inhibitor; the first lane (no columns) is mock run; the second column pair is negative control; the third column pair is "pGal4"; the fourth column pair is "pPRm/Gal4"; and the fifth column pair is "pPR/Gal4".

Figure 29:
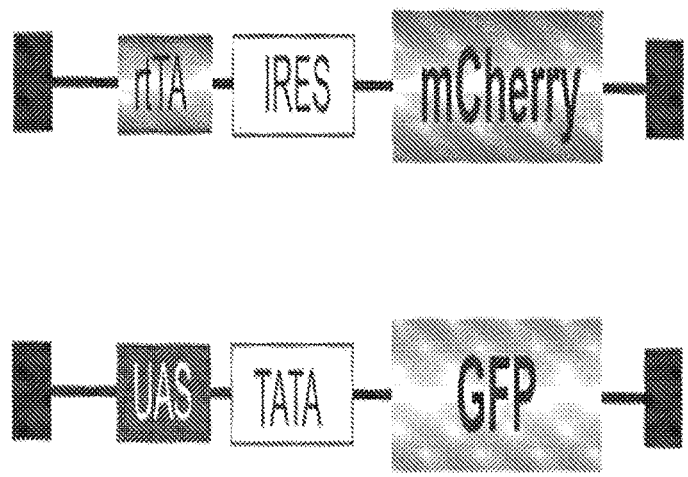
FIG. 29 illustrates constructs used for the generation of retroviral particles; as discussed in detail in Example 3, below.

Stable T cell clones:

FIG. 29 illustrates constructs used for the generation of retroviral particles.

Figure 30:
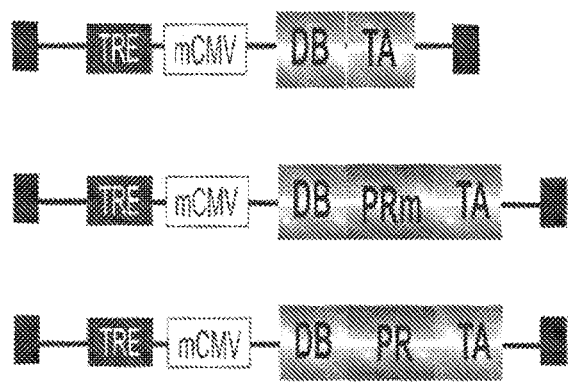
FIG. 30 illustrates plasmids for production of retroviral infectious particles; as discussed in detail in Example 3, below.

FIG. 30 illustrates plasmids for production of retroviral infectious particles.

Figure 31:
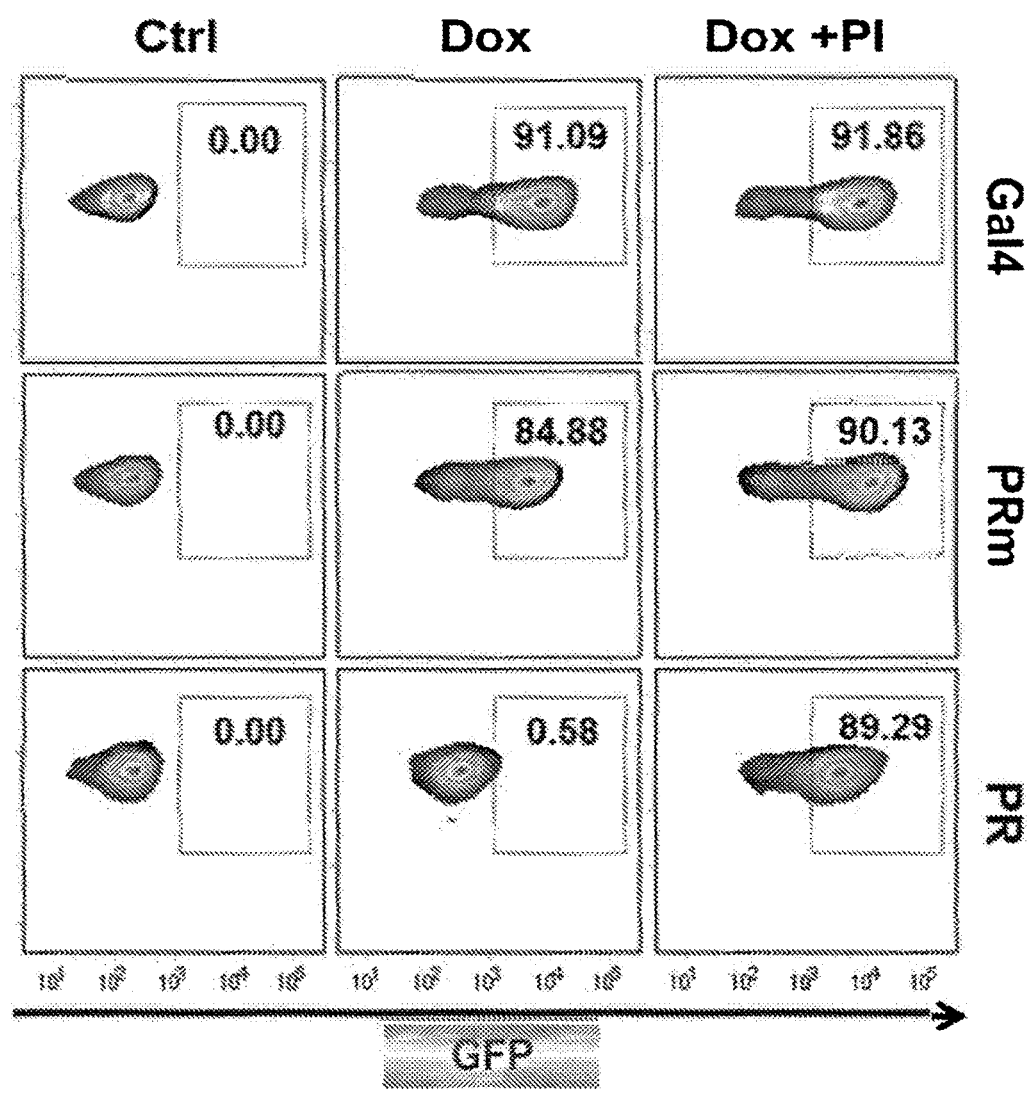
FIG. 31 illustrates data from a cell sorting assay where clones were screened for the highest responsiveness to Dox and PI; where the Gal 4 row shows that Tet inducible activation is very tight; the pPRm row shows that the mutant is inactive; the PR row shows that PR/Gal4 clones exhibit ~90% activation with <1% background. Dox=1 µg/mL Doxycycline; PI=10 µM Indinavir; as discussed in detail in Example 3, below.

FIG. 31 illustrates data from a cell sorting assay where clones were screened for the highest responsiveness to Dox and PI; where the Gal 4 row shows that Tet inducible activation is very tight; the pPRm row shows that the mutant is inactive; the PR row shows that PR/Gal4 clones exhibit=90% activation with <1% background. Dox=1 µg/mL Doxycycline; PI=1004 Indinavir.

Figure 32:
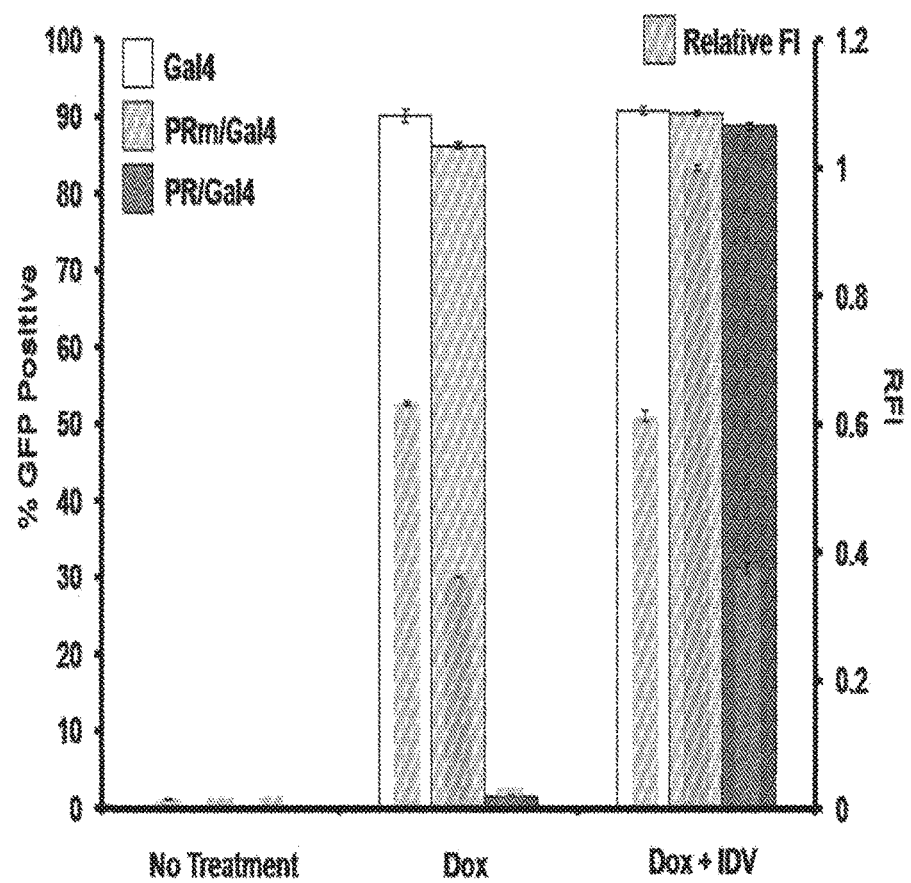
FIG. 32 graphically illustrates GFP expression in selected clones, where the data demonstrates that stable T-cell clones robustly report PR Inhibition; as discussed in detail in Example 3, below.

FIG. 32 graphically illustrates GFP expression in selected clones, where the data demonstrates that stable T-cell clones robustly report PR Inhibition.

Figure 33:
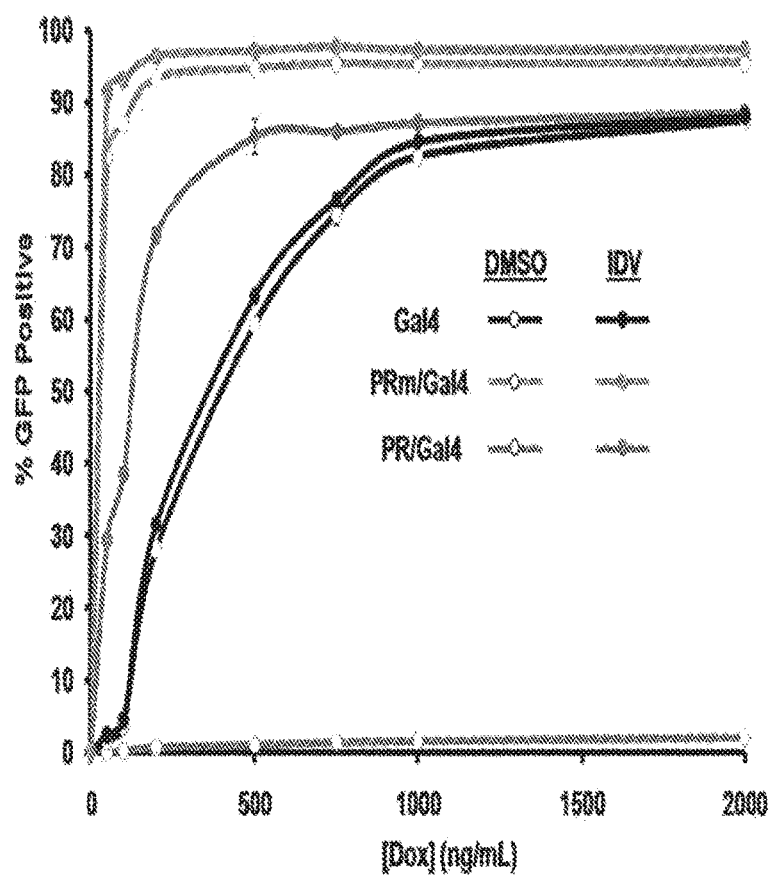
FIG. 33 graphically illustrates Doxycycline Titration—pre-incubation of clonal SupT1 cells with DMSO or 10 µM PI (Indinavir), where the data demonstrates that activation is saturated around 1 µg/mL; as discussed in detail in Example 3, below.

Optimization of PI Screening Conditions:

FIG. 33 graphically illustrates Doxycycline Titration—pre-incubation of clonal SupT1 cells with DMSO or 10 µM PI (Indinavir), where the data demonstrates that activation is saturated around 1 µg/mL.

Figure 34:
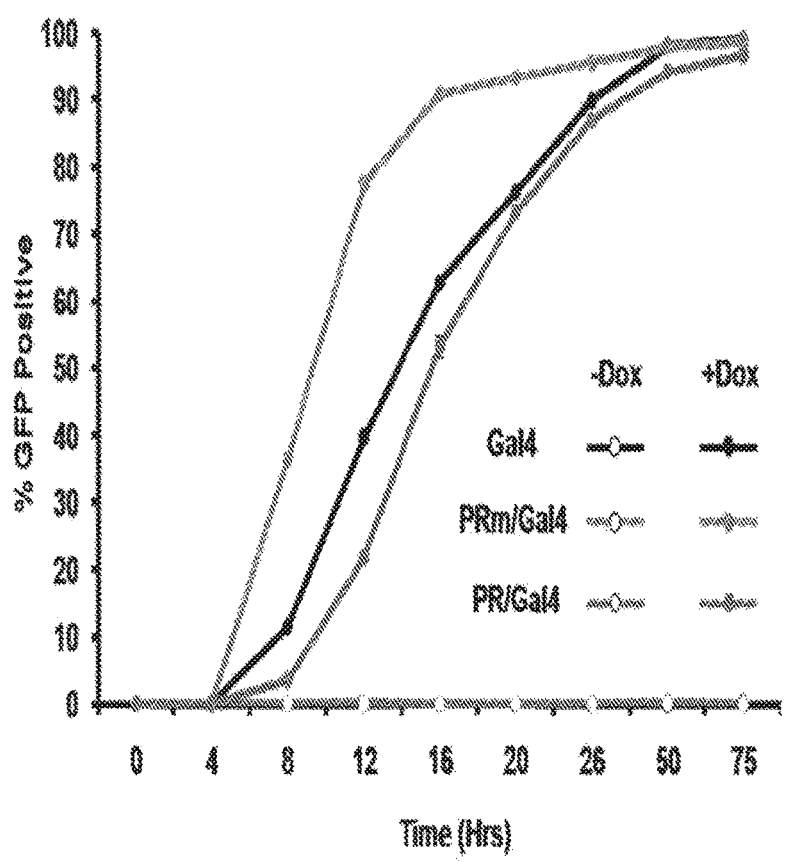
FIG. 34 graphically illustrates the Time Kinetics of the assay in 96-well plates: Pre-incubation of clonal SupT1 cells with 10 µM PI (Indinavir)—control is no Dox with test=Activation at 1 mg/mL Dox, where the data demonstrates that activation of clones reaches max around 48 hrs; as discussed in detail in Example 3, below.

FIG. 34 graphically illustrates the Time Kinetics of the assay in 96-well plates: Pre-incubation of clonal SupT1 cells with 10 µM PI (Indinavir)—control is no Dox with test=Activation at 1 mg/mL Dox, where the data demonstrates that activation of clones reaches max around 48 hrs.

Figure 35:
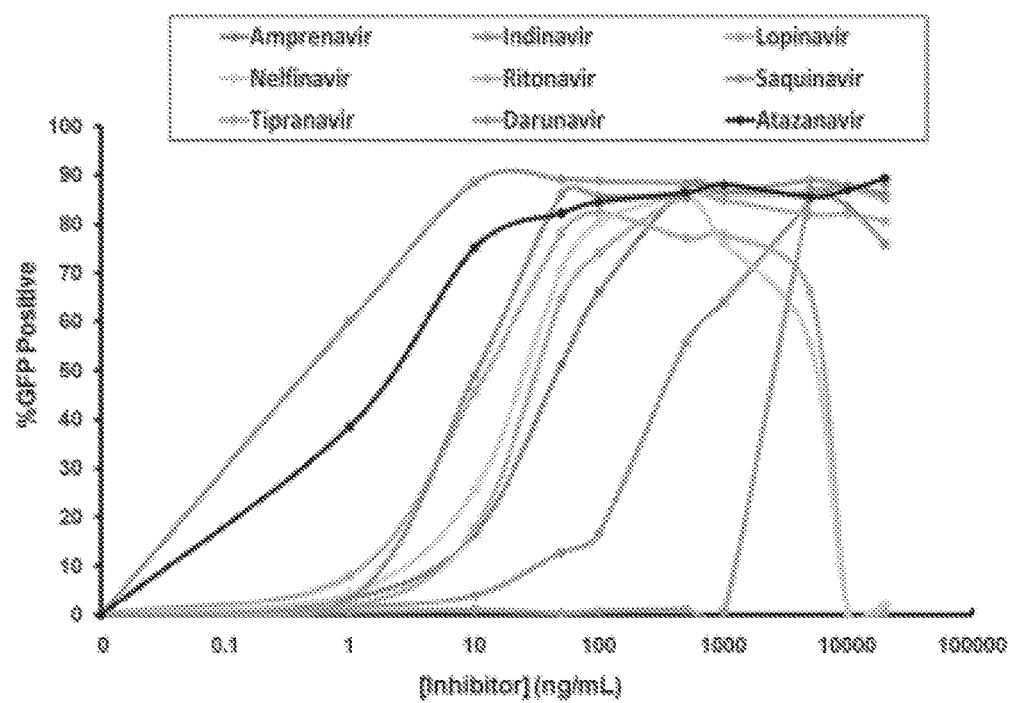
FIG. 35 graphically illustrates data from incubating clonal T-cell lines with various concentrations of PI's; as discussed in detail in Example 3, below.

Assay Response to FDA-Approved PIs:

FIG. 35 graphically illustrates data from incubating clonal T-cell lines with various concentrations of PI's: activation with 1 µg/mL Dox; analyzed 50 hrs later by flow cytometry, where the data demonstrates that at the nanomolar range, the clonal T-cell line shows PR inhibition of every FDA-approved PI.

Example 4

Cell-Based Assays for the Identification of Compositions that Inhibit Envelop Processing In alternative embodiments, the assay screens ER/Golgi-localized random peptide libraries for anti-virals and/or inhibitors of furins or similar assays.

Figure 36:
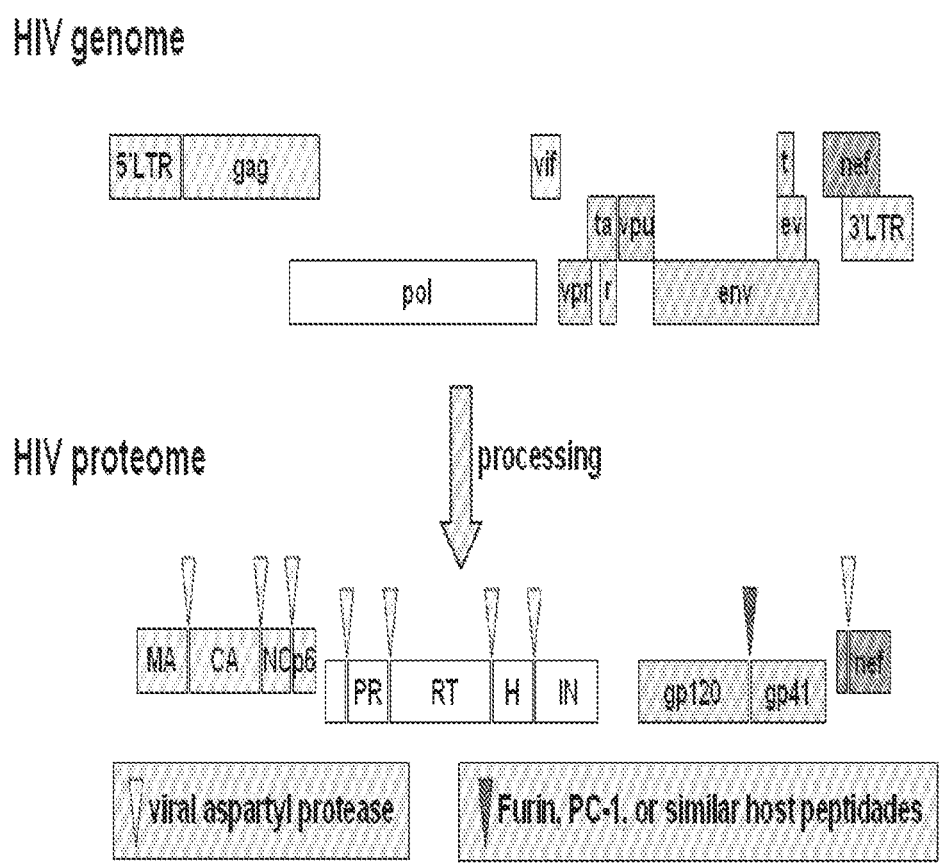
FIG. 36 schematically illustrates the HIV-1 genome and proteome, and the role of furin, PC-1 and similar host peptidases—the enzymes targeted for inhibition by assays of this invention; as discussed in detail in Example 4, below.

FIG. 36 schematically illustrates the HIV-1 genome and proteome, and the role of furin, PC-1 and similar host peptidases—the enzymes targeted for inhibition by assays of this invention. Post translational processing of the viral proteome includes cleavage by both viral and host cell proteases; and assays of the invention can identify inhibitors of both viral and host cell proteases. Viral proteins are processed by the HIV-1 protease with the exception of gp120/gp41.

Figure 37:
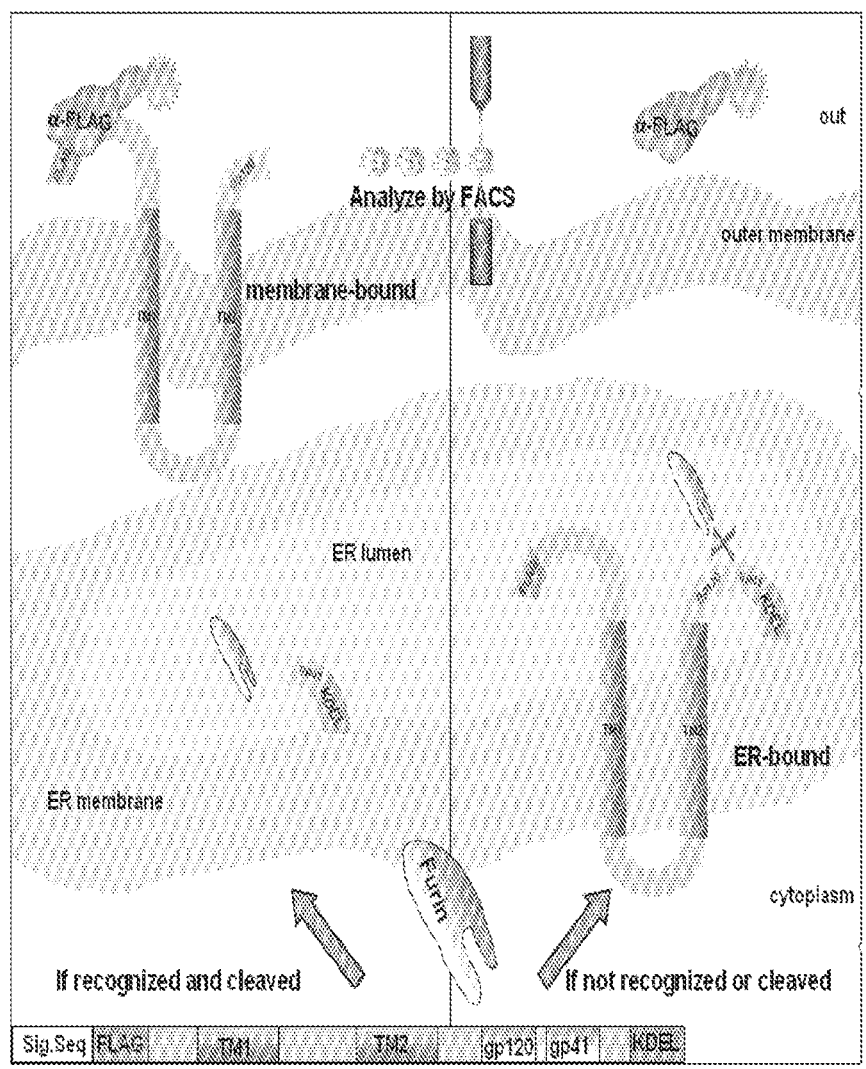
FIG. 37 schematically illustrates an exemplary assay of the invention; as discussed in detail in Example 4, below.

FIG. 37 schematically illustrates an exemplary assay of the invention. FIG. 37 Right panel: when furin, or similar proteinases are blocked or inhibited, the scaffold protein is not cleaved and thus is retained in the ER. FIG. 37 Left panel: If cleaved, the scaffold travels to the cell surface leaving the KDEL sequence behind. This can recognized by flow cytometry, e.g., a FACS, or by using a high throughput screen, or using microscope visualization, which can be automated. The cleaved scaffold will travel from the ER through the trans-Golgi network and to the cell surface, allowing recognition by flow cytometry. Right panel: The scaffold will be retained in the ER through KDEL when cellular peptidases such as Furin are blocked or inhibited, e.g., by peptides or small molecules identified using assays of this invention.

FIG. 38 schematically illustrates constructs for assays of the invention: two retroviral vectors are illustrated: Top: Scaffold construct: the ER-signal sequence followed by the FLAG tag for detection by flow cytometry are fused to two transmembrane domains (TMs) from the CCR5 receptor. Following the TMs, the scaffold contains the gp120/41 boundary that includes the cleavage site. The sequence KRRVVQREKRAVGIGAL (SEQ ID NO:18) (which are residues two (2) to eighteen (18) of SEQ ID NO:17, or AKRRVVQREKRAVGIGALF) is taken from the HXB2 HIV-1 strain. Importantly, the KDEL (SEQ ID NO:1) ER-retention sequence, at the C-terminus of the construct, will allow localization in the ER lumen through KDEL receptors. Bottom: the back-bone of the peptide library is fused to the KDEL sequence and linker to allow flexibility within the ER lumen. In one embodiment, while the scaffold can be detected by fluorescence (mCherry), the library can be selected with blasticidin.

Figure 39:
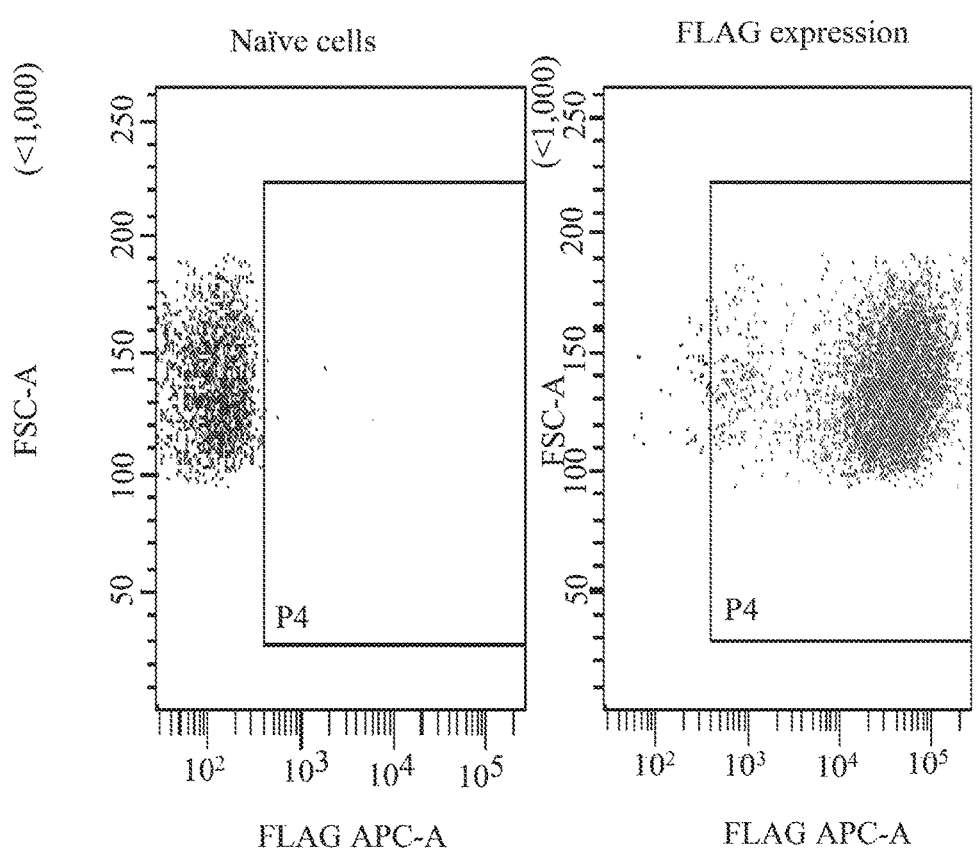
FIG. 39 graphically illustrates flow cytometry data from a FLAG detection assay of the invention; as discussed in detail in Example 4, below.

FIG. 39 graphically illustrates flow cytometry data from a FLAG detection assay of the invention: SupT1 cells were stained with anti-FLAG antibodies and detected by flow cytometry. Left: Control naïve cells. Right: Cells expressing FLAG-tagged CCR5.

Figure 40:
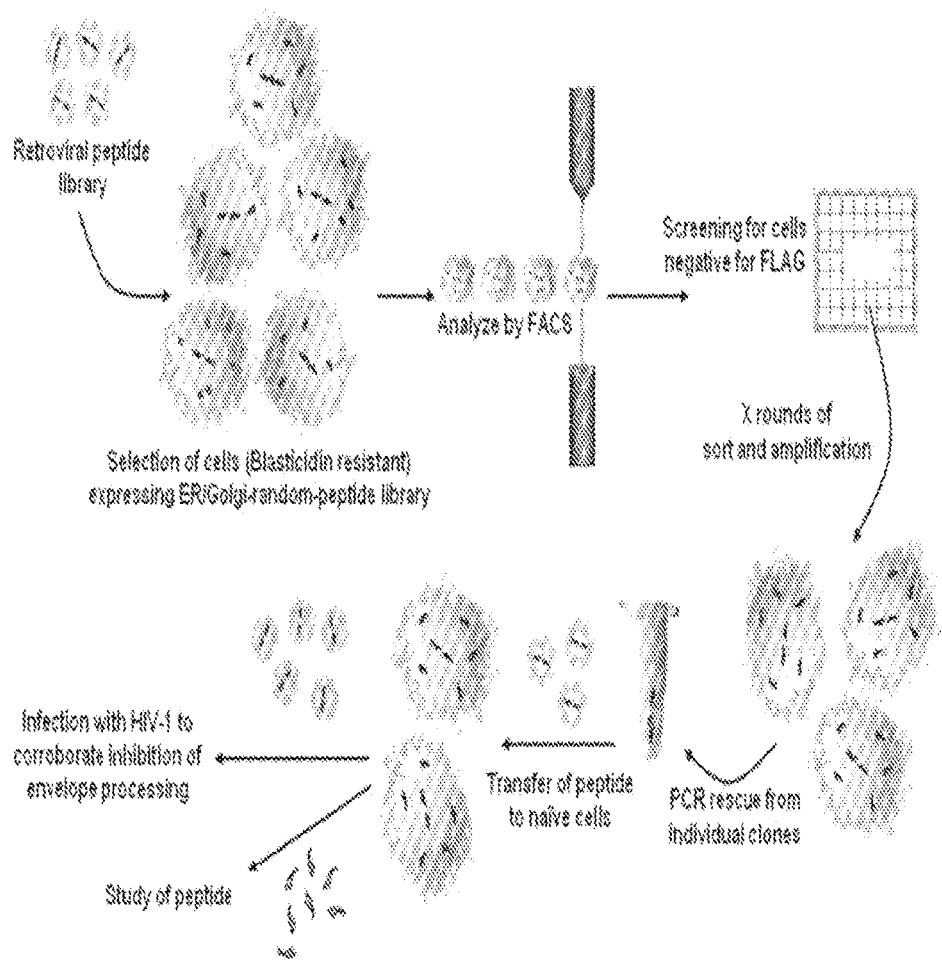
FIG. 40 schematically illustrates an exemplary screening process for an assay of the invention; as discussed in detail in Example 4, below.

FIG. 40 schematically illustrates an exemplary screening process for an assay of the invention: In this embodiment, SupT1 cells expressing the scaffold (mCherry positive) are transduced with the retroviral random peptide library localized to the ER-trans-Golgi apparatus. Cells expressing peptides (blasticidin resistant) are selected. In one embodiment, cells are analyzed by flow cytometry to detect the loss of FLAG cell-surface expression. In one embodiment, these cells are sorted and amplified. In one embodiment, the peptide sequence are rescued by genomic PCR and analyzed for its effects on envelope processing.

Figure 41:
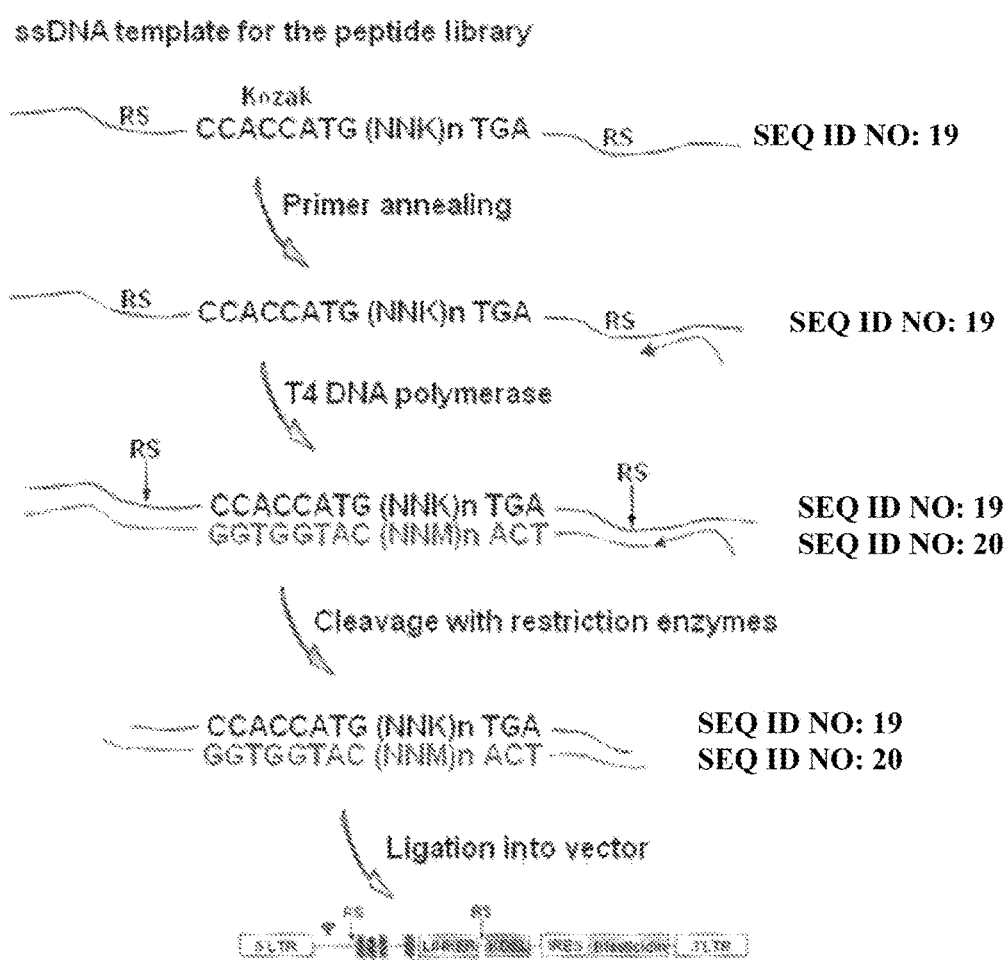
FIG. 41 schematically illustrates construction of a random peptide library used in an alternative embodiment of the invention; as discussed in detail in Example 4, below and identifies SEQ ID NO: 19 and SEQ ID NO: 20.

FIG. 41 schematically illustrates construction of a random peptide library used in an alternative embodiment of the invention. In one embodiment, preparation of random peptide library insert utilizes an NNK motif to minimize stop codons and preserve complexity of the peptide library. CCACCATG(NNK)nTGA is (SEQ ID NO:19); and in one embodiment, these sequences contain a Kozak sequence (or Kozak consensus sequence, Kozak consensus or Kozak sequence, is a sequence which occurs on eukaryotic mRNA and plays a major role in the initiation of the translation process).

Figure 42A:
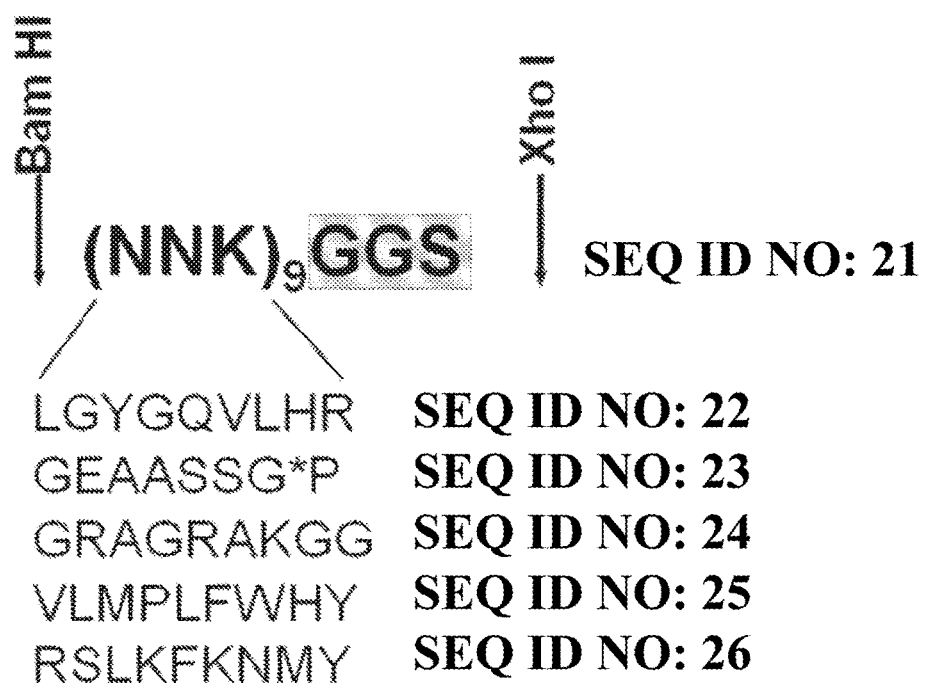
FIG. 42A illustrates exemplary library inserts to corroborate quality, clones were sequenced to confirm their randomness and identifies SEQ ID NO: 21 through SEQ ID NO: 26.
Figure 42B:
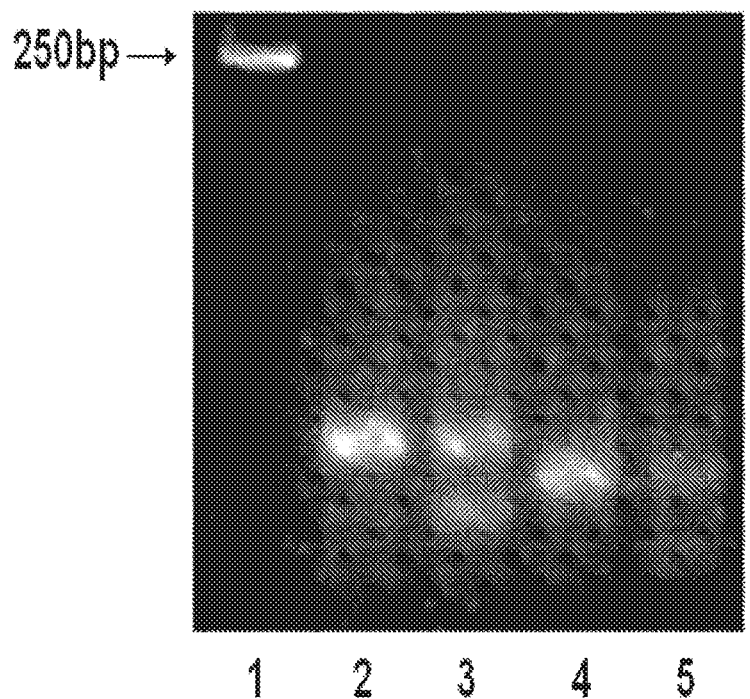
FIG. 42B illustrates an electrophoresis analysis; as discussed in detail in Example 4, below.

FIG. 42A illustrates exemplary library inserts to corroborate quality, clones were sequenced to confirm their randomness; FIG. 42B illustrates an electrophoresis analysis.

Exemplary assays of the invention are constructed in T-cells to facilitate the identification of novel drugs targeting viral envelope processing. Assays of the invention represent a novel way to monitor processing by ER-trans-Golgi resident peptidases. As such, assays of the invention enable both the search for novel inhibitors, and further help elucidate mechanisms of protein cellular membrane transport. In alternative embodiments, assays of the invention are used to screen random peptide libraries and/or small molecule libraries for the discovery of possible novel inhibitors that will target gp160 processing rather than Furin activity.

A number of embodiments of the invention have been described. Nevertheless, it will be understood that various modifications may be made without departing from the spirit and scope of the invention. Accordingly, other embodiments are within the scope of the following claims.

What is claimed is:

1. A cell-based method for monitoring the activity and subcellular location of a protease, comprising:
   (a) providing a nucleic acid encoding a scaffold protein operatively linked to a transcriptional regulatory unit, wherein the scaffold protein comprises:
      (i) an amino acid motif or subsequence susceptible to cleavage by the protase comprising SEQ ID NO:3;
      (ii) a transmembrane domain;
      (iii) a signal sequence or any amino acid motif that places the scaffold protein on the extracellular surface of the cell; and
      (iv) a detectable moiety,
      wherein the amino acid motif or subsequence susceptible to cleavage by the protease is positioned within the scaffold protein such that when the detectable moiety is cleaved away from or off from the scaffold protein by the protease the remaining subsequence of scaffold protein on the extracellular surface of the cell lacks the detectable moiety;
   (b) providing a nucleic acid encoding the protease operatively linked to a transcriptional regulatory unit, or a cell that expresses a heterologous or endogenous protease;
   (c) inserting or transfecting the nucleic acid of (a) into the cell, and also (b) into the cell if the cell does not already express a heterologous or endogenous;
   (d) co-expressing the nucleic acid of (a), and (b) in the cell, or expressing the nucleic acid of (a) in the cell if the cell already expresses a heterologous or endogenous protease; and (e) determining whether the scaffold protein comprising the detectable moiety is expressed on the extracellular surface of the cell, (f) wherein an intact scaffold protein comprising the detectable moiety is expressed on the extracellular surface of the cell when the protease is not enzymatically active, and an intact scaffold protein is not or is substantially less expressed on the extracellular surface of the cell when the protease is enzymatically active, and the detectable moiety can be located at the site of the intracellular cleavage event, if any.

2. The method of claim 1, further comprising: screening for an inhibitor of a protease by:

(a) providing a compound to be screened as an inhibitor of a protease, or providing a nucleic acid to be screened as encoding an inhibitor of a protease;

(b) contacting a plurality of the cells with the compound or nucleic acid of (a) either before, during and/or after the co-expressing the nucleic acid of claim 1 (a) and claim 1 (b) in the cell; and (c) determining whether the scaffold protein comprising the detectable moiety is expressed on the extracellular surface of the cell, wherein an intact scaffold protein comprising the detectable moiety is expressed on the extracellular surface of the cell when the protease, is inhibited by: the compound, a composition encoded by the nucleic acid, or a compound present in the cell only because the nucleic acid was expressed, and an intact scaffold protein is not or is substantially less expressed on the extracellular surface of the cell when the protease is enzymatically active or the detectable moiety is cleaved off by the protease, and the enzymatic activity of the protease, is not significantly inhibited by: the compound, a composition encoded by the nucleic acid, or a compound present in the cell only because the nucleic acid was expressed.

3. The method of claim 2, further comprising running a negative control comprising dividing the plurality of the cells co-expressing the nucleic acid of (a) and (b) in the cell and not adding the compound to be screened as an inhibitor to one of the divided cell samples.

4. The method of claim 2, further comprising running a positive control comprising dividing the plurality of the cells co-expressing the nucleic acid of (a) and (b) in the cell and adding a known inhibitor of the protease to one of the divided cell samples.

5. The method of claim 1, wherein: the amino acid motif or subsequence comprises SEQ ID NO:3 and SEQ ID NO:4.

6. The method of claim 1, wherein the scaffold protein further comprises a p2/p7 recognition site imbedded in the cytoplasmic loop of the scaffold.

7. The method of claim 1, wherein the protease is an HIV protease.

8. The method of claim 1, wherein the transcriptional regulatory unit comprises a promoter, an inducible promoter or a constitutive promoter.

9. The method of claim 1, wherein the cell is a mammalian cell, a monkey cell or a human cell.

10. The method of claim 1, wherein the scaffold proteins comprise all or part of a mouse Lyt2 or a human CD8 polypeptide.

11. The method of claim 1, wherein the detectable moiety comprises an epitope for an antibody, or a FLAG tag.

12. The method of claim 1, wherein the detectable moiety is detected or measured on the extracellular surface of the cell by a high throughput screen, a flow cytometry or microscope visualization.

13. The method of claim 1, wherein the compound to be screened as an inhibitor of the protease comprises a small molecule, a nucleic acid, a polypeptide or peptide, a peptidomimetic, a polysaccharide or a lipid.

14. The method of claim 1, wherein the compound to be screened as an inhibitor of the protease is a member of a library of compounds to be screened, or a member of a random peptide library or a chemical compound library.

15. The method of claim 7, wherein the HIV protease comprises a sequence as set forth in SEQ ID NO:5 or SEQ ID NO:6.

* * * * *